(12) United States Patent
Soykan

(10) Patent No.: US 8,027,791 B2
(45) Date of Patent: Sep. 27, 2011

(54) SELF-IMPROVING CLASSIFICATION SYSTEM

(75) Inventor: Orhan Soykan, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1005 days.

(21) Appl. No.: 11/157,514

(22) Filed: Jun. 21, 2005

(65) Prior Publication Data

US 2006/0019397 A1  Jan. 26, 2006

Related U.S. Application Data

(60) Provisional application No. 60/589,907, filed on Jul. 21, 2004, provisional application No. 60/582,352, filed on Jun. 23, 2004.

(51) Int. Cl.
*G01N 33/48* (2006.01)

(52) U.S. Cl. .......................................................... 702/19

(58) Field of Classification Search .................. None
See application file for complete search history.

(56) References Cited

U.S. PATENT DOCUMENTS

| | | | |
|---|---|---|---|
| 5,018,067 A | 5/1991 | Mohlenbrock et al. | |
| 5,437,285 A | 8/1995 | Verrier et al. | |
| 6,099,469 A | 8/2000 | Armstrong | |
| 6,210,976 B1 | 4/2001 | Sabbadini | |
| 6,274,332 B1 | 8/2001 | Keating et al. | |
| 6,306,087 B1 | 10/2001 | Barnhill | |
| 6,368,823 B1 | 4/2002 | Bril | |
| 6,432,644 B1 | 8/2002 | Keating et al. | |
| 6,458,542 B1 | 10/2002 | George, Jr. et al. | |
| 6,500,630 B2 | 12/2002 | Conover | |
| 6,571,129 B2 | 5/2003 | Schaldach | |
| 6,597,952 B1 | 7/2003 | Mika | |
| 6,647,341 B1 | 11/2003 | Golub et al. | |
| 6,727,063 B1 | 4/2004 | Lander et al. | |
| 7,208,273 B2 | 4/2007 | Keating | |
| 7,608,458 B2 | 10/2009 | Soykan et al. | |
| 7,622,303 B2 | 11/2009 | Soykan et al. | |
| 2002/0049772 A1 | 4/2002 | Rienhoff, Jr. et al. | |
| 2002/0059030 A1 | 5/2002 | Otworth | |
| 2002/0076809 A1 | 6/2002 | Steinmeyer et al. | |
| 2002/0077470 A1 | 6/2002 | Walker et al. | |
| 2002/0086297 A1 | 7/2002 | Siffert | |
| 2002/0115073 A1 | 8/2002 | Papadopoulos et al. | |
| 2002/0155539 A1 | 10/2002 | Ruben et al. | |
| 2002/0165161 A1 | 11/2002 | Allison | |
| 2002/0182599 A1 | 12/2002 | Fishman | |
| 2003/0004402 A1 | 1/2003 | Hitt et al. | |
| 2003/0096782 A1 | 5/2003 | Bristow et al. | |
| 2003/0108924 A1 | 6/2003 | George, Jr. et al. | |
| 2003/0162192 A1 | 8/2003 | Sotos et al. | |
| 2003/0175795 A1 | 9/2003 | Walker et al. | |
| 2003/0198970 A1 | 10/2003 | Roberts | |
| 2003/0228565 A1 | 12/2003 | Oestreicher et al. | |
| 2003/0235838 A1 | 12/2003 | Keating et al. | |
| 2004/0009495 A1 | 1/2004 | O'Malley et al. | |
| 2004/0029259 A1 | 2/2004 | McDevitt | |
| 2004/0058388 A1 | 3/2004 | Hitt et al. | |
| 2004/0219685 A1 | 11/2004 | Pappin et al. | |
| 2005/0053956 A1 | 3/2005 | Dietz et al. | |
| 2005/0130190 A1 | 6/2005 | Antzelevitch et al. | |
| 2005/0142591 A1 | 6/2005 | Ackerman | |
| 2005/0181386 A1 | 8/2005 | Diamond et al. | |
| 2006/0063162 A1 | 3/2006 | Deng | |
| 2006/0147450 A1 | 7/2006 | Shelton | |
| 2007/0026393 A1 | 2/2007 | Berlin et al. | |
| 2007/0038386 A1* | 2/2007 | Schadt et al. .................... 702/20 |
| 2007/0042382 A1 | 2/2007 | Cargill et al. | |
| 2007/0054278 A1 | 3/2007 | Cargill | |
| 2007/0065865 A1 | 3/2007 | Carlton et al. | |
| 2007/0082347 A1 | 4/2007 | Lanchbury et al. | |
| 2007/0141570 A1 | 6/2007 | Braun et al. | |
| 2010/0021903 A1 | 1/2010 | Johnson et al. | |

FOREIGN PATENT DOCUMENTS

| | | |
|---|---|---|
| EP | 0721786 B1 | 7/1996 |
| EP | 0842475 B1 | 2/1997 |
| EP | 1100825 B1 | 2/2000 |
| EP | 1 176 197 A1 | 1/2002 |
| EP | 1480251 A2 | 11/2004 |
| WO | WO 95/15116 | 6/1995 |
| WO | WO 96/28537 | 9/1996 |
| WO | WO 98/09226 | 3/1998 |
| WO | 9843630 A1 | 10/1998 |
| WO | 99/27140 A1 | 6/1999 |
| WO | 99/51778 A1 | 10/1999 |
| WO | 99/67628 A1 | 12/1999 |
| WO | 0127158 A2 | 4/2001 |
| WO | WO 01/81895 A2 | 11/2001 |
| WO | WO 01/92567 A2 | 12/2001 |
| WO | 02/52033 A1 | 7/2002 |
| WO | WO 02/86447 A2 | 10/2002 |
| WO | WO 03/002757 A1 | 1/2003 |

(Continued)

OTHER PUBLICATIONS

Alizadeh et al. Nature, vol. 403, p. 503-511, 2000.*

Li et al. American Journal of Pathology, vol. 158, No. 4, Apr. 2001, 1231-1237.*

Millan et al. Theoretical and Applied Genetics (1996), 92(2), 273-277.*

Fananapazir, et al., Genotype-Phenotype Correlations in Hypertrophic Cardiomyopathy: Insights Provided by Comparisons of Kindreds with Distinct and Identical Beta-myosin Heavy Chain Gene Mutations, Circulation, 1994; 89(1): 22-32.

Iwasa, et al., Multiple Single-Nucleotide Polymorphisms (SNPS) in the Japanese Population in Six Candidate Genes for Long QT Syndrome, J. Hum. Genet., 2001; 46: 158-62.

(Continued)

*Primary Examiner* — Michael Borin
(74) *Attorney, Agent, or Firm* — Kenneth J. Collier; Hahn & Voight PLLC; Roger C. Hahn

(57) ABSTRACT

A self-improving classification system classifies specimens based on class identifiers. The system stores specimen profiles in a database that is updated with additional specimen profiles and with follow-up data that corrects classification of specimens that were initially incorrectly classified. Algorithms use the updated database to discover new class identifiers, modify thresholds of known class identifiers, and drop unnecessary class identifiers to improve classification of specimens.

13 Claims, 20 Drawing Sheets

FOREIGN PATENT DOCUMENTS

| WO | WO 03/006687 A2 | 1/2003 |
|---|---|---|
| WO | WO 03/040407 A2 | 5/2003 |
| WO | 03087819 A1 | 10/2003 |
| WO | WO 2004/005931 | 1/2004 |
| WO | 2006092660 A1 | 9/2006 |
| WO | 2006131528 A2 | 12/2006 |
| WO | 2007025080 A2 | 3/2007 |
| WO | 2007055602 A1 | 5/2007 |

OTHER PUBLICATIONS

Frank-Hansen, et al., Mutations in the Genes KCND2 and KCND3 Encoding the Ion-Channels Conducting the Cardiac Transient Outward Current (ITO) is not a Frequent Cause of Long QT Syndrome, Am. J. Hum. Genet., 2002; 71(4 Supp.): 521.
Issaq, et al., The SELDI-TOF MS Approach to Proteomics: Protein Profiling and Biomarker Identification, Biochemical and Biophysical Research Communications, Apr. 5, 2002; 292(3): 587-92.
Hegele, SNP Judgments and Freedom of Association, Arteriosclerosis, Thrombosis, and Vascular Biology, 2002; 22: 1058-61.
Splawski, et al., Variant of SCN5A Sodium Channel Implicated in Risk of Cardiac Arrhythmia, Science, Aug. 23, 2002; 297: 1333-36.
Towbin, et al., Molecular Biology and the Prolonged QT Syndrome, The Am. J. Medicine, Apr. 1, 2004; 110(5): 385-98.
Arking, et al., Genomics in Sudden Cardiac Death, Circulation Research, 2004; 94: 712-23.
'Peptide' may help predict early heart disease, CNN.com, Feb. 12, 2004, 1-3.
NCBI Database SNP [Online], Sep. 7, 2000, refSNP ID: ss1472059.
NCBI Database SNP [Online], Oct. 20, 2000, refSNP ID: rs1538389; & NCBI Database SNP [Online], Oct. 20, 2000, refSNP ID: ss2379946.
NCBI Database SNP [Online], refSNP ID: rs1808973; & NCBI Database SNP [Online], Jan. 2, 2001, refSNP ID: ss2672972.
NCBI Database SNP [Online], refSNP ID: rs730022 & NCBI Database SNP [Online], Sep. 6, 2000, refSNP ID: ss74946.
Dhar et al., Prognostic significance of metastatic lymph node size in patients with gastric cancer, British J. of Surgery, 2003; 90: 1522-30.
Kuzuya et al., Report of the Committee on the classification and diagnostic criteria of diabetes mellitus, Diabetes Res. and Clin. Practice, 2002; 55: 65-85.
Office Action from the USPTO in U.S. Appl. No. 11/157,532 mailed Mar. 29, 2007.
Iwasa, et al., J. Hum. Genet., 2002; 47: 208-212.
Ackerman, et al., Heart Rhythm, 2004; 1:600-607.
Hirschhorn, et al., Genetics in Medicine, 2002; 4: 45-61.
Amendment and Response to Office Action filed with the USPTO in U.S. Appl. No. 11/157,532 on Jun. 13, 2007.
Josephson, M., et al., Circulation, 2004; 109: 2685-2691.
Article, Dominic Aronsky, MD, et al., An Integrated Decision Support System for Diagnosing and Managing Patients with Community-Acquired Pneumonia, pp. 1-5., 1999.
Article, Isabelle Colombet MD, et al., Decision Aids for Triage of Patients with Chest Pain: A Systematic Review of Field Evaluation Studies, pp. 1-5., 1999.
Nick Christodoulides, et al., A Microchip-Based Multianalyte Assay System for the Assessment of Cardiac Risk, Analytical Chemistry, vol. 74, No. 13, Jul. 1, 2002, pp. 3030-3036.
Xavier Jouven, MD, et al., Circulating Nonesterified Fatty Acid Level as a Predictive Risk Factor for Sudden Death in the Population, Circulation. 2001:104:pp. 756-761.
Xavier Jouven, MD, et al., Predicting Sudden Death in the Population, The Paris Prospective Study I, Circulation. 1999:99:pp. 1978-1983.
Michael J. Dunn, Studying Heart Disease Using the Proteomic Approach, DDT, vol. 5, No. 2, Feb. 2000, pp. 76-84.
Nilesh J. Samani, MD, et al., A Meta-analysis of the Association of the Deletion Allele of the Angiotensin-Converting Enzyme Gene With Myocardial Infarction, Circulation. 1996:94:708-712.
D. Kent Arrell, et al., Cardiovascular Proteomics, Evolution and Potential, Circ. Res. 2001; 88:pp. 763-773.
Urban A. Kiernan, et al., Comparative Urine Protein Phenotyping Using Mass Spectrometric Immunoassay, Research articles from Journal of Proteome Research, pp. 1-7.
Eleftherios P. Diamandis, Proteomic Patterns in Biological Fluids: Do They Represent the Future of Cancer Diagnostics?, Clinical Chemistry 49:8, pp. 1272-1278, 2003.
Emanuel F. Petricoin III, et al., Use of Proteomic Patterns in Serum to Identify Ovarian Cancer, The Lancet, vol. 359, Feb. 16, 2002, pp. 572-577.
Ken Rubenstein, Ph.D., et al., Post-Genomic Biomarkers: Revolutionizing Drug Development and Diagnostics, Report #9129, Sep. 2003, D&MD Publications.
Arthur J. Moss, MD, et al., Increased Risk of Arrhythmic Events in Long-QT Syndrome with Mutations in the Pore Region of the Human Ether-a-go-go-Related Gene Potassium Channel, Circulation. 2002:105-794-799.
Danne et al., Prognostic Implications of Elevated Whole Blood Choline Levels in Acute Coronary Syndromes, The Am. J. Cardiology, May 1, 2003, 91(9): 1060-67.
Towbin et al., Molecular Biology and the Prolonged QT Syndrome, The Am. J. Medicine, Apr. 1, 2004, 110(5): 385-98.
Shiffman et al., Identification of Four Gene Variants Associated with Myocardial Infarction, Am. J. Hum. Genet., 2005, 77(4): 596-605.
Xiao et al., Poly(ADP-ribose) polymerase promotes cardiac remodeling, contractile failure, and translocation of apoptosis-inducing factor in a murine experimental model of aortic banding and heart failure., J. of Pharma. And Experimental Therapeutics, Mar. 2005, 312(3): 891-898.
Stevens et al., Oxidative-nitrosative stress as a contributing factor to cardiovascular disease in subjects with diabetes., Current Vascular Pharma., Jul. 2005, 3(3): 253-266.
NCBI Database SNP [Online], Aug. 2002, refSNP ID: rs3775296.
NCBI Database SNP [Online], Oct. 2000, refSNP ID rs: 1439098.
NCBI Database SNP [Online], Feb. 2004, refSNP ID rs: 122666315.
NCBI Database SNP [Online], Jun. 2003, refSNP ID rs: 6974082.
NCBI Database SNP [Online], Sep. 2001, refSNP ID rs: 2716727.
NCBI Database SNP [Online], Jul. 2000, refSNP ID rs: 564275.
NCBI Database SNP [Online], Nov. 2003, refSNP ID: rs10505726.
NCBI Database SNP [Online], refSNP ID: 4878412, retrieved Apr. 9, 2009.
Zipes et al., Sudden Cardiac Death, Circulation, 1998; 98:2334-2351.
Yang et al., Recent developments in primer design for DNA polymorphism and mRNA profiling in higher plants, Plant Methods, 2006; 2(1):4.
Cai et al., Direct electrical detection of hybridization at DNA-modified silicon surfaces, Biosensors and Bioelectronics, 2004; 19(9):1013-1019.
Steemers et al., Screening unlabled DNA targets with randomly ordered fiber-optic gene arrays, Nat. Biotechnol., 2000; 18: 91-94.
Spear et al., Clinical application of pharmacogenetics, Trends in Molecular Medicine, 2001; 7(5):201-204.
Pham et al., T-Wave alternans: Marker, mechanism, and methodology for predicting sudden cardiac death, J. of Electrocardiology, 2003, 36 Supp. 75-81.
Miller et al., A simple salting out procedure for extracting DNA from human nucleated cells, Nucleic Acids Res., 1988; 16(3): 1215.
Michael et al., Randomly ordered addressable high-density optical sensor arrays, Anal. Chem., 1998; 70: 1242-1248.
Grunstein et al., Colony hybridization: A method for the isolation of cloned DNAs that contain a specific gene, Proc. Nat. Acad. Sci. USA, 1975; 72(10):3961-3965.
Sambrook et al., Molecular Cloning—A laboratory manual, Cold Spring Harbor. Labs., 1989.
Fulton et al., Advanced multiplexed analysis with the FlowMetrixO system, Clin. Chem. 1997; 43(9): 1749-1756.
Devlin and Risch, A comparison of linkage disequilibrium measures for fine-scale mapping, Genomics, 1995; 29 (2):311-322.
Buxton, Risk stratification for sudden death: Do we need anything more than Ejection Fraction?, Cardiac Electrophysiology Review, 2003; 7:434-437.
Abd-Elsalam, Bioinformatic tools and guideline for PCR primer design, African J. Biotechnol., 2003: 2(5): 91-95.

NCBI Database SNP [Online], refSNP ID: rs11196566, Nov. 18, 2003.

NCBI Database SNP [Online], refSNP ID: rs151600, Jun. 30, 2000.

NCBI Database SNP [Online], refSNP ID: rs151603, Jun. 30, 2000.

Johnson et al., Beta-adrenergic receptor polymorphisms: cardiovascular disease associations and pharmacogenetics, Pharmaceutical Research, Dec. 2002, 19(12): 1779-1787.

Liu et al., Gly389Arg polymorphism of beta 1-adrenergic receptor is associated with the cardiovascular response to metoprolol, Clinical Pharmacology and Therapeutics, Nature Publishing Group, U.S., Oct. 1, 2003, 74(4): 372-379.

U.S. Appl. No. 11/050,611, filed Feb. 3, 2005, Soykan et al.
U.S. Appl. No. 11/157,549, filed Jun. 21, 2005, Soykan et al.
U.S. Appl. No. 12/606,173, filed Oct. 26, 2009, Soykan et al.
U.S. Appl. No. 11/157,568, filed Jun. 21, 2005, Soykan et al.
U.S. Appl. No. 11/157,532, filed Jun. 21, 2005, Soykan et al.
U.S. Appl. No. 12/271,338, filed Nov. 14, 2008, Soykan et al.
U.S. Appl. No. 12/271,385, filed Nov. 14, 2008, Soykan et al.
U.S. Appl. No. 12/778,603, filed May 12, 2010, Soykan et al.

* cited by examiner

SELF-IMPROVING CLASSIFICATION SYSTEM

This application claims the benefit of U.S. Provisional Application Nos. 60/589,907 filed on Jul. 21, 2004 for "GENETIC DIAGNOSTIC METHOD FOR SCD RISK STRATIFICATION" by O. Soykan and D. Cross and 60/582,352 filed on Jun. 23, 2004, for "SELF-IMPROVING CLASSIFICATION SYSTEM" by O. Soykan.

CROSS-REFERENCE TO RELATED APPLICATIONS

This application is related to applications entitled "Self-Improving Identification Method", "Genetic Diagnostic Method for SCD Risk Stratification" and "Assessing Patient Risk with Biochemical Markers," which were filed on the same day and also assigned to Medtronic, Inc.

BACKGROUND OF THE INVENTION

The present invention relates to a system and method for classifying biological specimens. In particular, the present invention relates to building and improving a system and method for classifying biological specimens.

Classification of biological specimens has broad applications in the healthcare and research fields. Its uses range from diagnosing whether or not a patient has a disease, to determining which therapy will work for a particular patient, to determining the subclass of a tumor or microorganism. Though classification is performed routinely, it is often a difficult and imprecise process. Diagnosis of patients with incomplete symptoms or partially penetrated phenotypes, for instance, is a common, but difficult, problem.

For example, there are multiple tests to identify patients who are susceptible to life threatening arrhythmias. However, none of these tests have the desired specificity and sensitivity to reliably identify all patients at risk. As a result, many of these patients do not receive optimal therapy, and lives are lost every year.

Current diagnostic or classification techniques utilize symptoms reported by patients, the presence or measurement of biological and physiological markers, and the experience and intuition of the healthcare provider. In order to make classification more reliable, researchers have tried to identify new biological and physiological markers. Current scientific methods for discovering new markers require previous knowledge of the biochemical pathway for a particular disease or process. In addition, only one marker can be studied at a time—making it a difficult, expensive, and lengthy process.

It is likely that many indicators associated with each disease or condition exist, but medical knowledge has not yet hypothesized their roles in these pathways. Therefore, there is a need for an improved process for classifying biological specimens and identifying new indicators to continually improve the process.

BRIEF SUMMARY OF THE INVENTION

The present invention is a method and system for classifying specimens. An algorithm for classifying specimens is derived from class identifiers. Specimens are classified by analysis of profiles generated for each specimen. If it is subsequently determined that a specimen is incorrectly classified, that specimen profile is reclassified. The algorithm is then refined based on data from the reclassified specimen profile.

DESCRIPTION

Figure 1:
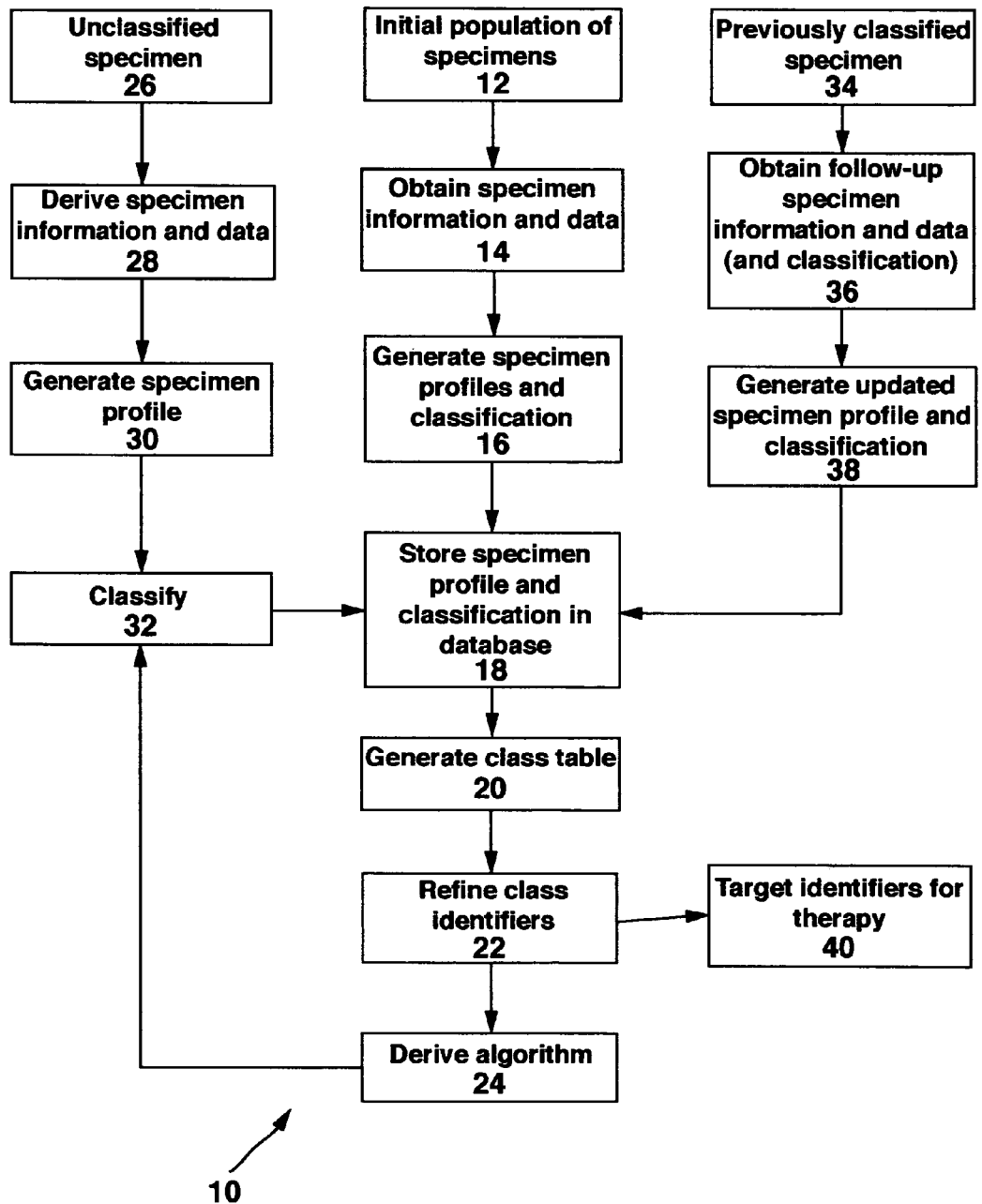
FIG. 1 is a flowchart of a representative embodiment of the present invention.

The Self-Improving Classification Process (FIG. 1)

The present invention is a system and method to build and implement a process that can be used to classify any biological specimen. Specimens can be a person, an animal, a plant, a tissue sample, a bodily fluid sample, cells, subcellular factors, and microorganisms. Specimens can be sorted into a class based on any type of distinction as well. Examples of class distinctions are risk, diagnosis, or prognosis of a disease or condition (for example, diabetes); the ideal therapy against a condition; the ideal route of administering a therapy; whether there would be a benefit from therapy (either drug or medical device therapy); recovery from a condition; the class of a tumor; the specific type of an infection; etc.

FIG. 1 is a flowchart of classification process 10, which is a representative embodiment of the present invention. Process 10 begins with initial population of specimens 12, which are specimens that are of known classification.

At step 14, specimen information and data are obtained from initial population of specimens 12. The information and data can be of any type and will be described in more detail below.

At step 16, specimen profiles are generated for each specimen of the initial population. The specimen profiles are based on the information and data obtained from the specimens. The classification of the specimen profile and specimen, based on prior knowledge, is established. The specimen profile and classification is then stored in a database at step 18.

Next, at step 20, a class table is generated. The class table is a vector where each entry represents the number of specimens with a given condition. The class table does not specify which specimens belong to each class, but instead, provides comprehensive information of the specimen population (e.g. the frequency of a given disease in the general public). For example, a vector of [6, 45, 76, . . . ] means that 6 specimens have condition 1, 45 specimens have condition 2, 76 specimens have condition 3, etc. The entries and number of entries in the class table are dynamic. If the distinctions of the class table are diseases, for example, the class table may also be referred to as a disease table.

The class table is subsequently used, at step 22, to refine class identifiers. Class identifiers are benchmarks that distinguish classes. Class identifiers are based on any type of information and data that is gathered from the specimens, such as proteomic, genetic, and lipidomic biological markers, as well as physiologic and demographic parameters. At this point, the class identifiers may be any combination of previously known and newly identified class identifiers. Refining class identifiers includes discovering new class identifiers, modifying thresholds of class identifiers, and dropping unnecessary class identifiers.

At step 24, an algorithm to classify specimens is derived or developed. The algorithm is based on the class identifiers.

The next part of process 10 begins with unclassified specimen 26. The classification of unclassified specimen 26 is unknown.

At step 28, specimen information and data is derived from unclassified specimen 26. A specimen profile is then generated at step 30.

The algorithm developed at step 24 is utilized at step 32 to classify unclassified specimen 26. The resulting classification along with the specimen profile, are stored in the database represented by step 18. The profile and classification of specimen 26 is used (along with other stored profiles and classifications in the database) to generate a class table (step 20), refine class identifiers (step 22), and derive an algorithm (step 24) as described previously. The means for deriving an algorithm, which includes updating and improving, is preferably a digital processor such as a computer.

The remaining part of process 10 begins with previously classified specimen 34. This is a specimen that was previously unclassified but has now been initially classified and has its profile and classification stored in the database.

At step 36, follow-up data, which includes any of the type of data and information that is described below, is obtained from previously classified specimen 34. The follow-up data can include, among other things, a correction to the specimen's classification. If the specimen was initially incorrectly classified, and it is later determined that the original classification was incorrect, the correct classification is obtained in the follow-up data.

The follow-up data is used to generate an updated specimen profile and classification at step 38. The updated specimen profile and classification is then stored in the database as shown by step 18. Alternatively, the specimen classification may not be entered into the database until after it is determined whether or not the initial classification was correct. Again, the updated and stored profile and classification is utilized in generating a class table (step 20), refining class identifiers (step 22), and deriving an algorithm (step 24) as described above.

Optionally, step 40 shows that the refined class identifiers from step 22 may be studied as targets for therapy of a given condition. This will be described in more detail below.

The algorithm of process 10 self-improves to increase the sensitivity (positive predictive value) and the specificity of process 10 and identifies new and/or more predictive classes. Utilizing the follow-up specimen information and data with any corrected classifications, as shown by step 36, are key to improving process 10. For example, a specimen is classified based on the specimen's profile, using the algorithm, as having a given condition. However, it is later determined that the specimen was incorrectly classified and does not have the given condition. If the information and data in the specimen profile is used to refine the algorithm without reclassifying the specimen, the algorithm will not be improved and will likely continue to incorrectly classify similar specimens. If, however, the specimen is reclassified, and the profile is utilized in refining the algorithm, the algorithm will improve and be less likely to incorrectly classify a similar specimen.

Reclassification will also correct any problems in the algorithm that are the result of a skewed initial population of specimens 12 that was used to initially generate the algorithm. For example, many of the specimens in initial population 12 having a given condition also, coincidentally, have a given class identifier. This is picked up and utilized by the algorithm to distinguish those with the condition, while in reality the class identifier is not associated with the condition. Many subsequently classified specimens will be incorrectly classified using this algorithm. If these specimens are not reclassified when it is determined that the classification is not correct, the incorrect algorithm will be perpetuated. However, by reclassifying the specimens, the error based on the skewed initial population 12 is corrected. However, an initial skew in the data might help determine population specific class identifiers. For example, if an initial population was not balanced for gender or ethnic origins, then the initial class identifiers could be specific to the over-represented subgroups, which can increase the specificity of future tests. Thus, the present invention improves process 10 beyond just increasing the amount of data from which to derive an algorithm.

Figure 2:
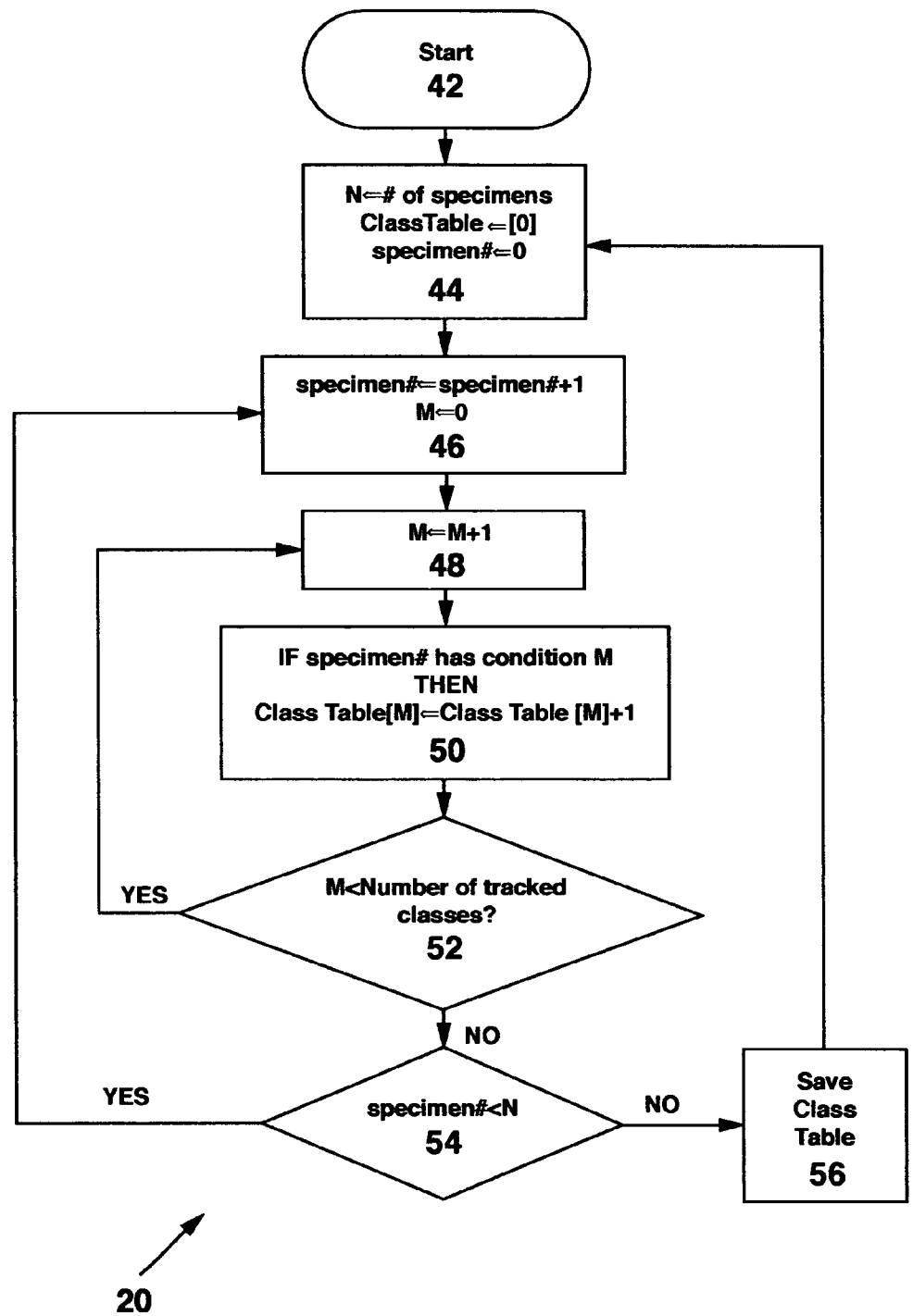
FIG. 2 is a flowchart of an algorithm to generate and update a class table.

Class Table Generation (FIG. 2)

FIG. 2 is an algorithm, detailing step 20, for generating a class table. Generating the class table includes updating the class table. The means for generating the class table is preferably a digital processor. Here, N represents the total number of specimens in the database, and M represents a given class.

To construct the class table, the processor starts at step 42. At step 44, the total number of specimens in the database is determined, the class table is null, and no specimens are being considered.

The first specimen is then considered at step 46 along with the first class in step 48. If the first specimen belongs in the first class, then one is added to the first position of the vector, as indicated in step 50, to show that the number of specimens in class M has increased by 1.

At step 52, the processor considers whether all of the classes have been tracked for the first specimen. If more classes must be considered, the processor returns to step 48 and considers the next class. If all the classes have been considered for the first specimen, the processor continues to step 54.

At step 54, the processor considers whether the total number of specimens in the database has been considered. If more specimens must be considered, the processor returns to step 46 and considers the second specimen. If all specimens have been considered, the processor proceeds to step 56, where the class table is saved.

As the database is updated with more specimens and with corrected classifications of specimens, the algorithm of step 20 is run to update the class table. Preferably, the algorithm of step 20 runs as an infinite loop to continuously update the class table. Alternatively, it may be run only periodically or as new data becomes available.

Figure 3:
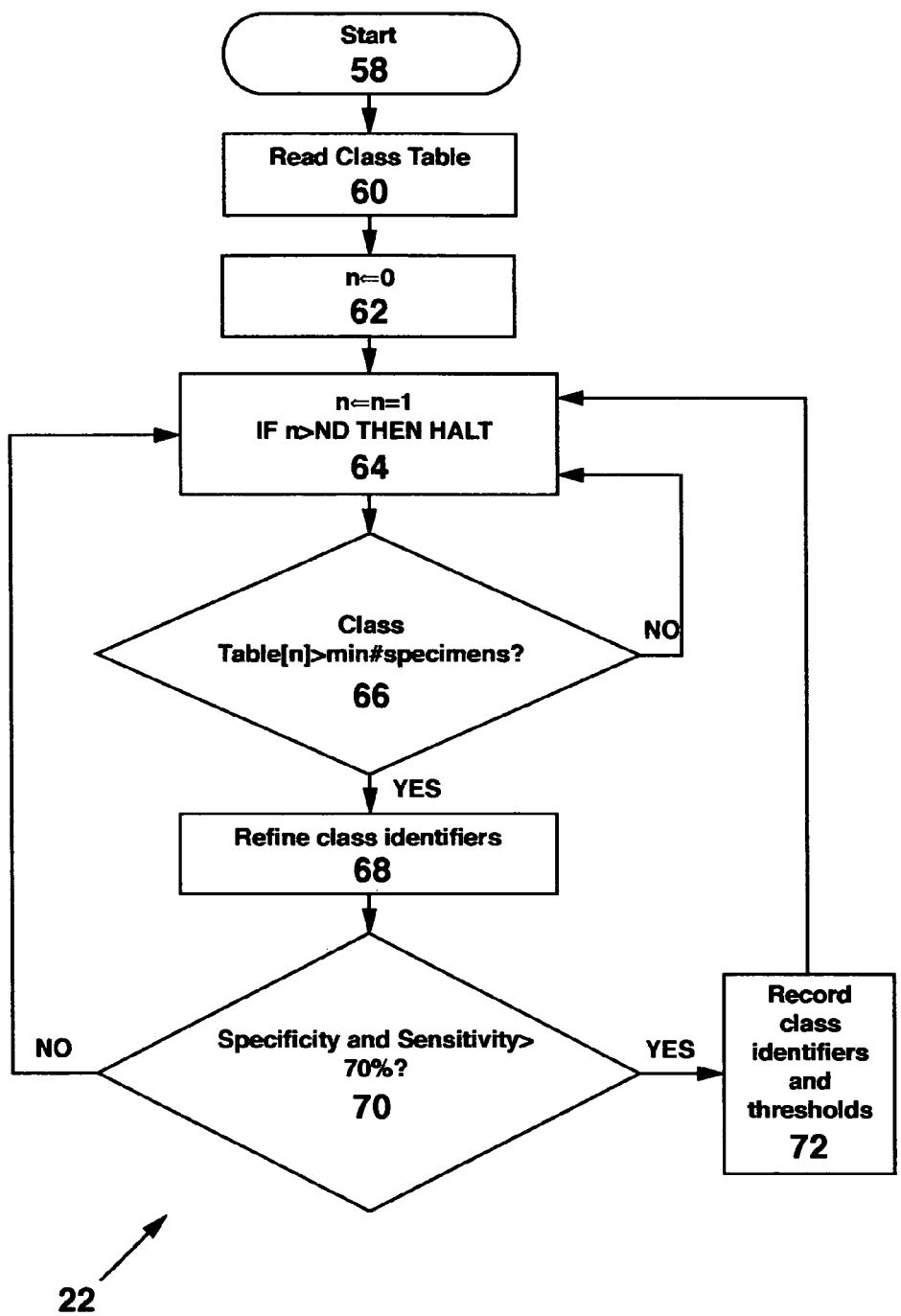
FIG. 3 is a flowchart of an algorithm to refine class identifiers.

Refine Class Identifiers (FIG. 3)

Once the class table is updated, the class identifiers are refined. Again, refining class identifiers includes discovering new class identifiers, dropping out unnecessary class identifiers, and modifying thresholds of current class identifiers. The means for refining the class identifiers is preferably a digital processor. FIG. 3 shows an algorithm, detailing step 22, for refining class identifiers. Here, ND represents the total number of conditions to be searched, and n represents a given condition.

The processor starts at step 58 and proceeds to read the class table at step 60. At step 62, the processor counts the classes and subsequently determines, at step 64, whether the total number of classes to be searched has been considered. If all the classes have been considered, the processor stops at step 64. If all the classes have not been considered, the processor continues to step 66 where it determines, from the class table, whether class n contains the minimum number of specimens needed to continue.

The optimal minimum number of specimens for refinement is approximately 250. However, for initial discovery of class identifiers, the minimum number of specimens can be much lower. Therefore, the minimum number of specimens needed for continuation preferably is about 45.

If at least the minimum number of specimens is placed in class n, the processor continues to step 68. At step 68, the processor refines the class identifiers for class n.

At step 70, the specificity and sensitivity (positive predictive value) of classification based on the refined class identifiers are calculated. If they are greater than about 70%, the class identifiers and thresholds are recorded at step 72. As a cross-check, a person then evaluates the refined algorithm before it is actually implemented to classify patients.

To search for new class identifiers, drop unnecessary class identifiers, and modify thresholds at step 68 of FIG. 3, specimens in the database are first categorized based on their condition. For simplification, two categories are considered here, NORMAL and DISEASED. However, there may be more categories depending on the class distinction. If a specimen's classification is unknown for the condition, then that specimen is excluded from the analysis.

The collection of potential class identifiers from the specimen profiles in the database is searched to determine class identifiers specific to a classification. Cluster analysis is the preferred method for searching, and any of a number of methods may be used to cluster specimens. Besides refining class identifiers (step 22), these methods can also be used to classify specimens (step 32). Some examples include:

Linear Methods—

Linear Regression Coefficients are calculated for all the class identifiers to get a linear equation, which would give vastly different values for specimens in different classes. A threshold value can be used as a separator to break the specimens into clusters.

Proximity: The distance between points representing each specimen is calculated in multi-dimensional Euclidian geometry, while seeking mutually exclusive clustering of the specimens. Removal of one or more of the dimensions, which represent potential class identifiers, is tried in an attempt to reduce the overlap and increase the distance between the clusters. The best case is chosen, and the potential class identifiers forming the dimensions of the space are declared class identifiers for the class.

Similarity/Dissimilarity: Instead of calculating the geometric distance between points representing specimens, each potential class identifier is studied one by one and required to be similar between the specimens. A similarity measure is calculated and minimized by removing the most offending potential class identifier from the set. The search is terminated when similarity is maximized/dissimilarity is minimized. The remaining potential class identifiers are declared class identifiers for the class.

Weighted Proximity: This method is similar to the Proximity analysis except that some potential class identifiers are weighted more heavily than others.

Principle component analysis: New variables are constructed as linear combinations of the entire set of potential class identifiers. Care is taken to make sure that these variables are orthogonal to each other. The total number of new variables should be much less than the number of potential class identifiers. Clustering is achieved using the methods listed above with the new variable set.

Non-Linear Methods:

Artificial Neural Networks: This is a layered and combinatorial processor where inputs are processed by artificial neurons. Neurons receive inputs as linear combinations of potential class identifiers, and output a value based on a non-linear transfer function, such as a sigmoidal function. There are usually three layers of neurons. The first, or input, layer and the second, or hidden, layer usually, but not necessarily, have the same number of neurons as the number of input potential class identifiers, and the third, or output, layer usually has one or two neurons.

Kohonen Networks: This method is very similar to artificial neural networks, except they are formed by a single layer with all neurons connected to each other. They are used for classification of input patterns formed by, in the present case, potential class identifiers.

Pattern Recognizers: Initially, a pattern for each class is formed. For example, average values for each potential class identifier can be calculated for each class. Potential class identifiers providing distinctions, i.e. small standard deviations with large differences in mean values, are kept as class identifiers. Specimens are classified by measuring their proximity or similarity to the mean values.

Empirical curve fitting: This method is similar to linear regression, but a non-linear equation is used instead of a linear equation. The non-linear equation can be a polynomial or can include, for example, exponential, logarithmic, and trigonometric functions. Potential class identifiers contributing maximally for the equation are declared the class identifiers.

Logical:

CART (Classification And Regression Trees): First, all potential class identifiers are individually scanned to identify one that results in the best classification. This yields two groups distinguishable by their values for the potential class identifier. Second, a scan of remaining potential class identifiers is performed for each of the groups to further classify specimens in each group. The process repeats until all or most of the specimens are classified correctly. Potential class identifiers selected for each stage are declared the class identifiers for the class.

Hierarchical Clustering: Multiple methods are possible, but the agglomerative method is described here as a representative example. Proximity or dissimilarity is calculated for each specimen. Specimens with maximum proximity or minimum dissimilarity are clustered and considered a new specimen, which replaces the specimens forming the cluster. The process is repeated until all specimens are clustered into two groups. If clustering is not optimal, then some of the potential class identifiers are removed and the process starts from scratch. Potential class identifiers used in the process that result in optimal clustering are declared the class identifiers.

Partitioning: This method is similar to hierarchical clustering and CART, but multiple thresholds for a given potential class identifier (pci) are used, which results in multiple pathways. For example,
IF pci7>threshold1 THEN . . .
IF threshold1≧pci7>threshold2 THEN . . .
IF threshold2≧pci7>threshold3 THEN . . .
IF threshold3≧pci7 THEN . . .

New class identifiers are discovered, unnecessary class identifiers are dropped, and thresholds of known class identifiers are modified by optimizing the clustering of the specimens. For instance, clustering θ is preferred to clustering θ', if $f(\theta) < f(\theta')$ where $f(\theta)$ is the function to be minimized. It can be defined as but is not limited to:

$$f(\theta) = \text{Radius\_of\_NORMAL\_Cluster} + \text{Radius\_of\_DISEASED\_Cluster} - \text{Distance\_Between\_Clusters},$$
for a given set of potential class identifiers θ

The optimal solution,
θ is optimal, if $f(\theta) < f(\theta')$ for all solutions or, there is no solution that is preferred to θ.

Figure 4:
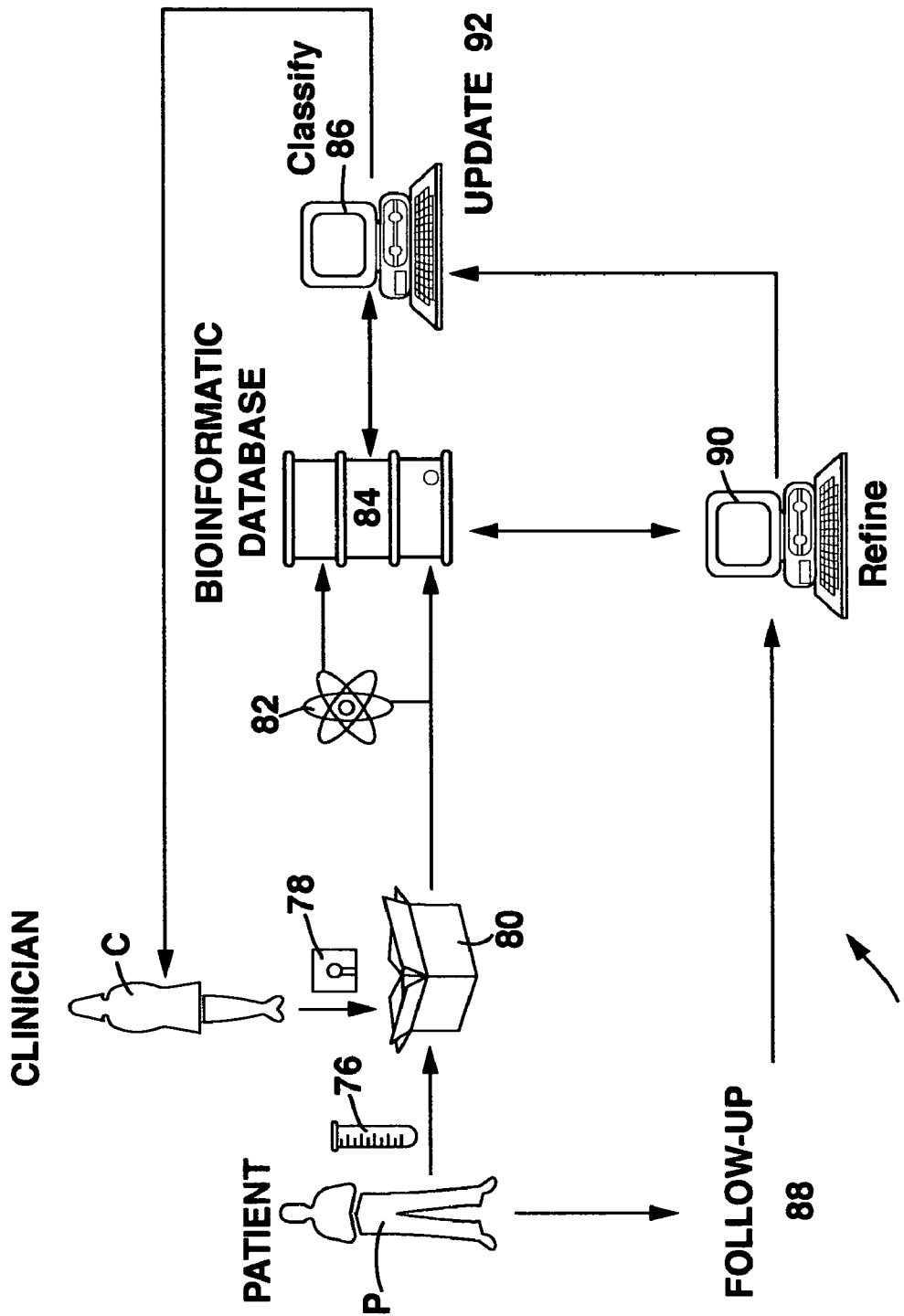
FIG. 4 is a conceptual diagram of a representative embodiment of the present invention.

Diagnostic Process (FIG. 4)

FIG. 4 is a conceptual diagram showing diagnostic process 74, which identifies patients at high risk for "Heart Condition" that would benefit from an implantable medical device (IMD). Diagnostic process 74 may also be used, for example, to provide an overall risk assessment or risk stratification, which indicates whether a patient is more likely to suffer from certain diseases or conditions over other diseases or conditions. Examples of other settings where diagnostic process 74 may be used include a pathology setting at a hospital or veterinary clinic, a research setting, or in any situation where biological specimens are classified. Process 74 includes patient P, clinician C, sample 76, medical information 78, delivery step 80, processing lab 82, bioinformatic database 84, classification step 86, follow-up step 88, refining step 90, and updating step 92.

In operation, patient P provides biological sample 76. Sample 76 may be any one or more of a variety of biological samples, which include blood, saliva, bodily fluids, cheek swabs, tissue samples or biopsies, microorganisms, etc. Clinician C provides medical information 78, which relates to patient P. Medical information 78 may include electronic information such as medical device interrogation data. This type of data may come from an IMD, a blood glucose monitor, an ultrasound machine, a magnetic resonance imaging machine, a CT scanner, electronic home monitoring systems (e.g. CareLink™), an external ECG monitor, or electronic medical records of clinical centers and IMD interrogation databases (e.g. PaceArt™). Medical information 78 may also include physiological measurements such as ejection fraction, organ dimensions, blood pressure, renal output, data from external, trancutaeous, or indwelling sensors, etc. Other relevant information includes demographic information, medical history including psychiatric conditions, family history, reported symptoms, and past and current diagnoses and treatments (pathological).

At delivery step 80, sample 76 is brought to processing lab 82 where proteomic, genomic, and lipidomic information is extracted from sample 76 through any of a variety of ways. For example, protein analysis may include gel electrophoresis, mass spectrometry, Enzyme-Linked ImmunoSorbent Assay (ELISA), etc. Genetic analysis may include the detection of insertions and deletions, microsatellites (stretches of DNA that consist of tandem repeats of a simple sequence of nucleotides, e.g., AAT repeated 15 times in succession) detection, detection of major rearrangements in the genome, single nucleotide polymorphism (SNP) detection, haplotyping, sequence analysis, restriction fragment length polymorphism (RFLP) detection, randomly amplified polymorphic DNA (RAPD) detection, amplified fragment length polymorphism (AFLP) detection, etc. Lipid analysis may include nuclear magnetic resonance (NMR) spectroscopy, electrospray mass spectroscopy (EMS), colorimetry, fluorimetry, gas chromatography, high performance liquid chromatography (HPLC), etc.

After all the molecular data is extracted from sample 76, a digital processor preferably enters the molecular data as well as medical information 78 into bioinformatic database 84. Bioinformatic database 84 houses all of the gathered information and data regarding patient P.

At classification step 86, patient P's information and data are analyzed and an algorithm is used to classify patient P based on class identifiers. The class identifiers may also be referred to as disease identifiers or disease markers. That information is then made accessible to clinician C. Depending on the type of service that is provided and the reason for patient P's enrollment, patient P's classification may take many forms. Here, patient P is being classified as benefiting or not benefiting from an IMD. At this point, patient P's classification may or may not be stored in bioinformatic database 84. The means for adding the classification to database 84 is preferably a processor.

Once a course of action is implemented for patient P based on the classification, patient P is followed as represented by follow-up step 88. Each time patient P returns for a follow-up visit with clinician C, updated information and data is gathered. The means of gathering follow-up data and information can be any medically accepted technique. So for example, patient P is classified as being at risk for Heart Condition and further classified as benefiting from an IMD. At a follow-up visit, data gathered from the IMD, including the operational history of the IMD, indicated that the IMD was never triggered even though the data also showed that patient P would have benefited from it. Thus, patient P should not be included in the class of patients that benefit from an IMD.

At refining step 90, patient P's classification is corrected based on the follow-up data and entered in bioinformatic database 84. If patient P's initial classification was entered into database 84, then patient P is reclassified. The means for reclassifying patient P is preferably a processor. The updated bioinformatic database 84 is used to refine class identifiers as described previously.

Lastly, at updating step 92, any new class identifiers, dropped class identifiers, and modified thresholds are updated for implementing classification step 86. Updating step 92 is preferably carried out with an algorithm run on a processor. Thus, diagnostic process 74 improves itself not only by adding patient information and data to bioinformatic database 84, but also by correcting any incorrect classifications.

Specimen Profile

Table 1, shown below, is an example of the data storage format, or specimen/patient profile, entered into bioinformatic database 84 for each patient. The profile is not limited by the type of information and data that it contains. Any information and data gathered from a specimen may be contained in the profile. Here, it is simplified for ease of discussion and illustration.

TABLE 1

PATENT ID

| COLUMN 1 FIXED INFO | COLUMN 2 DATE 1 | COLUMN 3 DATE 2 | COLUMN 4 DATE 3 |
|---|---|---|---|
|  | PHYSIOLOGICAL DATA | PHYSIOLOGICAL DATA | PHYSIOLOGICAL DATA |
| Sex | WEIGHT | WEIGHT | WEIGHT |
| Date of Birth | HEIGHT | HEIGHT | HEIGHT |
| Race | Body Mass Index | Body Mass Index | Body Mass Index |
|  | Ejection Fraction | Ejection Fraction | Ejection Fraction |
|  | EGM | EGM | EGM |
|  | Q-T interval | Q-T interval | Q-T interval |
| SNP 1 | Hemoglobin Count | Hemoglobin Count | Hemoglobin Count |
| SNP 2 | T-wave alternans | T-wave alternans | T-wave alternans |
| SNP 3 | Smoking | Smoking | Smoking |
| SNP 4 | CABG | CABG | CABG |
| SNP 5 | Stents | Stents | Stents |
| SNP 6 | Alcohol Consumption | Alcohol Consumption | Alcohol Consumption |
|  | PATHOLOGICAL DATA | PATHOLOGICAL DATA | PATHOLOGICAL DATA |
|  | Diabetes | Diabetes | Diabetes |
|  | Myocardial Infarct. | Myocardial Infarct. | Myocardial Infarct. |
|  | Arrhythmias | Arrhythmias | Arrhythmias |
|  | NYHC | NYHC | NYHC |
|  | Deafness | Deafness | Deafness |
|  | Drugs | Drugs | Drugs |
|  | MOLECULAR DATA | MOLECULAR DATA | MOLECULAR DATA |
|  | ProteinSpectrum 1 | ProteinSpectrum 1 | ProteinSpectrum 1 |
|  | ProteinSpectrum 2 | ProteinSpectrum 2 | ProteinSpectrum 2 |
|  | ProteinSpectrum 3 | ProteinSpectrum 3 | ProteinSpectrum 3 |
|  | Lipid Spectrum | Lipid Spectrum | Lipid Spectrum |
|  | Protein 1 | Protein 1 | Protein 1 |
|  | Protein 2 | Protein 2 | Protein 2 |
|  | Protein 3 | Protein 3 | Protein 3 |
|  | FAMILY HISTORY | FAMILY HISTORY | FAMILY HISTORY |

Column 1 contains fixed information that will not change over time and is gathered upon patient P's enrollment in diagnostic process 74. In Table 1, this includes patient P's sex, date of birth, race, and genetic information. The genetic information is also considered molecular data, but it will not change over time. However, new genetic information can be added over time as it is proven to be relevant. Examples listed in Table 1 include SNP 1-6.

Columns 2, 3, and 4 contain data that may change over time and, therefore, is periodically gathered from patient P. The data contained in these columns is divided into four categories: physiological data, pathological data, molecular data, and family history. Examples of physiological data are shown in Table 1 and include weight, height, body mass index, ejection fraction, EGM data, Q-T interval, hemoglobin count, T-wave alternans, smoking habits, number of coronary artery bypass grafts (CABG), stents, and alcohol consumption. Next, examples of pathological data are listed and include the presence of any diseases or conditions such as diabetes, myocardial infarction, arrhythmias, New York Heart Classification (NYHC), deafness, and drug regimens. Lastly, examples of listed molecular data include protein spectra 1-3, a lipid spectrum, and proteins 1-3. The lists in Table 1 are intended to be examples, and the specific data that is gathered and listed will depend on the purpose for the classification. For diagnostic process 74, EGM data is collected, which is stored in the memory of patient P's IMD. One way to obtain the IMD data is through telemetry from the IMD to a portable unit at the site of patient P. The data, in its entirety or in compressed form, can be subsequently transferred directly or indirectly to bioinformatic database 84 using any of a number of data transmission techniques. This data set might contain, but is not limited to, intracardiac electrogram data; pseudo-ECG data; histograms for heart rate, physical activity, minute volume, and pacing activity; intracardiac blood pressure data; transthoracic impedance (lung wetness) data; patient activation data; data on stimulation thresholds and trends; lead tip accelerometer data; and venous blood oxygen saturation data. The data is stored in its entirety and can be processed to extract further relevant data including, but not limited to, heart rate variability, QRS width, QT interval measurements, frequency of ventricular defibrillation shocks, duration and frequency of atrial fibrillation, atrial fibrillation burden, and correlation between syncopic episodes and heart rate drop. All of this data is added into patient P's profile.

Data generated in column 2 is gathered upon patient P's enrollment in the diagnostic service. Data generated in columns 3 and 4 is gathered with each subsequent follow-up visit to clinician C or whenever subsequent biological samples are obtained from patient P. Though only columns 3 and 4 are shown representing follow-up data of patient P, the number of columns of follow-up data is infinite. In addition, because a patient's medical information and data may be incomplete or contain contradictions, diagnostic process 74 is designed to compensate for these problems should they occur.

Figure 5:
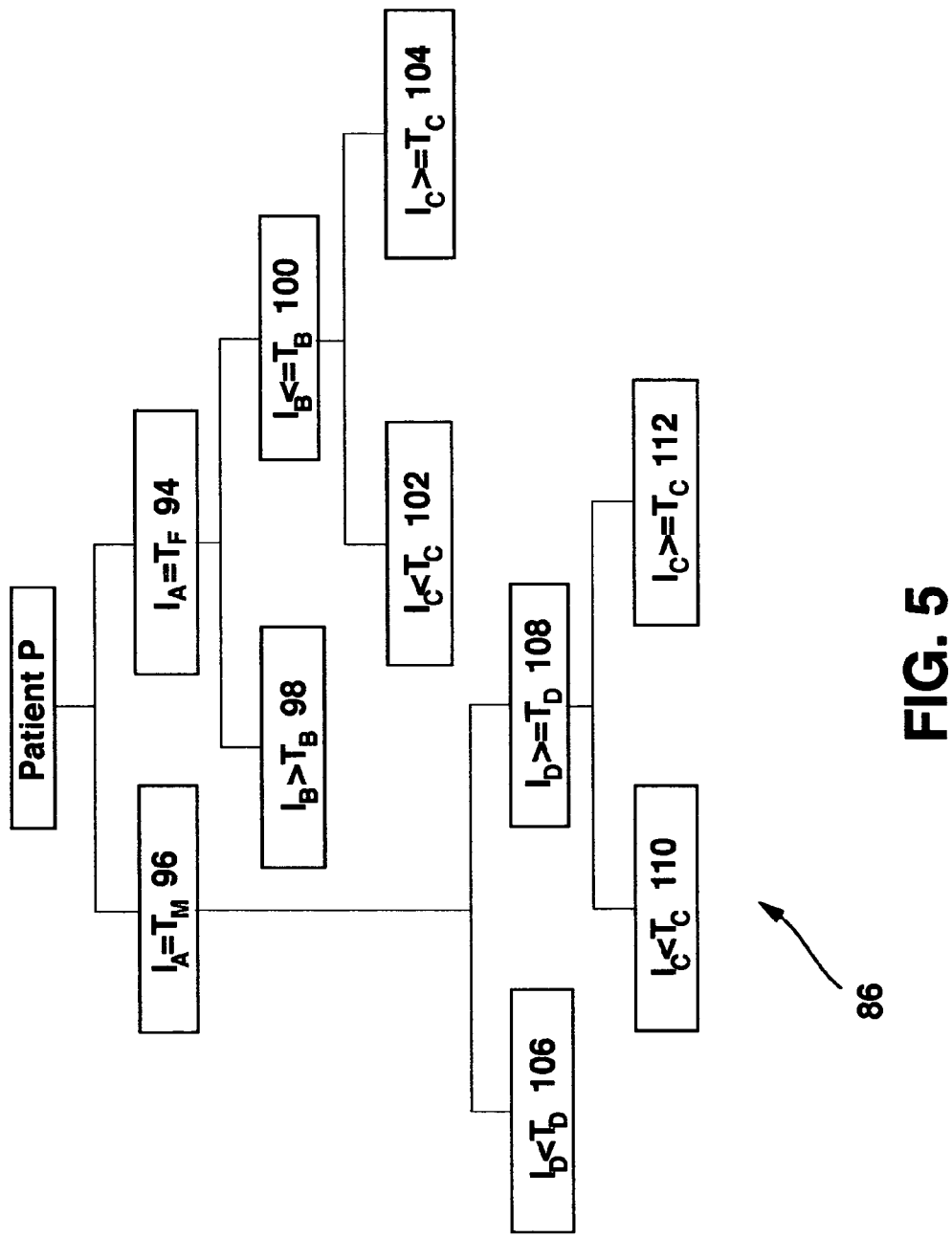
FIG. 5 is a logical diagram of a representative classification algorithm.

Classification Step (FIG. 5)

After the initial data is gathered upon patient P's enrollment and a profile generated, the profile is analyzed to classify patient P at classification step 86. FIG. 5 illustrates a representative, hypothetical diagnostic algorithm to carry out classification step 86, which classifies patient P as to his/her risk for Heart Condition. Classification is based on four class identifiers: $I_A$, $I_B$, $I_C$, and $I_D$. Class identifiers $I_A$-$I_D$ may be derived from any of the medical information and data included in patient P's profile. For instance, class identifier $I_A$ may be based on sex, $I_B$ may be based on ejection fraction, and $I_C$ and $I_D$ may be based on levels of protein 1 and protein 2, respectively. The values or data provided by patient P's profile are compared to threshold values, $T_{F/M}$, $T_B$, $T_C$, and $T_D$, determined for each class identifier, respectively.

First, the sex of patient P is determined from the profile. If patient P is female ($T_F$), patient P is placed into group 94. If patient P is male ($T_M$), patient P is placed into group 96. Placement in either group 94 or group 96 requires further testing to determine whether or not patient P is at risk for Heart Condition, but the testing occurs along different paths.

Upon placement into group 94, the value of patient P's ejection fraction measurements is compared to $T_B$. If the value is greater than $T_B$, patient P is placed into group 98 and classified as not at risk for Heart Condition. If, however, the value is less than or equal to $T_B$, patient P is placed into group 100 and is evaluated further.

Lastly, upon placement into group 100, the value of patient P's protein 1 level is compared to $T_C$. If the value is less than $T_C$, patient P is placed into group 102 and classified as not at risk for Heart Condition. If the value is greater than or equal to $T_C$, patient P is placed into group 104 and classified as at risk for Heart Condition.

If patient P is initially placed into group 96 based on sex, then the value of patient P's protein 2 level is compared to $T_D$. If the value is less than $T_D$, patient P is placed into group 106 and classified as not at risk for Heart Condition. If the value is greater than or equal to $T_D$, patient P is placed into group 108, and further evaluation is performed.

Lastly, upon placement into group 108, the value of patient P's protein 1 level is compared to $T_C$. If the value is less than $T_C$, patient P is placed into group 110 and classified as not at risk for Heart Condition. However, if the value is greater than or equal to $T_C$, patient P is placed into group 112 and classified as at risk for Heart Condition.

The process outlined in FIG. 5 is one way of classifying—where each class identifier is evaluated individually, and the patient is placed in a group before continuing on to the next class identifier. Alternatively, classification may be performed as a logical test such as an IF-THEN test. IF-THEN logic is implemented as follows:

IF
  (($P_A=T_F$) AND ($P_B \geq T_B$) AND ($P_C \geq T_C$)) OR (($P_A=T_M$) AND ($P_D \geq T_D$) AND ($P_C \geq T_C$))
THEN
  PATIENT P IS AT RISK FOR HEART CONDITION where $P_x$ represents information or values obtained from patient P's profile. The sensitivity and specificity of classification step 86 are preferably at least about 70%.

Thresholds T of class identifiers I are determined through clinical studies, experience, or the present invention, as previously described. Threshold T differs for each class identifier I. A patient may be classified as belonging to a specific class when the patient's values are above threshold T for some class identifiers I and below threshold T for other class identifiers I.

Example 1

Classification process 10 may also be utilized to identify class identifiers of a given condition. A representative clinical study to discover class identifiers is described here. Patients with coronary artery disease and meeting specific inclusion criteria were enrolled in the study. The patients were divided into two groups. The test group consisted of sixteen patients with an IMD and one sustained episode of ventricular tachyarrhythmia/ventricular fibrillation (VT/VF) with a cycle length less than or equal to 400 ms. The control group consisted of 32 patients that had no IMD and no known history of VT/VF.

Upon enrollment, each patient filled out an extensive questionnaire including medical information. Three blood samples were drawn from each patient, of which one was used for serum preparation. The serum samples were analyzed for proteomic, genomic, and lipidomic data. The results of the proteomic and genomic analysis will be discussed here.

Currently, there are numerous ways to detect differential concentrations or levels of a protein from various biological specimens. 2-D PAGE separation, such as Fluorescence 2-D Difference Gel Electrophoresis (DIGE), may be utilized to detect differences in protein levels between biological samples. In DIGE, up to three protein extracts are labeled with different fluorescent dyes, then combined and separated by 2-D PAGE. Images of the gel are captured at excitation wavelengths of each of the fluorescent labels, and the images are merged. The differences, which indicate differences in relative protein levels, between the protein extracts are detected by image analysis software.

Isotope-coded affinity tagging (ICAT™) uses stable isotope labeling to quantitatively analyze paired protein extracts. The proteins are then separated and identified by liquid chromatography and mass spectrometry. The isotope tags covalently bind to cysteine residues within a protein. Two different protein samples are labeled with two different tags that are identical except that one exists in a light isotopic form and the other in a heavy isotopic form. When bound to the same protein from different extracts, a definite mass change is detected through mass spectrometry. The relative abundance of protein pairs are determined to find pairs whose level is significantly different between the protein extracts.

Surface-enhanced laser desorption ionization-time of flight (SELDI-TOF) utilizes stainless steel or aluminum-based supports, or chips, having chemical (e.g. hydrophilic, hydrophobic, pre-activated, normal-phase, immobilized metal affinity, and cationic or anionic) or biological (e.g. antibody, antigen binding fragments, nucleic acid, enzyme, or receptor) bait surfaces that are 1-2 mm in diameter. These bait surfaces allow differential capture of proteins based on the intrinsic properties of the proteins themselves. Solubilized specimen samples are directly applied to the surface. Proteins with affinities to the bait surfaces bind, and unbound and weakly bound proteins are removed. The bound proteins are laser desorbed and ionized for analysis by mass spectrometry. The mass of the proteins are calculated based upon time-of-flight. Patterns of protein masses are produced that result in protein spectrums unique to each sample. Proteins that differ between samples are subsequently identified.

Matrix-assisted laser desorption ionization-time of flight (MALDI-TOF) is similar to SELDI-TOF except that protein samples are embedded in a crystal of matrix molecules that absorb at the laser wavelength. The energy absorption ionizes the proteins, and the mass is calculated based on time-of-flight resulting in protein spectrums.

Other methods may be employed to determine the relative level of proteins. For instance, the invention may be carried out by assaying individual protein markers with an ELISA. Protein arrays are a proteomic tool that is similar to DNA microarray technology. Protein-based chips array proteins on a small surface, and protein levels in specimens are measured directly using fluorescence-based imaging. Proteins are arrayed either on flat solid surfaces or in capillary systems called microfluidic arrays. Several different proteins can be applied to the arrays, with most of the current ones relying on antibody-antigen interactions.

These methods are presented only as examples. Any type of protein analysis may be used with the present invention. For instance, the relative abundance of proteins can also be measured indirectly by analysis of mRNA expressed in cells. DNA microarrays work by exploiting the ability of a given mRNA to specifically bind to the DNA template from which it originated. By using arrays with many DNA samples, the expression levels of hundreds or thousands of genes can be determined in a single experiment.

In the representative clinical study, proteins in the serum were initially fractionated into four groups based on the isoelectric point of the protein. The proteins were spotted onto three surfaces of one or more biochips. One surface was a weak cation exchange surface. Another surface was a hydrophobic surface. The last surface was an immobilized metal affinity surface. A protein spectrum fingerprint was obtained using SELDI-TOF.

Figure 6:
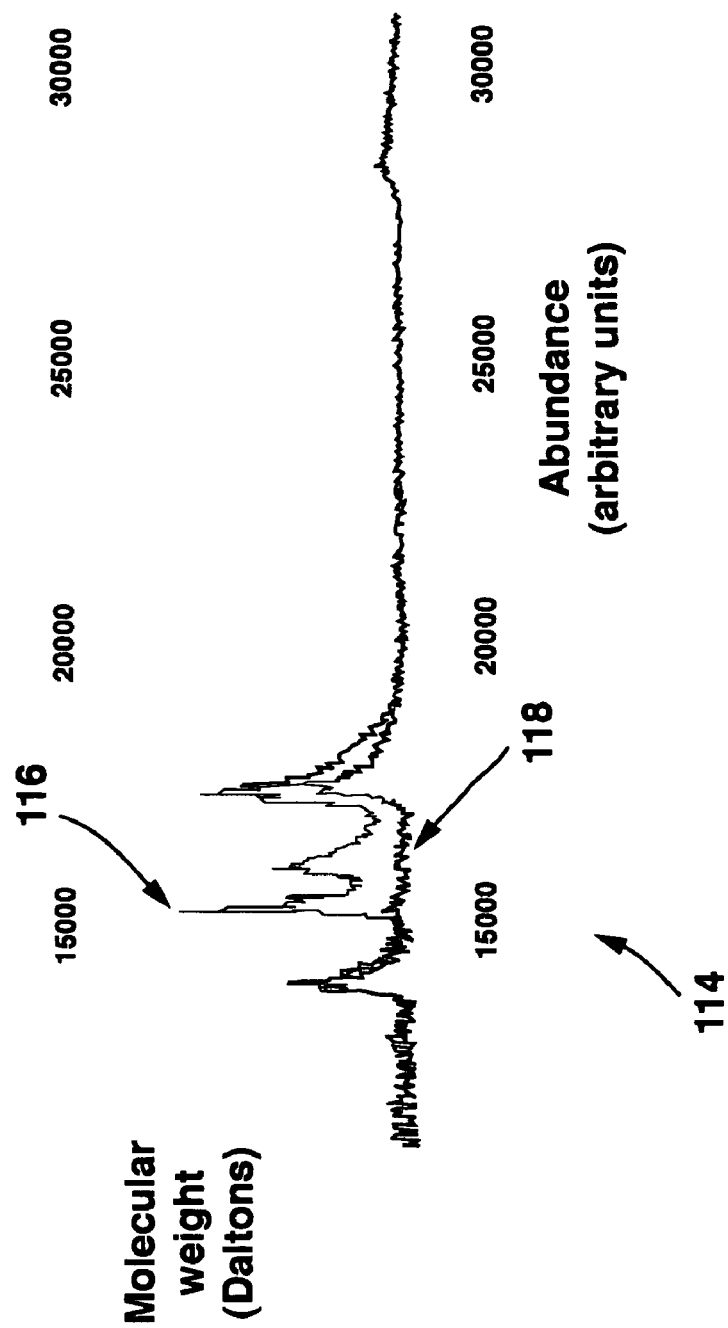
FIG. 6 is a graph showing protein spectra.

FIG. 6 shows sample protein spectra 114. Protein spectra 114 includes protein spectra 116 and 118. Protein spectrum 116 originates from a patient in the test group, and protein spectrum 118 originates from a patient in the control group. Differences between protein spectra 116 and 118 indicate differences in the level of expression of proteins between the two samples. This was indicative of all the protein spectra obtained from all patients in the study showing potential class identifiers that, in the present case, are protein markers. The differences in the protein markers between the two groups may form a basis for distinguishing patients that would benefit from an IMD versus patients that would not benefit from an IMD.

Figure 7:
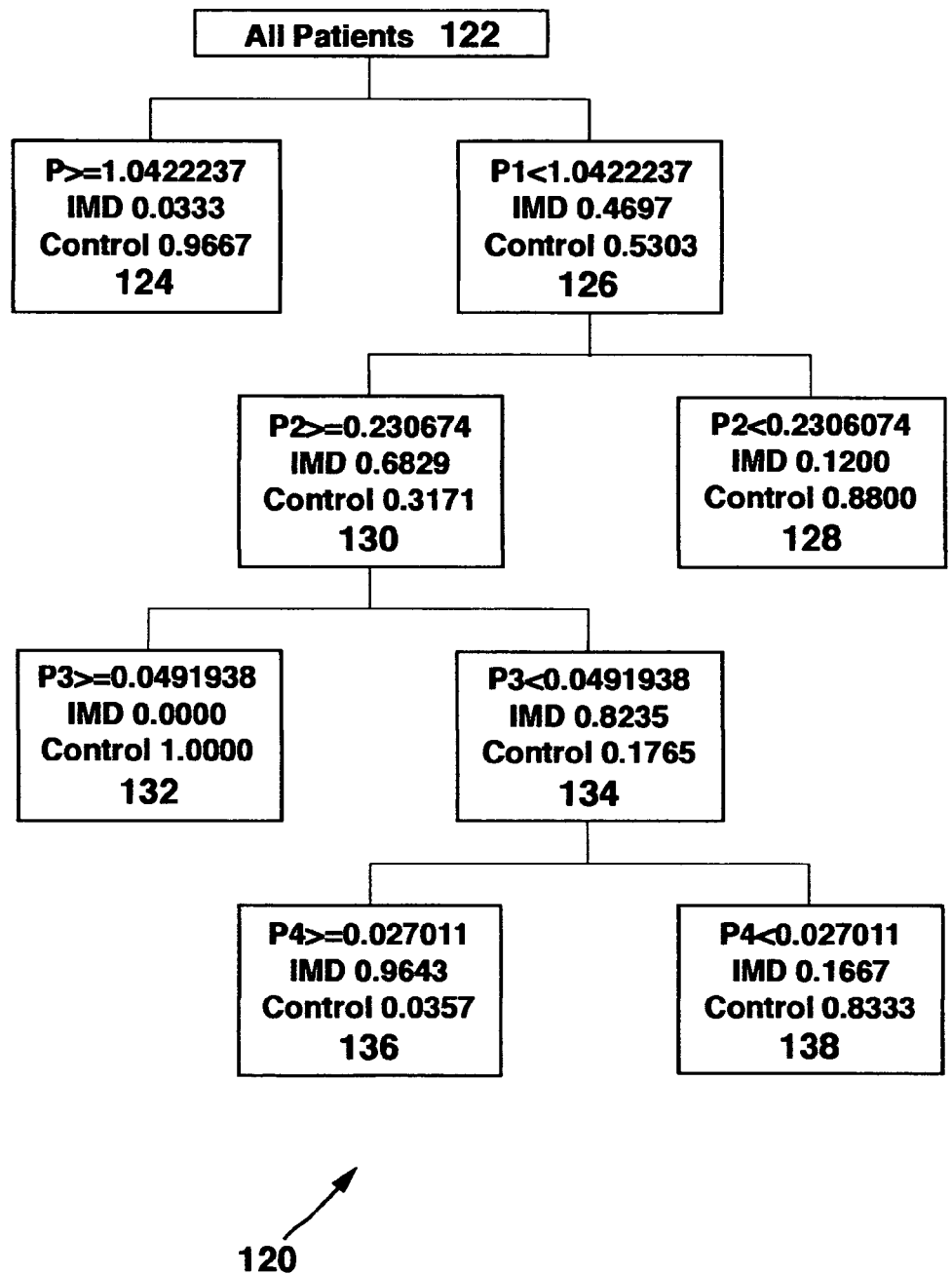
FIG. 7 is logical diagram illustrating a technique for identifying class identifiers.

FIG. 7 shows tree analysis 120. Tree analysis 120 applies the above results that identified candidate class identifiers, P1, P2, P3, and P4, to classify patients based on a high propensity for fatal VT/VF.

The serum levels of protein P1 were determined for all patients, represented as group 122. Patients having levels greater than or equal to 1.0422237 (measured in arbitrary units) were classified as not at significant risk for VT and, therefore, not a candidate for an IMD and placed into group 124. Patients having P1 levels less than 1.0422237 were placed into group 126 and were further evaluated.

P2 serum levels were next tested for patients in group 126. Patients having levels less than 0.2306074 were not candidates for an IMD and placed into group 128. Patients having levels greater than or equal to 0.2306074 were placed into group 130 and evaluated further.

P3 serum levels were then tested for patients in group 130. Patients having levels greater than or equal to 0.0491938 were not candidates for an IMD and placed in group 132. Patients having levels less than 0.0491938 were placed into group 134 and evaluated further.

Lastly, P4 serum levels were tested for patients in group 134. Patients having levels greater than or equal to 0.27011 were classified as being candidates for an IMD and placed in group 136. Patients having levels less than 0.27011 were not candidates and placed into group 138.

The arbitrary units may be normalized to an abundant protein, such as albumin. The invention also supports using other benchmarks, such as the total ion current in the mass spectrometer or calibration using a known concentration of an exogenous protein introduced into the sample, to measure protein levels.

The four markers, or class identifiers, correctly classified the 48 patients. Specifics of these proteins are shown in Table 2 below:

TABLE 2

| Protein Number | Molecular Weight (Da) | Isoelectric pH (pI) | Capture Surface |
|---|---|---|---|
| P1 | 10,146.5 | 9+ | Weak cation exchange |
| P2 | 15,006 | 9+ | Weak cation exchange |
| P3 | 166,582 | 5-7 | Weak cation exchange |
| P4 | 10,948 | 9+ | Immobilized metal affinity |

The proteins in Table 2 are characterized by their molecular weight and isoelectric point. It is not necessary to the invention that the proteins, or any class identifier, be specifically identified further.

Tree analysis 120 of FIG. 7 was expressed as an IF-THEN test and applied to clinical data where two biological samples from patients were processed. The results are shown in Table 3 below:

TABLE 3

|  | VT/VF | NORMAL |
|---|---|---|
| TEST (+) | 27 | 1 |
| TEST (−) | 5 | 63 |

Sensitivity: $(27/(27+5))\times 100=84\%$
Specificity: $(63/63+1))\times 100=98\%$
False Positives: $(1/(1+27))\times 100=4\%$
False Negatives: $(5/(5+63))\times 100=7\%$ The sensitivity and specificity of conventional classification techniques, such as signal averaged electrocardiogram, tend to be approximately 55% to 75%. Thus, this data demonstrates a significant improvement in sensitivity and specificity.

Next, Tree analysis 120 of FIG. 7 was utilized in an artificial neural network and applied to the same clinical data. The artificial neural network had four input nodes corresponding to proteins P1-P4. The network included four hidden nodes and one output node. The results are shown in Table 4 below:

TABLE 4

|  | VT/VF | NORMAL |
|---|---|---|
| TEST (+) | 24 | 1 |
| TEST (−) | 8 | 63 |

Sensitivity: $(24/(24+8))\times 100=75\%$
Specificity: $(63/(63+1))\times 100=98\%$
False Positives: $(1/(1+25))\times 100=4\%$
False Negatives: $(8/(8+63))\times 100=11\%$ Patients whose classification resulted in false positives and false negatives, as shown in Tables 3 and 4, are subsequently reclassified to further refine the class identifiers.

Depending on the type of class identifier, measurements of mass, concentration, levels, or abundance may be less important than simply determining if the class identifier is present or not. In other cases, the level detected on a single occasion is not important. Instead, the threshold is based on an increase or decrease in the levels or the rate of change, as demonstrated by two or more measurements separated by a specific time interval.

Genomic analysis was also carried out using patients participating in the same study. In this case, SNP rs1009531 was identified as a class identifier. SNP rs1009531 is located on gene KCND3, which codes for voltage-gated potassium channel, Shal-related family, member 3 (a.k.a. Kv4.3). Patients that are homozygous thymine/thymine have a 75% chance of experiencing a fatal arrhythmia, while patients that are homozygous cytosine/cytosine have only a 30% chance of experiencing a fatal arrhythmia. On the other hand, patients that are heterozygous thymine/cytosine have a 50% chance of experiencing a fatal arrhythmia. In this case, the partitioning method provided the best clustering of the patients for risk stratification.

Example 2

A second representative clinical study to discover class identifiers was carried out with an additional 30 patients. These additional patients also had coronary artery disease and met specific inclusion criteria. They were divided into the two groups based on whether or not patients had an IMD. The patients having an IMD also had at least one true VT/VF episode with a cycle length less than or equal to 400 ms terminated in the last 90 days. A total of 29 patients were in the test group, which consists of patients with an IMD, and 49 patients were in the control group.

Patients filled out an extensive questionnaire that included medical information that was then used in creating specimen profiles. Table 5 shows the patient characteristics included the specimen profile and the relative breakdown between the test and control groups.

TABLE 5

| Patient Characteristics | Patients in ICD Arm (N = 29) | Patients in Control Arm (N = 49) | Total Patients (N = 78) |
|---|---|---|---|
| Gender (N, %) | | | |
| Male | 29 (100%) | 49 (100%) | 78 (100%) |
| Female | 0 (0%) | 0 (0%) | 0 (0%) |
| Age (years) | | | |
| Mean | 68.8 | 67.1 | 67.8 |
| Standard Deviation | 8.2 | 8.1 | 8.1 |
| Minimum-Maximum | 50-81 | 51-81 | 50-81 |
| Left Ventricular Ejection Fraction | | | |
| Time since most recent LVEF (days) | | | |
| Mean | 1.1 | 0.9 | 1 |
| Standard Deviation | 1.1 | 1.1 | 1.1 |
| Minimum-Maximum | 0-5.3 | 0-4.8 | 0-5.3 |
| Most Recent Documented Measurement (%) | | | |
| Mean | 37.9 | 51.2 | 46.2 |
| Standard Deviation | 9.6 | 9.5 | 11.5 |
| Minimum-Maximum | 28-66 | 29-73 | 28-73 |
| Method of LVEF measurement | | | |
| Radionuclide angiocardiography/MUGA | 6 (21%) | 19 (39%) | 25 (32%) |
| Echo | 9 (31%) | 16 (33%) | 25 (32%) |
| Cath | 13 (45%) | 14 (29%) | 27 (35%) |
| Unknown | 0 (0%) | 0 (0%) | 0 (0%) |

Table 6 shows patient cardiovascular surgical and medical history that was included in the specimen profiles and the relative breakdown between the control and test groups.

TABLE 6

| Patient Characteristics | Patients in ICD Arm (N = 29) | Patients in Control Arm (N = 49) | Total Patients (N = 78) |
|---|---|---|---|
| Cardiovascular Surgical History (N, %) | | | |
| None | 6 (20.7%) | 4 (8.2%) | 10 (12.8%) |
| Coronary Artery Bypass Graft | 14 (48.3%) | 20 (40.8%) | 34 (43.6%) |
| Coronary Artery Intervention | 13 (44.8%) | 36 (73.5%) | 49 (62.8%) |
| Angioplasty | 8 (27.6%) | 25 (51%) | 33 (42.3%) |
| Stent | 7 (24.1%) | 31 (63.3%) | 38 (48.7%) |
| Atherectomy | 0 (0%) | 0 (0%) | 0 (0%) |
| Ablation | 3 (10.3%) | 3 (6.1%) | 6 (7.7%) |
| Valvular Surgery | 1 (3.4%) | 1 (2%) | 2 (2.6%) |
| Other | 1 (3.4%) | 2 (4.1%) | 3 (3.8%) |
| Cardiovascular Medical History | | | |
| None | 0 (0%) | 0 (0%) | 0 (0%) |
| Coronary Artery Disease | 29 (100%) | 49 (100%) | 78 (100%) |
| Myocardial Infarction | 29 (100%) | 49 (100%) | 78 (100%) |
| Number of infarctions | | | |
| Mean | 1.4 | 1.3 | 1.3 |
| Standard Deviation | 0.6 | 0.5 | 0.5 |
| Minimum-Maximum | 1-3 | 1-3 | 1-3 |
| Time Since First Infarction (years) | | | |
| Mean | 10.2 | 6.6 | 7.9 |
| Standard Deviation | 7.7 | 5.6 | 6.6 |
| Minimum-Maximum | 1-26 | 0-22 | 0-26 |
| Time Since Most Recent Infarction (years) | | | |
| Mean | 5.3 | 5 | 5.1 |
| Standard Deviation | 5 | 5.4 | 5.2 |
| Minimum-Maximum | 1-17 | 0-22 | 0-22 |
| Hypertension | 19 (65.5%) | 34 (69.4%) | 53 (67.9%) |
| Cardiomyopathy | 18 (62.1%) | 3 (6.1%) | 21 (26.9%) |
| Hypertrophic | 5 (17.2%) | 0 (0%) | 5 (6.4%) |
| Dilated | 9 (31%) | 3 (6.1%) | 12 (15.4%) |
| Valve Disease/Disorder | 4 (13.8%) | 8 (16.3%) | 12 (15.4%) |
| Aortic | 0 (0%) | 5 (10.2%) | 5 (6.4%) |
| Tricuspid | 1 (3.4%) | 1 (2%) | 2 (2.6%) |
| Mitral | 4 (13.8%) | 3 (6.1%) | 7 (9%) |
| Pulmonary | 0 (0%) | 0 (0%) | 0 (0%) |
| Primary/Idiopathic Electrical Conduction Disease | 0 (0%) | 1 (2%) | 1 (1.3%) |
| Documented Accessory Pathway | 0 (0%) | 0 (0%) | 0 (0%) |
| Chronotropic Incompetence | 1 (3.4%) | 0 (0%) | 1 (1.3%) |
| NYHA Classification | | | |
| Class I | 4 (13.8%) | 3 (6.1%) | 7 (9%) |
| Class II | 6 (20.7%) | 5 (10.2%) | 11 (14.1%) |
| Class III | 4 (13.8%) | 0 (0%) | 4 (5.1%) |
| Class IV | 0 (0%) | 0 (0%) | 0 (0%) |
| Not Classified | 15 (51.7%) | 41 (83.7%) | 56 (71.8%) |
| Congenital Heart Disease | 0 (0%) | 0 (0%) | 0 (0%) |
| Other | 2 (6.9%) | 3 (6.1%) | 5 (6.4%) |

Table 7 shows patient arrhythmia history that was included in the specimen profiles and the relative breakdown between the control and test groups.

TABLE 7

| Patient Characteristics | Patients in ICD Arm (N = 29) | Patients in Control Arm (N = 49) | Total Patients (N = 78) |
|---|---|---|---|
| Spontaneous Arrhythmia History (N, %) | | | |
| None | 0 (0%) | 26 (53.1%) | 26 (33.3%) |

TABLE 7-continued

| Patient Characteristics | Patients in ICD Arm (N = 29) | Patients in Control Arm (N = 49) | Total Patients (N = 78) |
|---|---|---|---|
| Ventricular | | | |
| Sustained Monomorphic VT | 23 (79.3%) | 0 (0%) | 23 (29.5%) |
| Sustained Polymorphic VT | 1 (3.4%) | 0 (0%) | 1 (1.3%) |
| Nonsustained VT | 17 (58.6%) | 0 (0%) | 17 (21.8%) |
| Ventricular Flutter | 1 (3.4%) | 0 (0%) | 1 (1.3%) |
| Ventricular Fibrillation | 9 (31%) | 0 (0%) | 9 (11.5%) |
| Torsades de Pointes | 0 (0%) | 0 (0%) | 0 (0%) |
| Long Q/T Syndrome | 0 (0%) | 0 (0%) | 0 (0%) |
| Other | 0 (0%) | 2 (4.1%) | 2 (2.6%) |
| Bradyarrythmias/Conduction Disturbances | | | |
| Sinus Bradycardia | 5 (17.2%) | 14 (28.6%) | 19 (24.4%) |
| Sick Sinus Syndrome | 0 (0%) | 2 (4.1%) | 2 (2.6%) |
| 1° AV Block | 7 (24.1%) | 6 (12.2%) | 13 (16.7%) |
| 2° AV Block | 0 (0%) | 0 (0%) | 0 (0%) |
| Type I (Mobitz) | 0 (0%) | 0 (0%) | 0 (0%) |
| Type II (Wenckebach) | 0 (0%) | 0 (0%) | 0 (0%) |
| 3° AV Block | 0 (0%) | 0 (0%) | 0 (0%) |
| Right Bundle Branch Block | 5 (17.2%) | 8 (16.3%) | 13 (16.7%) |
| Left Bundle Branch Block | 4 (13.8%) | 2 (4.1%) | 6 (7.7%) |
| Bradycardia-Tachycardia Syndrome | 0 (0%) | 0 (0%) | 0 (0%) |
| Other | 2 (6.9%) | 0 (0%) | 2 (2.6%) |
| Atrial Arrythmia History (N, %) | | | |
| None | 14 (48.3%) | 36 (73.5%) | 50 (64.1%) |
| Atrial Tachycardia | 4 (13.8%) | 0 (0%) | 4 (5.1%) |
| Paroxysmal | 4 (13.8%) | 0 (0%) | 4 (5.1%) |
| Recurrent | 0 (0%) | 0 (0%) | 0 (0%) |
| Chronic | 0 (0%) | 0 (0%) | 0 (0%) |
| Atrial Flutter | 1 (3.4%) | 5 (10.2%) | 6 (7.7%) |
| Paroxysmal | 1 (3.4%) | 4 (8.2%) | 5 (6.4%) |
| Recurrent | 0 (0%) | 1 (2%) | 1 (1.3%) |
| Chronic | 0 (0%) | 0 (0%) | 0 (0%) |
| Atrial Fibrillation | 11 (37.9%) | 9 (18.4%) | 20 (25.6%) |
| Paroxysmal | 8 (27.6%) | 3 (6.1%) | 11 (14.1%) |
| Recurrent | 0 (0%) | 4 (8.2%) | 4 (5.1%) |
| Chronic | 3 (10.3%) | 1 (2%) | 4 (5.1%) |

Table 8 shows patient family history that was included in the specimen profiles and the relative breakdown between the control and test groups.

TABLE 8

| Patient Characteristics | Patients in ICD Arm (N = 29) | Patients in Control Arm (N = 49) | Total Patients (N = 78) |
|---|---|---|---|
| Patient Family History (N, %) | | | |
| None | 20 (69%) | 31 (63.3%) | 51 (65.4%) |
| Long Q/T Syndrome | 0 (0%) | 0 (0%) | 0 (0%) |
| Grandparent | 0 (0%) | 0 (0%) | 0 (0%) |
| Parent | 0 (0%) | 0 (0%) | 0 (0%) |
| Sibling | 0 (0%) | 0 (0%) | 0 (0%) |
| Cousin | 0 (0%) | 0 (0%) | 0 (0%) |
| Sudden Cardiac Death | 5 (17.2%) | 11 (22.4%) | 16 (20.5%) |
| Grandparent | 0 (0%) | 1 (2%) | 1 (1.3%) |
| Parent | 4 (13.8%) | 8 (16.3%) | 12 (15.4%) |
| Sibling | 1 (3.4%) | 3 (6.1%) | 4 (5.1%) |
| Cousin | 0 (0%) | 1 (2%) | 1 (1.3%) |
| Sudden Death | 3 (10.3%) | 4 (8.2%) | 7 (9%) |
| Grandparent | 0 (0%) | 0 (0%) | 0 (0%) |
| Parent | 3 (10.3%) | 3 (6.1%) | 6 (7.7%) |
| Sibling | 1 (3.4%) | 1 (2%) | 2 (2.6%) |
| Cousin | 0 (0%) | 0 (0%) | 0 (0%) |
| Syncope | 2 (6.9%) | 1 (2%) | 3 (3.8%) |
| Grandparent | 0 (0%) | 0 (0%) | 0 (0%) |
| Parent | 2 (6.9%) | 0 (0%) | 2 (2.6%) |
| Sibling | 0 (0%) | 1 (2%) | 1 (1.3%) |

TABLE 8-continued

| Patient Characteristics | Patients in ICD Arm (N = 29) | Patients in Control Arm (N = 49) | Total Patients (N = 78) |
|---|---|---|---|
| Cousin | 0 (0%) | 0 (0%) | 0 (0%) |
| Deafness | 1 (3.4%) | 4 (8.2%) | 5 (6.4%) |
| Grandparent | 0 (0%) | 1 (2%) | 1 (1.3%) |
| Parent | 1 (3.4%) | 2 (4.1%) | 3 (3.8%) |
| Sibling | 0 (0%) | 1 (2%) | 1 (1.3%) |
| Cousin | 0 (0%) | 0 (0%) | 0 (0%) |
| History of Thrombo-embolic Event | | | |
| No | 24 (82.8%) | 44 (89.8%) | 68 (87.2%) |
| Yes | 5 (17.2%) | 5 (10.2%) | 10 (12.8%) |
| Time since most recent event (years) | | | |
| Mean | 1.8 | 4.2 | 3.2 |
| Standard Deviation | 1.4 | 6.3 | 4.7 |
| Minimum-Maximum | 0.8-3.4 | 0.2-13.5 | 0.2-13.5 |
| Type | | | |
| TIA | 2 (6.9%) | 1 (2%) | 3 (3.8%) |
| CVA | 2 (6.9%) | 1 (2%) | 3 (3.8%) |
| PE | 0 (0%) | 1 (2%) | 1 (1.3%) |
| Renal | 0 (0%) | 0 (0%) | 0 (0%) |
| Peripheral | 0 (0%) | 0 (0%) | 0 (0%) |
| Other | 1 (3.4%) | 2 (4.1%) | 3 (3.8%) |
| Other History | | | |
| History of Hyperthyroidism | 0 (0%) | 2 (4.1%) | 2 (2.6%) |
| Hearing loss | 12 (41.4%) | 16 (32.7%) | 28 (35.9%) |

Table 9 shows patient lifestyle characteristics that were included in the specimen profiles and the relative breakdown between the control and test groups.

TABLE 9

| Patient Characteristics | Patients in ICD Arm (N = 29) | Patients in Control Arm (N = 49) | Total Patients (N = 78) |
|---|---|---|---|
| Does the Patient Smoke? | | | |
| No | 23 (79.3%) | 42 (85.7%) | 65 (83.3%) |
| Yes | 6 (20.7%) | 7 (14.3%) | 13 (16.7%) |
| Number of Years | | | |
| Mean | 41.6 | 39.6 | 40.4 |
| Standard Deviation | 11.1 | 8 | 9 |
| Minimum-Maximum | 30-55 | 30-50 | 30-55 |
| Degree of Smoking | | | |
| 1-2 packs a week | 1 (3.4%) | 2 (4.1%) | 3 (3.8%) |
| 3-5 packs a week | 0 (0%) | 1 (2%) | 1 (1.3%) |
| 5-10 packs a week | 2 (6.9%) | 3 (6.1%) | 5 (6.4%) |
| 10 or more packs a week | 1 (3.4%) | 0 (0%) | 1 (1.3%) |
| Use of Alcohol | | | |
| No | 17 (58.6%) | 24 (49%) | 41 (52.6%) |
| Yes | 12 (41.4%) | 25 (51%) | 37 (47.4%) |
| Number of Years | | | |
| Mean | 36.7 | 38.2 | 37.7 |
| Standard Deviation | 17 | 13.9 | 14.7 |
| Minimum-Maximum | 10-59 | 4-60 | 4-60 |
| Degree of Drinking | | | |
| 1-2 drinks a week | 5 (17.2%) | 6 (12.2%) | 11 (14.1%) |
| 3-5 drinks a week | 1 (3.4%) | 7 (14.3%) | 8 (10.3%) |
| 5-10 drinks a week | 4 (13.8%) | 6 (12.2%) | 10 (12.8%) |
| 10 or more drinks a week | 2 (6.9%) | 5 (10.2%) | 7 (9%) |

Table 10 shows patient baseline medications that were included in the specimen profiles and the relative breakdown between the control and test groups.

TABLE 10

| Patient Medications | Patients in ICD Arm (N = 29) | Patients in Control Arm (N = 49) | Total Patients (N = 78) |
|---|---|---|---|
| Any Medications in Prior 6 Months (N, %) | | | |
| No | 0 (0%) | 0 (0%) | 0 (0%) |
| Yes | 29 (100%) | 49 (100%) | 78 (100%) |
| Class I | 4 (13.8%) | 1 (2%) | 5 (6.4%) |
| Disopyramide | 0 (0%) | 0 (0%) | 0 (0%) |
| Flecainide | 0 (0%) | 0 (0%) | 0 (0%) |
| Mexiletine | 1 (3.4%) | 0 (0%) | 1 (1.3%) |
| Moricizine | 0 (0%) | 0 (0%) | 0 (0%) |
| Procainamide | 2 (6.9%) | 0 (0%) | 2 (2.6%) |
| Propafenone | 0 (0%) | 1 (2%) | 1 (1.3%) |
| Quinidine | 1 (3.4%) | 0 (0%) | 1 (1.3%) |
| Tocainide | 0 (0%) | 0 (0%) | 0 (0%) |
| Other | 0 (0%) | 0 (0%) | 0 (0%) |
| Class III | 14 (48.3%) | 4 (8.2%) | 18 (23.1%) |
| Amiodarone | 8 (27.6%) | 2 (4.1%) | 10 (12.8%) |
| Dofetilide | 0 (0%) | 0 (0%) | 0 (0%) |
| Sotalol | 7 (24.1%) | 2 (4.1%) | 9 (11.5%) |
| Other | 0 (0%) | 0 (0%) | 0 (0%) |
| Beta Blockers | 17 (58.6%) | 36 (73.5%) | 53 (67.9%) |
| Atenolol | 1 (3.4%) | 9 (18.4%) | 10 (12.8%) |
| Betaxolol | 0 (0%) | 0 (0%) | 0 (0%) |
| Bisoprolol | 0 (0%) | 0 (0%) | 0 (0%) |
| Bucindolol | 0 (0%) | 0 (0%) | 0 (0%) |
| Carvedilol | 4 (13.8%) | 3 (6.1%) | 7 (9%) |
| Metoprolol | 11 (37.9%) | 22 (44.9%) | 33 (42.3%) |
| Nadolol | 0 (0%) | 0 (0%) | 0 (0%) |
| Penbutolol | 0 (0%) | 0 (0%) | 0 (0%) |
| Propranolol | 1 (3.4%) | 2 (4.1%) | 3 (3.8%) |
| Timolol | 0 (0%) | 0 (0%) | 0 (0%) |
| Other | 0 (0%) | 1 (2%) | 1 (1.3%) |
| Calcium Channel Blockers | 4 (13.8%) | 10 (20.4%) | 14 (17.9%) |
| Amlodipine | 2 (6.9%) | 4 (8.2%) | 6 (7.7%) |
| Diltiazem | 0 (0%) | 3 (6.1%) | 3 (3.8%) |
| Ibepridil | 0 (0%) | 0 (0%) | 0 (0%) |
| Felodipine | 0 (0%) | 0 (0%) | 0 (0%) |
| Nifedipine | 0 (0%) | 3 (6.1%) | 3 (3.8%) |
| Nisoldipine | 0 (0%) | 0 (0%) | 0 (0%) |
| Nimodipine | 0 (0%) | 0 (0%) | 0 (0%) |
| Verapamil | 1 (3.4%) | 0 (0%) | 1 (1.3%) |
| Other | 1 (3.4%) | 0 (0%) | 1 (1.3%) |
| Digoxin | 9 (31%) | 3 (6.1%) | 12 (15.4%) |
| Anti-Coagulants | 28 (96.6%) | 46 (93.9%) | 74 (94.9%) |
| Warfarin | 5 (17.2%) | 8 (16.3%) | 13 (16.7%) |
| Aspirin | 25 (86.2%) | 40 (81.6%) | 65 (83.3%) |
| Other | 4 (13.8%) | 14 (28.6%) | 18 (23.1%) |
| Other | 26 (89.7%) | 39 (79.6%) | 65 (83.3%) |

Protein analysis from patient blood samples was carried out as described in the previous example. The CART (Classification and Regression Tree) method was used to identify class identifiers. The iterative partitioning algorithm used the test versus control groupings as the response variables and 2076 predictor variables that included 86 demographic variables and 1990 protein/peptide variables. Eligible protein/peptide variables were identified as peaks in spectral analyses of at least 4% of patients. Each patient's protein level for a given variable was averaged from two peak measurements.

Figure 8:
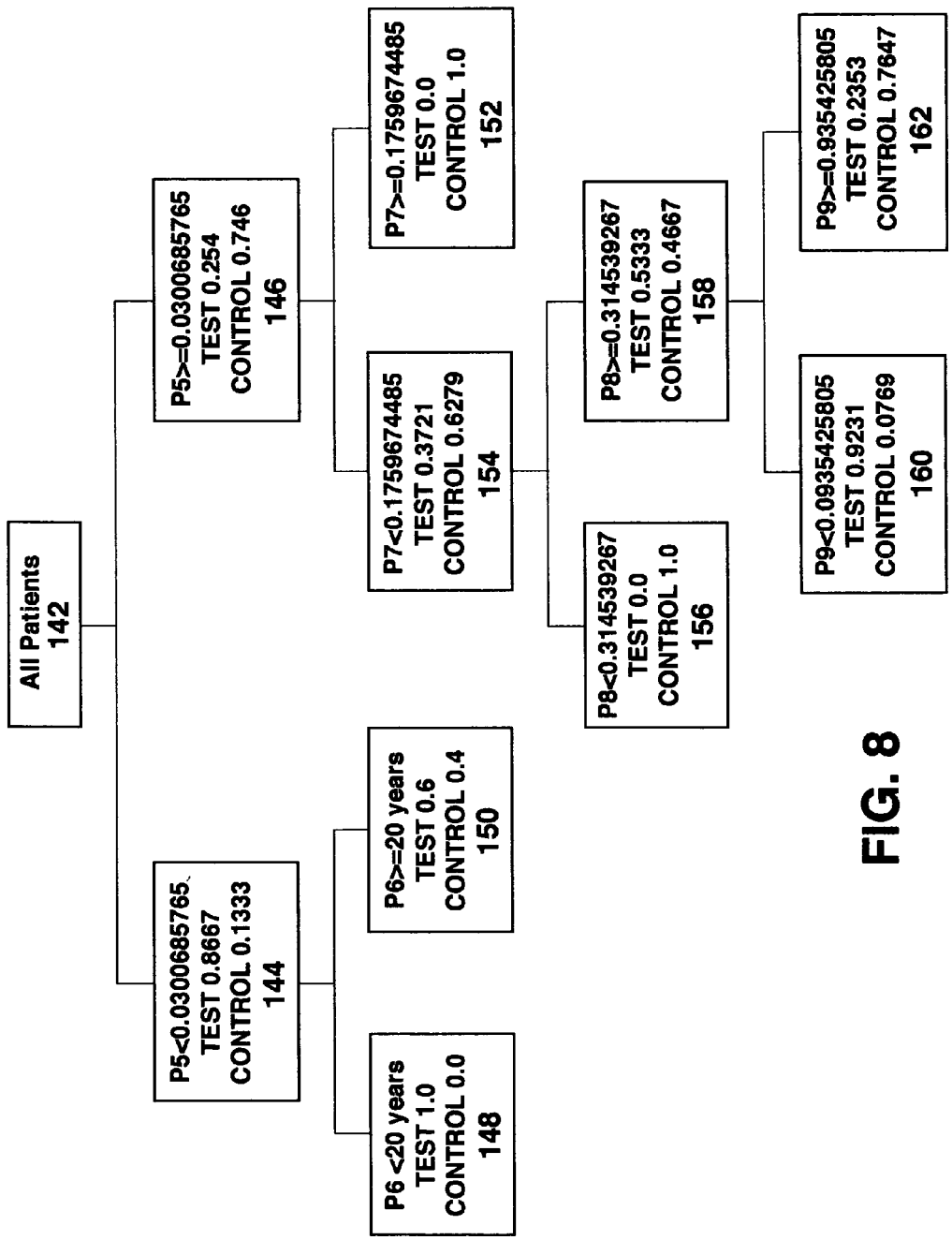
FIG. 8 is a logical diagram of a representative classification algorithm.

FIG. 8 is the resulting tree analysis from the CART analysis. Tree analysis 140 uses the five identified class identifiers, P5, P6, P7, P8, and P9, to classify all patients, represented as group 142, based on risk for fatal VT/VF.

The most effective class identifier is protein P5. Fifteen patients having P5 levels less than 0.0300685765 (measured in arbitrary units) were placed in group 144. Thirteen, or 86.7%, were test patients with IMDs. Sixty-three patients having P5 levels greater than or equal to 0.0300685765 were placed in group 146. Sixteen, or 25.4%, were test patients.

The class identifier shown to further partition group 144 and represented as P6 was consumption of alcohol or lack of consumption for less than 20 years. Ten patients (eight of which had never consumed alcohol) were placed in group 148. All 10 patients, or 100%, were test patients. Five patients that had consumed alcohol for more than 20 years were placed in group 150. Three of these five patients, or 60%, were test patients.

Group 146 was then further partitioned based on levels of protein P7. Twenty patients having P7 levels less than or equal to 0.1759674485 were placed in group 152. All 20, or 100%, were control patients. Forty-three patients having P7 levels greater than 0.1759674485 were placed in group 154. Twenty-seven of these 43 patients, or 62.8%, were control patients.

Group 154 was further partitioned based on levels of protein P8. Thirteen patients having P8 levels less than 0.314539267 were placed in group 156. All 13, or 100%, were control patients. Thirty patients having P8 levels greater than or equal to 0.314539267 were placed in group 158. Fourteen of these 30 patients, or 46.7%, were control patients.

Further partitioning of group 158 was based on levels of protein P9. Thirteen patients having P9 levels less than 0.0935425805 were placed into group 160. Twelve of these patients, or 92.3%, were test patients. Seventeen patients having P9 levels greater than or equal to 0.0935425805 were placed into group 162. Only four of these 17 patients, or 23.5%, were test patients.

Thus, when applying tree analysis 140, patients falling into groups 148 and 160 have a significant risk of experiencing VT/VF and would benefit from an IMD. Conversely, patients falling into groups 152, 156, and 162 do not have a significant risk of experiencing VT/VF.

Table 11 summarizes the percentage of test patients belonging to each group of tree analysis 140.

TABLE 11

| P5 | P6 | P7 | P8 | P9 | Col. 6 | Col. 7* |
|---|---|---|---|---|---|---|
| <0.0300685765 | Subtotal | | | | 15 | 86.7 |
| | ≧20 years | | | | 5 | 60 |
| | <20 years | | | | 10 | 100 |
| ≧0.0300685765 | N/A | Subtotal | | | 63 | 25.4 |
| | | ≧0.1759674485 | | | 20 | 0 |
| | | <0.1759674485 | Subtotal | | 43 | 37.2 |
| | | | <0.314539267 | | 13 | 0 |
| | | | ≧0.314539267 | Subtotal | 30 | 53.3 |
| | | | | ≧0.0935425805 | 17 | 23.5 |
| | | | | <0.0935425805 | 13 | 92.3 |
| | | | Total | | 78 | 37.2 |

*Each percentage is for the applicable group of the corresponding row; therefore, the percentages do not sum to 100%, as they are calculated with different denominators (patient sample sizes).

Columns one through five represent the class identifiers, P5-P9 and rows represent groups 144-162 obtained by using the class identifiers. Column 6 (Col. 6) is the total number of patients belonging to each corresponding group, and column 7 (Col. 7) is percentage of patients in each group that are test patients.

For example, to assess the percentage of test patients among all patients having P5 levels greater than or equal to 0.0300685765 and P7 levels less than 0.1759674485, begin at column 1 and select the row corresponding to ≧0.0300685765. Move to columns 2 and 3 (column 2 does not apply to these patients) and select the row in column 3 corresponding to <0.1759674485. Moving across to column 6, the number of patients having these class identifiers is 43, and the corresponding row in column 7 indicates that 37.2% of the 43 patients were test patients.

Table 12 is a summary of information regarding proteins P5, P7, P8, and P9.

TABLE 12

| Molecular Weight | Chip Type | Fraction of Isolation | Spectrum Range | Partitioning Peak Intensity | |
|---|---|---|---|---|---|
| P5 11991 | Immobilized Metal Affinity Surface | Combined fractions f2 and f3 containing pH 5-7 | High Protein | 0.0300685765 |
| P7 10552.4 | Weak Cation Exchange Surface | Fraction 1 containing flow-through and pH = 9 | High Protein | 0.1759674485 |
| P8 43529.4 | Weak Cation Exchange Surface | Fraction 1 containing flow-through and pH = 9 | High Protein | 0.314539267 |
| P9 13806.8 | Hydrophobic Surface | Fraction 1 containing flow-through and pH = 9 | Protein | 0.0935425805 |

This analysis resulted in four protein class identifiers and one demographic class identifier that correctly classifies patients based on risk of experiencing a true VT/VF episode.

A genetic analysis of the same group of patients identified additional class identifiers useful in predicting a patient's risk of experiencing VT/VF. DNA from each patient was extracted from cells in the blood samples. There were 162 gene SNPs (Single Nucleotide Polymorphisms) for which genotypes were obtained for the patients. In the discussion regarding genetics, the following abbreviations are used: a=adenine, t=thymine, c=cytosine, and g=guanine.

A chi-square test was performed using the response variable (test, control) and each of the 162 SNP variables. Table 13 lists SNPs and resulting p-values identified as corresponding to genotypes and patient groups that were not independent.

TABLE 13

| Gene SNP | # of Genotypes | P-value |
|---|---|---|
| rs2239507 | 3 | 0.0051 |
| rs7626962 | 2 | 0.0094* |
| rs3743496 | 3 | 0.012* |
| rs723672 | 6 | 0.0060* |
| rs2072715 | 2 | 0.0473* |
| rs12276475 | 3 | 0.0092* |
| rs1544503 | 3 | 0.0349* |
| rs3752158 | 3 | 0.0465* |

TABLE 13-continued

| Gene SNP | # of Genotypes | P-value |
|---|---|---|
| rs1023214 | 3 | 0.0322* |
| rs730818 | 3 | 0.0372 |
| rs1842082 | 3 | 0.0434 |
| rs7578438 | 5 | 0.0443* |
| rs545118 | 3 | 0.0415* |
| rs802351 | 5 | 0.0314* |

*Fisher's exact test used, as criteria for chi-square test not met

In some cases the expected cell counts were too small, and it was determined that the chi-square test was not reliable. Instead, Fisher's exact test was used. Fourteen SNPs produced p-values less than 0.05.

SNP rs2239507 is located at position chr12:5021395, Build 123, within the KCNA5 gene (Accession No. NT_009759). The position information provides the chromosome and nucleotide position, and the Build references the sequence update information from which the SNP position was obtained. The most updated information is given, however, as genome information is generated, the position may change slightly. KCNA5 codes for the potassium voltage-gated channel, subfamily A, member 5 protein. This protein mediates the voltage-dependent potassium ion permeability of excitable membranes. rs2239507 and its flanking regions were amplified using the following primers: 5'-agt cag gat cag gta ttt ttc ct-3' (SEQ ID NO. 1) and 5'-aga acc cag gtg aac caa t-3' (SEQ ID NO. 2). The SNP site was sequenced using the following oligo: 5'-aga tag agt cga tgc cag ctt cat ggg tct ctg acc tca ctg tct-3' (SEQ ID NO. 3). Table 14 includes the statistical breakdown of allele distribution within the patient groups.

TABLE 14

| Patient Group | SNP rs2239507 | | | |
|---|---|---|---|---|
| | g/g | g/t | t/t | Total |
| Test (N, %) | 12 | 7 | 10 | 29 |
| | 41.4% | 24.1% | 34.5% | 100% |
| Control (N, %) | 5 | 21 | 23 | 49 |
| | 10.2% | 42.9% | 46.9% | 100% |
| Total (N, %) | 17 | 28 | 33 | 78 |
| | 21.8% | 35.9% | 42.3% | 100% |

As shown in Table 14, twelve, or 41.4%, of test patients had the genotype g/g, whereas only five, or 10.2%, of control patients had the genotype g/g.

rs7626962 is located at position chr3:38595911, Build 116, within the SCN5A gene (Accession No. NT 022517). The SCN5A gene codes for the sodium channel, voltage-gated, type V, alpha (long QT syndrome 3) protein. This protein produces sodium channels that transport sodium ions across cell membranes and plays a key role in generating and transmitting electrical signals. rs7626962 and its flanking regions were amplified using the following primers: 5'-cct ccg gat tcc agg acc-3' (SEQ ID NO. 4) and 5'-ttc cgc ttt cca ctg ctg-3' (SEQ ID NO. 5). The SNP site was sequenced using the following oligo: 5'-gga tgg cgt tcc gtc cta tta gat gca ctg gcc tcg gcc tca gag-3' (SEQ ID NO. 6). Table 15 shows the statistical breakdown of the patient groups.

TABLE 15

| Patient | SNP rs7626962 | | |
|---|---|---|---|
| Group | g/g | t/t | Total |
| Test (N, %) | 23 | 6 | 29 |
| | 79.3% | 20.7% | 100% |
| Control (N, %) | 48 | 1 | 49 |
| | 98.0% | 2.0% | 100% |
| Total (N, %) | 71 | 7 | 78 |
| | 91.0% | 9.0% | 100% | rs3743496 is located at position chr15:71401461, Build 121, within the gene HCN4 (Accession No. NT_010194). The gene codes for the potassium/sodium hyperpolarization-activated cyclic nucleotide-gated channel 4 protein. The protein is a hyperpolarization-activated ion channel that may contribute to native pacemaker currents in the heart. rs3743496 and its flanking regions were amplified using the following primers: 5'-att gtg ttc att tag aga aac agc t-3' (SEQ ID NO. 7) and 5'-ctt ctg agg ctc ccc agg-3' (SEQ ID NO. 8). The SNP site was sequenced using the following oligo: 5'-agg gtc tct acg ctg acg atc tgt aac ttg gag ctc cac tct gcc-3' (SEQ ID NO. 9). Table 16 shows the statistical breakdown of the patient groups. "Frequency Missing" indicates that the SNP could not be read for one patient sample. One or more patient samples could not be read for other SNPs, and this is indicated in the tables below.

TABLE 16

| Patient | SNP rs3743496 | | | |
|---|---|---|---|---|
| Group | a/a | c/a | c/c | Total |
| Test (N, %) | 2 | 3 | 24 | 29 |
| | 6.9% | 10.3% | 82.8% | 100% |
| Control (N, %) | 0 | 0 | 48 | 48 |
| | 0.0% | 0.0% | 100% | 100% |
| Total (N, %) | 2 | 3 | 72 | 77 |
| | 2.6% | 3.9% | 93.5% | 100% |
| Frequency Missing = 1 | | | | | rs2072715 is located at position chr22:38339084, Build 121, within the gene CACNA1I (Accession No. NT_011520). The gene codes for the calcium channel, voltage-dependent, alpha 1I subunit protein. The protein is a voltage-sensitive calcium channel that serves pacemaking functions in central neurons and cardiac nodal cells. rs2072715 and its flanking regions were amplified using the following primers: 5'-tca gta gga aat gaa ggc ttt t-3' (SEQ ID NO. 10) and 5'-att tca ggg aac gaa tgg a-3' (SEQ ID NO. 11). The SNP site was sequenced using the following oligo: 5'-gcg gta ggt tcc cga cat att ctt caa gca gcg gga ggg ggt ggc-3' (SEQ ID NO. 12). Table 17 includes the statistical breakdown of the allelic distribution within the patient groups.

TABLE 17

| Patient | SNP rs2072715 | | |
|---|---|---|---|
| Group | g/a | g/g | Total |
| Test (N, %) | 8 | 21 | 29 |
| | 27.6% | 72.4% | 100% |
| Control (N, %) | 4 | 45 | 49 |
| | 8.2% | 91.8% | 100% |
| Total (N, %) | 12 | 66 | 78 |
| | 15.4% | 84.6% | 100% | rs12276475 is located at position chr11:29989733, Build 120, within the KCNA4 gene (Accession No. NT_009237). This gene codes for the potassium voltage-gated channel, shaker-related subfamily, member 4 protein. This protein mediates the voltage-dependent potassium ion permeability of excitable membranes. rs12276475 and its flanking regions were amplified using the following primers: 5'-aca aac tca aag gaa aac cat aca-3' (SEQ ID NO. 13) and 5'-atc tcg tca tgg cac tga gt-3' (SEQ ID NO. 14). The SNP site was sequenced using the following oligo: 5'-gtg att ctg tac gtg tcg cct ggg ttg ttg aat gat act tca gca-3' (SEQ ID NO. 15). Table 18 includes the statistical breakdown for the patient groups.

TABLE 18

| Patient | SNP rs12276475 | | | |
|---|---|---|---|---|
| Group | a/a | c/a | c/c | Total |
| Test (N, %) | 11 | 18 | 0 | 29 |
| | 37.9% | 62.1% | 0.0% | 100% |
| Control (N, %) | 33 | 15 | 1 | 49 |
| | 67.3% | 30.6% | 2.1% | 100% |
| Total (N, %) | 44 | 33 | 1 | 78 |
| | 56.4% | 42.3% | 1.3% | 100% | rs1544503 is located at position chr12:2308902, Build 123, within the CACNA1C gene (Accession No. NT_009759). The protein is involved in mediating entry of calcium ions into excitable cells and plays an important role in excitation-contraction coupling in the heart. rs1544503 and its flanking regions were amplified using the following primers: 5'-aat agg atg cac ttg ctt gac-3' (SEQ ID NO. 16) and 5'-atg agg aag agt ccc ttc acc-3' (SEQ ID NO. 17). The SNP site was sequenced using the following oligo: 5'-agg gtc tct acg ctg acg att gat gtt cat tga tgg gga cag gca-3' (SEQ ID NO. 18). Table 19 shows the statistical breakdown.

TABLE 19

| Patient | SNP rs1544503 | | | |
|---|---|---|---|---|
| Group | c/c | t/c | t/t | Total |
| Test (N, %) | 16 | 7 | 5 | 28 |
| | 57.1% | 25.0% | 17.9% | 100% |
| Control (N, %) | 21 | 24 | 2 | 47 |
| | 44.7% | 51.1% | 4.3% | 100% |
| Total (N, %) | 37 | 31 | 7 | 75 |
| | 49.3% | 41.3% | 9.3% | 100% |
| Frequency Missing = 3 | | | | | rs723672 is located at position chr12:2031822, Build 120, within the CACNA1C gene (Accession No. NT_009759). The function of the gene product was discussed previously. rs723672 and its flanking regions were amplified using the following primers: 5'-tat ctg tca ctt cta caa ccg ct-3' (SEQ ID NO. 19) and 5'-aat tcc aag gag gag gaa tac a-3' (SEQ ID NO. 20). The SNP site was sequenced using the following oligo: 5'-gcg gta ggt tcc cga cat ata tcg ggc cac tga aca aaa cgg caa-3' (SEQ ID NO. 21). Table 20 shows the statistical breakdown.

TABLE 20

| Patient | SNP rs723672 | | | |
|---|---|---|---|---|
| Group | a/a | g/a | g/g | Total |
| Test (N, %) | 2 | 15 | 11 | 28 |
| | 7.1% | 53.6% | 39.3% | 100% |
| Control | 13 | 15 | 19 | 47 |

TABLE 20-continued

| Patient | SNP rs723672 | | | |
|---|---|---|---|---|
| Group | a/a | g/a | g/g | Total |
| (N, %) | | 27.7% | 31.9% | 40.4% | 100% |
| Total | 15 | 30 | 30 | 75 |
| (N, %) | 20.0% | 40.0% | 40.0% | 100% |
| Frequency Missing = 3 | | | | | rs3752158 is located at position chr19:558984, Build 120, within the HCN2 gene (Accession No. NT_011255). This gene codes for the hyperpolarization activated cyclic nucleotide-gated potassium channel 2 protein. This protein may play a role in generation of neuronal pacemaker activity. rs3752158 and its flanking regions were amplified using the following primers: 5'-atg cac agc atg tgg ctc-3' (SEQ ID NO. 22) and 5'-tga gca cct gcc cac cac-3' (SEQ ID NO. 23). The SNP site was sequenced using the following oligo: 5'-agg gtc tct acg ctg acg att gca gaa cca ctc gtg gag tga act-3' (SEQ ID NO. 24). Table 21 shows a statistical breakdown of the allelic distribution.

TABLE 21

| Patient | SNP rs3752158 | | | |
|---|---|---|---|---|
| Group | c/c | c/g | g/g | Total |
| Test (N, %) | 5 | 2 | 20 | 27 |
| | 18.5% | 7.4% | 74.1% | 100% |
| Control | 1 | 7 | 40 | 48 |
| (N, %) | 2.1% | 14.6% | 83.3% | 100% |
| Total (N, %) | 6 | 9 | 60 | 75 |
| | 8.0% | 12.0% | 80.0% | 100% |
| Frequency Missing = 3 | | | | | rs1023214 is located at position chr1:234128106, Build 123, within the RYR2 gene (Accession No. NT_004836). This gene codes for the ryanodine receptor 2 protein. The protein is involved in providing calcium required for cardiac muscle excitation-contraction coupling. rs1023214 and its flanking regions were amplified using the following primers: 5'-agt aaa gca tta tgg agg cat aaa-3' (SEQ ID NO. 25) and 5'-gca tct aag ttc tcc taa att ttt tat t-3' (SEQ ID NO. 26). The SNP site was sequenced using the following oligo: 5'-ggc tat gat tcg caa tgc ttg ttt gga tta tga cat cat tct ata-3' (SEQ ID NO. 27). Table 22 shows a statistical breakdown of the allelic distribution.

TABLE 22

| Patient | SNP rs1023214 | | | |
|---|---|---|---|---|
| Group | a/a | g/a | g/g | Total |
| Test (N, %) | 16 | 3 | 3 | 22 |
| | 72.7% | 13.6% | 13.6% | 100% |
| Control | 15 | 15 | 2 | 32 |
| (N, %) | 46.9% | 46.9% | 6.3% | 100% |
| Total (N, %) | 31 | 18 | 5 | 54 |
| | 57.4% | 33.3% | 9.3% | 100% |
| Frequency Missing = 24 | | | | | rs730818 is located at position chr17:40227887, Build 86, within the GJA7 gene (Accession No. NT_010783). The gene codes for the gap junction alpha-7 (Connexin 45) protein. This protein is involved in cell-to-cell communication. rs730818 and its flanking regions were amplified using the following primers: 5'-ttt ttc ttt cag aag ccc ct-3' (SEQ ID NO. 28) and 5'-aca tga cat ggt gac aag ca-3' (SEQ ID NO. 29). The SNP site was sequenced using the following oligo: 5'-cgt gcc gct cgt gat aga att ctt tgt caa ttg act ttt tct ccc-3' (SEQ ID NO. 30). Table 23 includes a statistical breakdown of the allelic distribution.

TABLE 23

| Patient | SNP rs730818 | | | |
|---|---|---|---|---|
| Group | a/a | g/a | g/g | Total |
| Test (N, %) | 0 | 16 | 9 | 25 |
| | 0.0% | 64.0% | 36.0% | 100% |
| Control | 10 | 21 | 18 | 49 |
| (N, %) | 20.4% | 42.9% | 36.7% | 100% |
| Total (N, %) | 10 | 37 | 27 | 74 |
| | 13.5% | 50.0% | 36.5% | 100% |
| Frequency Missing = 4 | | | | | rs1842082 is located at position chr1:233951526, Build 123, within the RYR2 gene (Accession No. NT_004836). This gene codes for the gap junction alpha-7 protein as described above. rs1842082 and its flanking regions were amplified using the following primers: 5'-aag aaa aaa tac aaa gac agt ggc-3' (SEQ ID NO. 31) and 5'-tgt caa aac ctt tgg ttc aaa-3' (SEQ ID NO. 32). The SNP site was sequenced using the following oligo: 5'-agg gtc tct acg ctg acg att tgt taa gcc tcc ttc ccg tta ttc-3' (SEQ ID NO. 33). Table 24 is a statistical breakdown of the patient groups.

TABLE 24

| Patient | SNP rs1842082 | | | |
|---|---|---|---|---|
| Group | c/c | c/g | g/g | Total |
| Test (N, %) | 5 | 19 | 5 | 29 |
| | 17.2% | 65.5% | 17.2% | 100% |
| Control | 21 | 19 | 9 | 49 |
| (N, %) | 42.9% | 38.8% | 18.4% | 100% |
| Total (N, %) | 26 | 38 | 14 | 78 |
| | 33.3% | 48.7% | 18.0% | 100% | rs545118 is located at position chr11:30002105, Build 123, within the KCNA4 gene (Accession No. NT_009237). The gene product was described previously. rs545118 and its flanking regions were amplified using the following primers: 5'-cat ttt tac aga caa gaa aat tta gg-3' (SEQ ID NO. 34) and 5'-ata ggt ttt tct ctc cag cc-3' (SEQ ID NO. 35). The SNP site was sequenced using the following oligo: 5'-acg cac gtc cac ggt gat ttc ttg gct gca gaa cct ctg gct aag-3' (SEQ ID NO. 36). Table 25 shows the statistical breakdown of the patient groups.

TABLE 25

| Patient | SNP rs545118 | | | |
|---|---|---|---|---|
| Group | a/a | t/a | t/t | Total |
| Test (N, %) | 19 | 10 | 0 | 29 |
| | 65.5% | 34.5% | 0.0% | 100% |
| Control | 20 | 24 | 5 | 49 |
| (N, %) | 40.8% | 49.0% | 10.2% | 100% |
| Total (N, %) | 39 | 34 | 5 | 78 |
| | 50.0% | 43.6% | 6.4% | 100% | rs7578438 is located at position chr2:155388192, Build 121, within the KCNJ3 gene (Accession No. NT_005403). This gene codes for the potassium inwardly-rectifying channel, subfamily J, member 3 protein. This protein forms potassium channels that are characterized by a greater tendency to allow potassium to flow into the cell rather than out of it. rs7578438 and its flanking regions were amplified using the following primers: 5'-cat aaa tct taa ctt tta gcg atc g-3' (SEQ ID NO. 37) and 5'-agg atc gtt ttc tag ata caa atg tat aa-3' (SEQ ID NO. 38). The SNP site was sequenced using the following oligo: 5'-agc gat ctg cga gac cgt atg ata tgg tct aga tca aca ata att-3' (SEQ ID NO. 39). Table 26 includes a statistical breakdown of the patient groups.

TABLE 26

| Patient Group | SNP rs7578438 | | | |
| --- | --- | --- | --- | --- |
| | g/g | g/t | t/t | Total |
| Test | 9 | 16 | 2 | 27 |
| (N, %) | 33.3% | 59.3% | 7.4% | 100% |
| Control | 14 | 29 | 6 | 49 |
| (N, %) | 28.6% | 59.2% | 12.2% | 100% |
| Total | 23 | 45 | 8 | 76 |
| (N, %) | 30.3% | 59.2% | 10.5% | 100% |

Frequency Missing = 2 rs802351 is located at position chr7:119166671, Build 123, within the KCND2 gene (Accession No. NT_007933). This gene codes for the potassium voltage-gated channel, subfamily D, member 2 protein. This protein is a pore-forming subunit of voltage-gated, rapidly inactivating A-type potassium channels. rs802351 and its flanking regions were amplified using the following primers: 5'-aaa act ata agt att ttc ttg tga agg tg-3' (SEQ ID NO. 40) and 5'-aac att tgc caa tgc aat g-3' (SEQ ID NO. 41). The SNP site was sequenced using the following oligo: 5'-gga tgg cgt tcc gtc cta tta gca gca ttt aaa taa atg ccc tct-3' (SEQ ID NO. 42). Table 27 includes a statistical breakdown of the allelic distribution.

TABLE 27

| Patient Group | SNP rs802351 | | | |
| --- | --- | --- | --- | --- |
| | g/g | g/t | t/t | Total |
| Test | 1 | 10 | 17 | 28 |
| (N, %) | 3.6% | 35.7% | 60.7% | 100% |
| Control | 2 | 9 | 38 | 49 |
| (N, %) | 4.1% | 18.4% | 77.6% | 100% |
| Total | 3 | 19 | 55 | 77 |
| (N, %) | 3.9% | 24.7% | 71.4% | 100% |

Frequency Missing = 1

Using the same data, a second analysis was performed to compare major and minor allele frequencies among the patient groups. The major allele is that which occurs most frequently, while the minor allele is that which occurs least frequently. Each patient has two alleles, therefore, 156 alleles are assessed for each SNP. It was determined whether patients with particular alleles in their genotype were more likely to belong to one group over the other.

Table 28 shows the results of either a chi-square or Fisher's exact test analysis where at least one of the alleles resulted in a p-value less than 0.05.

TABLE 28

| Gene/Accession No. | SNP | Major Allele | P-value | Minor Allele | P-value |
| --- | --- | --- | --- | --- | --- |
| Refer to discussion | rs12276475 | a | 0.4388 | C (test) | 0.0113 |
| KCNK4 NT_033903 | rs1320840 | g | 0.6372 | a (control) | 0.0293 |
| KCNA4 NT_009237 | rs1323860 | a (test) | 0.022 | g | 0.4671 |
| KCND3 NT_019273 | rs1538389 | c (control) | 0.0448* | t | 0.3341 |
| KCND3 NT_019273 | rs1808973 | t | 0.6998 | c (control) | 0.0443 |
| Refer to discussion | rs1842082 | c | 0.9003 | g (test) | 0.0204 |
| KCND2 NT_007933 | rs1859534 | t (test) | 0.7039 | a | 0.0317 |
| Refer to discussion | rs2072715 | g | N/A** | a (test) | 0.0473* |
| Refer to discussion | rs2238043 | g (test) | 0.0462* | a | 0.142 |
| Refer to discussion | rs2239507 | t (control) | 0.0013 | g | 0.2819 |
| SLC8A1 NT_022184 | rs2373860 | t (control) | 0.0419 | a | 0.7046 |
| KCNK4 NT_033903 | rs3739081 | a (control) | 0.0368 | g | 0.7621 |
| Refer to discussion | rs3743496 | c | 0.0653 | a (test) | 0.0060* |
| Refer to discussion | rs3752158 | g (control) | 0.0207* | c | 0.3359 |
| KCND2 NT_007933 | rs3814463 | t (control) | 0.050* | c | 0.1629 |
| KCNQ1 NT_009237 | rs4930127 | g (control) | 0.0309* | a | 0.2581 |
| Refer to discussion | rs545118 | a | 0.0754 | t (control) | 0.035 |
| Refer to discussion | rs723672 | g | 0.6552 | t (test) | 0.0168* |
| KCND3 NT_019273 | rs730022 | c (test) | 0.0227* | t | 0.2121 |
| Refer to discussion | rs730818 | g (test) | 0.0134* | a | 0.9505 |
| Refer to discussion | rs7578438 | g | 0.1077 | a (test) | 0.0137* |
| Refer to discussion | rs7626962 | g (control) | 0.0094* | t (test) | 0.0094* |
| CACNA1C NT_009759 | rs765125 | t (test) | 0.0335 | c | 0.9409 |
| Refer to discussion | rs802351 | t (control) | 0.0310* | c (test) | 0.0151* |

*Fisher's exact test used as criteria for chi-square test not met.
**All patients had at least one allele g, so no test was performed.

Column 1 indicates the gene and Accession Number for SNPs not previously discussed. Columns 3 and 5 indicate the patient group in parentheses, which had a higher percentage of patients with the allele in question if there was a significant difference. For example, a higher percentage of test patients than control patients had the c allele in the gene SNP rs12276475.

Table 29 lists the chromosome position and Build number for each SNP. Table 29 additionally includes the primers used to amplify each SNP and the oligo used to sequence each SNP. SNPs described elsewhere are indicated.

TABLE 29

| Gene SNP | SNP Position/ Build No. | Primers | Oligo |
| --- | --- | --- | --- |
| rs12276475 | | | Refer to discussion |
| rs1320840 | Chr2: 26860830 111 | 5'-aaa atg ttc agc ttg taa ttc ca-3' (SEQ ID NO. 43) 5'-tag aag cta gag agg aaa gtg aca a-3' (SEQ ID NO. 44) | 5'-agg gtc tct acg ctg acg atc ccc cca aag cta gtg ttt agc tct-3' (SEQ ID NO. 45) |

TABLE 29-continued

| Gene SNP | SNP Position/ Build No. | Primers | Oligo |
|---|---|---|---|
| rs1323860 | Chr11: 29991812 121 | 5'-aag agc cat gtg ggc cat-3' (SEQ ID NO. 46)<br>5'-aat att ttc aag agt atg ggg ca-3' (SEQ ID NO. 47) | 5'-aga gcg agt gac gca tac tat ttc agc tca gtt tat ttt tat ggt-3' (SEQ ID NO. 48) |
| rs1538389 | Chr1: 112039186 88 | 5'-ata att ggg agc tgg agt agc t-3' (SEQ ID NO. 49)<br>5'-tca gag gac aca gta tct aag gc-3' (SEQ ID NO. 50) | 5'-cgt gcc gct cgt gat aga ata tct tag taa taa tcc caa gca aac-3' (SEQ ID NO. 51) |
| rs1808973 | Chr1: 112199876 123 | 5'-ttg tgc tgg tgt acc tcg a-3' (SEQ ID NO. 52)<br>5'-aga agg agt aaa ggc agc c-3' (SEQ ID NO. 53) | 5'-cgt gcc gct cgt gat aga atg gca gat gat ttg ttg agc aga atg-3' (SEQ ID NO. 54) |
| rs1842082 | | Refer to the discussion above. | |
| rs1859534 | Chr7: 119321505 123 | 5'-agt caa gtc cag tcc aca gta ata ta-3' (SEQ ID NO. 55)<br>5'-aaa ata ctt aag gat ata ctc taa agg ca-3' (SEQ ID NO. 56) | 5'-agg gtc tct acg ctg acg ata tgt gtg ttt gtg ctt ttt aga tta-3' (SEQ ID NO. 57) |
| rs2072715 | | Refer to the discussion | |
| rs2238043 | | Refer to the discussion | |
| rs2239507 | | Refer to the discussion | |
| rs2373860 | Chr2: 40547682 123 | 5'-att tca act taa gta ttg aat cca aag-3' (SEQ ID NO. 58)<br>5'-gtt ttt ttc tct tat ctt tct ttt gtt c-3' (SEQ ID NO. 59) | 5'-agc gat ctg cga gac cgt att ttt tct atg gtt ctt atg gct ata-3' (SEQ ID NO. 60) |
| rs3739081 | Chr2: 26867272 123 | 5'-ata aag aaa gga ggg caa gtg t-3' (SEQ ID NO. 61)<br>5'-tcc cac ctg cct ctg tct-3' (SEQ ID NO. 62) | 5'-cga ctg tag gtg cgt aac tca aac agc taa atg caa caa tag cag-3' (SEQ ID NO. 63) |
| rs3743496 | | Refer to the discussion | |
| rs3752158 | | Refer to the discussion. | |
| rs3814463 | Chr7: 118937980 120 | 5'-aat tgg ttg tct tct ggg g-3' (SEQ ID NO. 64)<br>5'-att ttt tgg caa gtt gga ca-3' (SEQ ID NO. 65) | 5'-agc gat ctg cga gac cgt atg act gga agg caa gac ccg caa agc-3' (SEQ ID NO. 66) |
| rs4930127 | Chr 11: 2550553 120 | 5'-ctg tgc aga cgc cta agg-3' (SEQ ID NO. 67)<br>5'-tgg gct ata ttg aag ccg-3' (SEQ ID NO. 68) | 5'-agc gat ctg cga gac cgt atg tga acc gcg ctg gag cgg cgt agg-3' (SEQ ID NO. 69) |
| rs545118 | | Refer to the discussion | |
| rs723672 | | Refer to the discussion | |
| rs730022 | Chr 1: 112227635 123 | 5'-gat aac caa gag tta acc ata att aca g-3' (SEQ ID NO. 70)<br>5'-taa gta tgc gtg tcc agg aa-3' (SEQ ID NO. 71) | 5'-acg cac gtc cac ggt gat tta agt aaa aat aaa cta atg ata ctc-3' (SEQ ID NO. 72) |
| rs730818 | | Refer to the discussion | |
| rs7578438 | | Refer to the discussion | |
| rs7626962 | | Refer to the discussion | |
| rs765125 | Chr 12: 2026468 121 | 5'-tac tgt ggg caa cat ttc ag-3' (SEQ ID NO. 73)<br>5'-atn ctg cac cct ctt cag-3' (SEQ ID NO. 74) | 5'-ggc tat gat tcg caa tgc ttt tgg ggg att tcc ccc aaa gcc ttc-3' (SEQ ID NO. 75) |
| rs802351 | | Refer to the discussion | |

In nine of 15 cases where there was a significant difference between the patient groups in terms of the major allele, the control group had the higher percentage of patients with the allele. In eight of the eleven SNPs in which there was a significant difference between the patient groups in terms of minor allele frequency, the test group had the higher percentage of patients with the minor allele.

Figure 9:
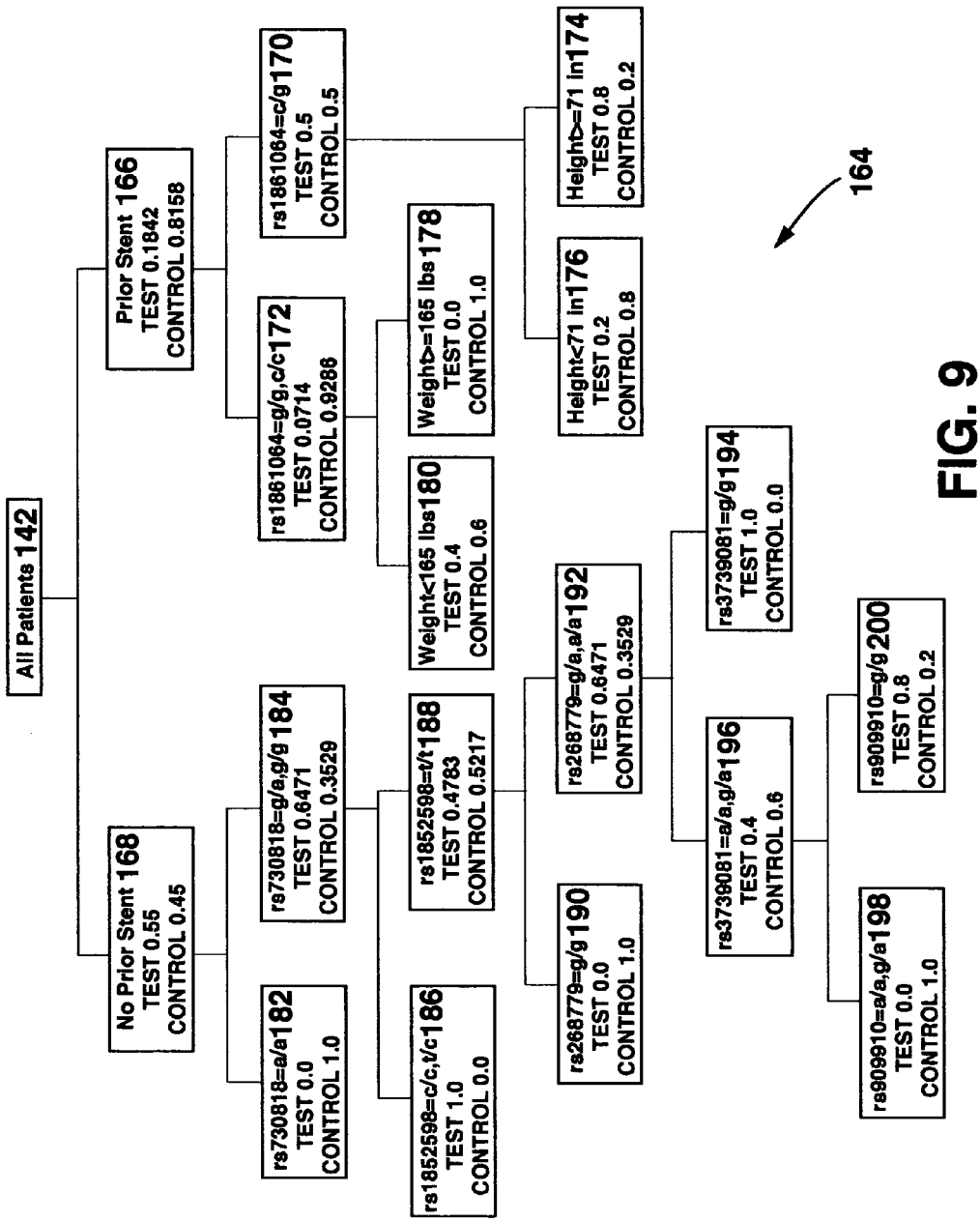
FIG. 9 is a logical diagram of a representative classification algorithm.

Next, the CART method was used to analyze the relationship between patient genotypes and the likelihood of experiencing a VT/VF episode. Test versus control group was the response variable, and the set of 86 demographic and 162 SNPs were the predictor variables. The resulting tree analysis 164 is shown in FIG. 9.

Tree analysis 164 begins by partitioning all patients, represented by group 142, based on the History of Stent variable. Thirty-eight patients had a stent and were placed into group 166, while 40 patients that had no stent and were placed into group 168. Of the patients in group 166, only seven, or 18.4% belonged to the test group. Conversely, of the patients in group 168, 22, or 55%, belonged to the test group. The p-value of this clustering using a chi-square test is 0.0007.

Group 166 was further partitioned by SNP rs1861064. Ten patients having the genotype c/g were placed in group 170, while 28 patients having genotypes g/g or c/c were placed in group 172.

Of the patients in group 170, five, or 50%, were test patients. Group 170 was further partitioned based on Patient Height. Five patients from group 170 were greater than or equal to 71 inches and placed into group 174. Four, or 80%, of these patients were test patients and are at risk of VT/VF. The remaining five patients from group 170 were less than 71 inches and placed into group 176. Four, or 80%, of these patients were control patients and, therefore, not at risk of VT/VF.

Patients in group 172 were further partitioned based on Patient Weight. Twenty-three patients from group 172 weighed greater than or equal to 165 lbs. and placed into group 178. All 26 patients were from the control group, and therefore, patients in this group are deemed not to be at significant risk of experiencing VT/VF.

The remaining five patients weigh less than 165 lbs. and were placed into group 180. Three patients, or 60%, were control patients, and no further assessment could be made for these patients.

Patients in group 168 were further partitioned based on SNP rs730818. Six patients having the genotype a/a were placed into group 182. All six patients were from the control group. Therefore, patients in group 182 are not at significant risk of VT/VF.

Thirty-four patients having the genotype g/a or g/g were placed in group 184. Group 184 was further partitioned based on SNP rs1852598. Eleven patients from group 184 having the genotype c/c or t/c were placed in group 186. All 11 patients were from the test group. Therefore, patients in group 186 are at significant risk of VT/VF.

The remaining 23 patients from group 184 having the genotype t/t were placed into group 188. Patients in group 188 were further partitioned based on SNP rs268779. Six patients having genotype g/g were placed into group 190. All six patients were from the control group, and therefore, patients in group 190 are not at significant risk of VT/VF.

The remaining 17 patients from group 188 were placed in group 192 and further partitioned based on SNP rs3739081. Seven patients having the genotype g/g were placed into group 194. All seven patients were from the test group and, therefore, deemed to be at significant risk of VT/VF.

Ten patients from group 192 had the genotype a/a or g/a and were placed in group 196. Patients in group 196 were further partitioned based on SNP rs909910. Five patients having genotype a/a or g/a were placed into group 198. All five patients belonged to the control group. Therefore, patients in group 198 are not at significant risk of experiencing fatal VT/VF.

The remaining five patients from group 196 had the genotype g/g and were placed into group 200. Four of the five patients were from the test group. Therefore, patients placed in group 200 are at risk of experiencing fatal VT/VF.

The three analyses indicate that patients who have recently experienced at least one episode of VT/VF differ from those who have not in at least one gene SNP. These SNPs, in turn, can be used as class identifiers for classifying patients. Table 30 summarizes information regarding the SNPs utilized in tree analysis 164.

Example 3

A third genetic study examining 451 SNPs was performed with an additional 12 patients for a total of 90 patient samples included in the study. Here, the control group consists of 52 patients, and the test group consists of 38 patients. The analysis was carried out as previously described, but the results are used to stratify patient risk of experiencing fatal VT/VF. This stratification scheme can be subsequently used as a class identifier in a classification algorithm.

rs1008832 is located at position chr12:2483782, Build 120, within the CACNA1C gene (Accession No. NT_009759), which codes for the calcium channel, voltage-dependent, L type, alpha 1C subunit protein. The function of this protein was previously described. The SNP and its flanking regions were amplified using primers 5'-tgc aca tga aca aag ccc-3' (SEQ ID NO. 84) and 5'-aaa gtt agg aaa gaa gaa gca gaa t-3' (SEQ ID NO. 85). The SNP was sequenced using the oligo 5'-aga gcg agt gac gca tac taa ggc agg cag cag gtg tga gca gat-3' (SEQ ID NO. 86). Table 31 shows the statistical breakdown of the genotypes for this SNP.

TABLE 31

| Count<br>Total (%)<br>Column (%)<br>Row (%) | Control | Test | Total |
|---|---|---|---|
| a/a | 28 | 11 | 39 |
|  | 31.1% | 12.2% | 43.3% |
|  | 53.9% | 29.0% |  |
|  | 71.8% | 28.2% |  |
| a/g | 19 | 20 | 39 |
|  | 21.1% | 22.2% | 43.3% |
|  | 36.5% | 52.6% |  |
|  | 48.7% | 51.3% |  |
| g/g | 5 | 7 | 12 |
|  | 5.6% | 7.8% | 13.3% |
|  | 9.6% | 18.4% |  |
|  | 41.7% | 58.3% |  |
| Total | 52 | 38 | 90 |
|  | 57.8% | 42.2% |  |

The first (top) value in each cell is the number, or count, of patients placed in that set. The second value is the percentage of the total number of patients placed in the set. The third value is the percentage of patients from either the control or

TABLE 30

| SNP/Gene | SNP Position/ Build No. | Primers | Oligo |
|---|---|---|---|
| rs1861064<br>KCND2 | Chr7:<br>119132866<br>120 | 5'-tgt tgt gta tag ctt att atg aaa ctg a-3' (SEQ ID NO. 76)<br>5'-tta ggc aaa aat gct acc aat c-3' (SEQ ID NO. 77) | 5'-gcg gta ggt tcc cga cat att ata aaa ttt gca gtt tgt tta ctc-3' (SEQ ID NO. 78) |
| rs268779<br>RYR2 | Chr1:<br>233736784<br>121 | 5'-agt ggg ctc aac ttt tac tgt t-3' (SEQ ID NO. 79)<br>5'-gaa aga ttc ctg tca ggg c-3' (SEQ ID NO. 80) | 5'-gga tgg cgt tcc gtc cta tta atc ttt aat aag aga ggc agt tac-3' (SEQ ID NO. 81) |
| rs909910<br>CACNA1H | Chr16:<br>1138939<br>86 | 5'-agc agg tga gtg tcc ttt g-3' (SEQ ID NO. 82)<br>5'-tgg atc cca aaa ttc ctt g-3' (SEQ ID NO. 83) | 5'-acg cac gtc cac ggt gat ttg cca ccc agt cag cag gta ttt att-3' (SEQ ID NO. 102) |
| rs730818 |  | Refer to the discussion above. |  |
| rs1852598 | Chr5:<br>45648477 | 5'-tta gtt tac ttt tgt tga tat tat gtg gg-3' (SEQ ID NO. 103)<br>5'-ttt gat ata gtg gca aaa aat tta gg-3' (SEQ ID NO. 104) | 5'-gtg att ctg tac gtg tcg cct tct att ctt aat aat cag tga aag-3' (SEQ ID NO. 105) |
| rs3739081 |  | Refer to the discussion above. |  | test group (depending on the column) packed in the set. The fourth value is the percentage of control or test patients (depending on the column) having a specific genotype from the total number of patients having that specific genotype. The bottom right cell is the total number of patients utilized for the SNP analysis. Here, 90 patients were used, however, in subsequent analyses the total number of patients may be less if a patient's sequence could not be read for a particular SNP. The information in Table 31 was subsequently used to calculate probabilities useful in stratifying patients as to their risk of VT/VF.

Figure 10:
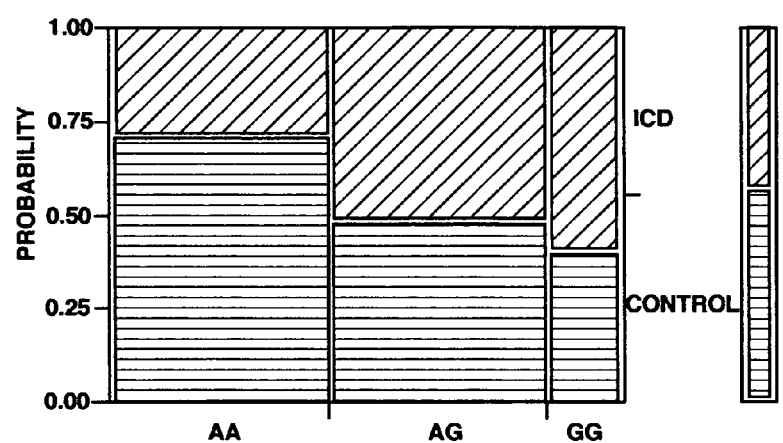
FIG. 10 is a mosaic plot illustrating the probability of experiencing fatal VT/VF as a function of allele specific inheritance of SNP rs1008832.

FIG. 10 is a mosaic plot illustrating the resulting risk stratification. The horizontal axis of the graph lists the possible genotypes at this particular SNP. The vertical axis is the probability of experiencing fatal VT/VF.

As shown in the graph, the presence of g at the SNP position indicates increased susceptibility to fatal VT/VF as compared to the presence of a at the SNP position. Specifically, patients with genotype a/a have almost a 75% probability of not experiencing fatal VT/VF, while the a/g genotype indicates about a 50% probability of not experiencing fatal VT/VF, and a g/g genotype indicates about a 40% probability of not experiencing fatal VT/VF.

rs2238043 is located at position chr12:2145924, Build 123, within the CACNA1C gene. The gene product was described above. The SNP and its flanking regions were amplified using primers 5'-ata cta gac aga gag caa gac ttc aag-3' (SEQ ID NO. 87) and 5'-tcc cca ttc aaa gtg cct-3' (SEQ ID NO. 88). The SNP was sequenced using the oligo 5'-aga tag agt cga tgc cag ctg aag tga gat acc taa gga gtg tca-3' (SEQ ID NO. 89). Table 32 shows the statistical breakdown of the genotypes for this SNP.

TABLE 32

| Count<br>Total (%)<br>Column (%)<br>Row (%) | CONTROL | ICD | Total |
|---|---|---|---|
| g/g | 13<br>14.4%<br>25.0%<br>44.8% | 16<br>17.8%<br>42.1%<br>55.2% | 29<br>32.2% |
| g/a | 29<br>32.2%<br>55.8%<br>58.0% | 21<br>23.3%<br>55.3%<br>42.0% | 50<br>55.6% |
| a/a | 10<br>11.1%<br>19.2%<br>90.9% | 1<br>1.1%<br>2.6%<br>9.1% | 11<br>12.2% |
| Total | 52<br>57.8% | 38<br>42.2% | 90 |

Figure 11:
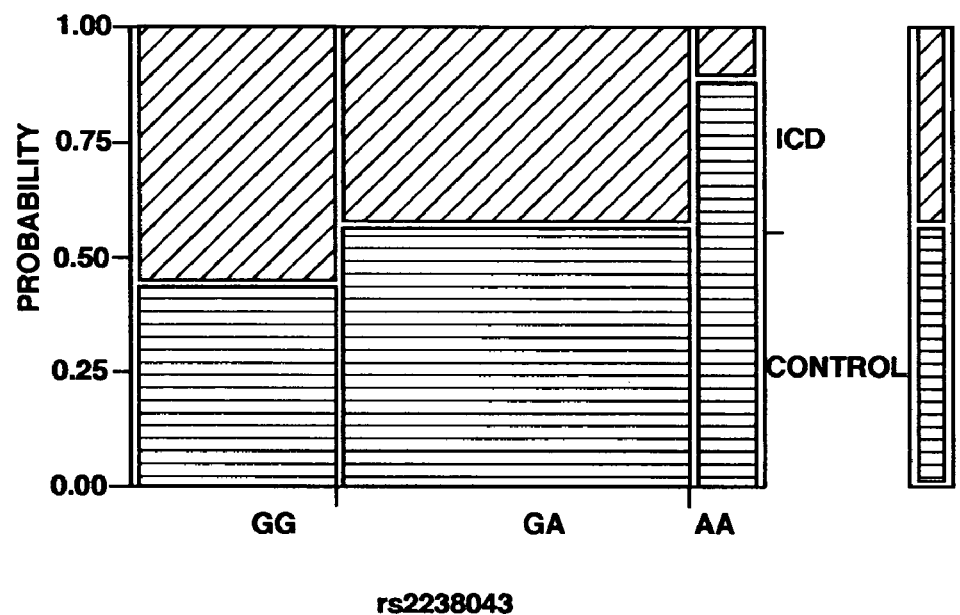
FIG. 11 is a mosaic plot illustrating the probability of experiencing fatal VT/VF as a function of allele specific inheritance of SNP rs2238043.

The information in Table 32 was used to calculate probabilities of patient VT/VF. FIG. 11 is a mosaic plot illustrating the resulting risk stratification.

As shown in the plot, the presence of g at the SNP position indicates increased susceptibility to fatal VT/VF as compared to the presence of a at the SNP position. Patients with genotype a/a have about a 90% probability of not experiencing fatal VT/VF, while the g/a genotype indicates about a 60% probability of not experiencing fatal VT/VF, and the g/g genotype indicates about a 45% probability of not experiencing fatal VT/VF.

rs198544 was previously described. Table 33 shows the statistical breakdown of the genotypes for this SNP.

TABLE 33

| Count<br>Total (%)<br>Column (%)<br>Row (%) | CONTROL | ICD | Total |
|---|---|---|---|
| c/c | 17<br>18.9%<br>32.7%<br>77.3% | 5<br>5.6%<br>13.2%<br>22.7% | 22<br>24.4% |
| c/g | 27<br>30.0%<br>51.9%<br>54.0% | 23<br>25.6%<br>60.5%<br>46.0% | 50<br>55.6% |
| g/g | 8<br>8.9%<br>15.4%<br>44.4% | 10<br>11.1%<br>26.3%<br>55.6% | 18<br>20.0% |
| Total | 52<br>57.8% | 38<br>42.2% | 90 |

Figure 12:
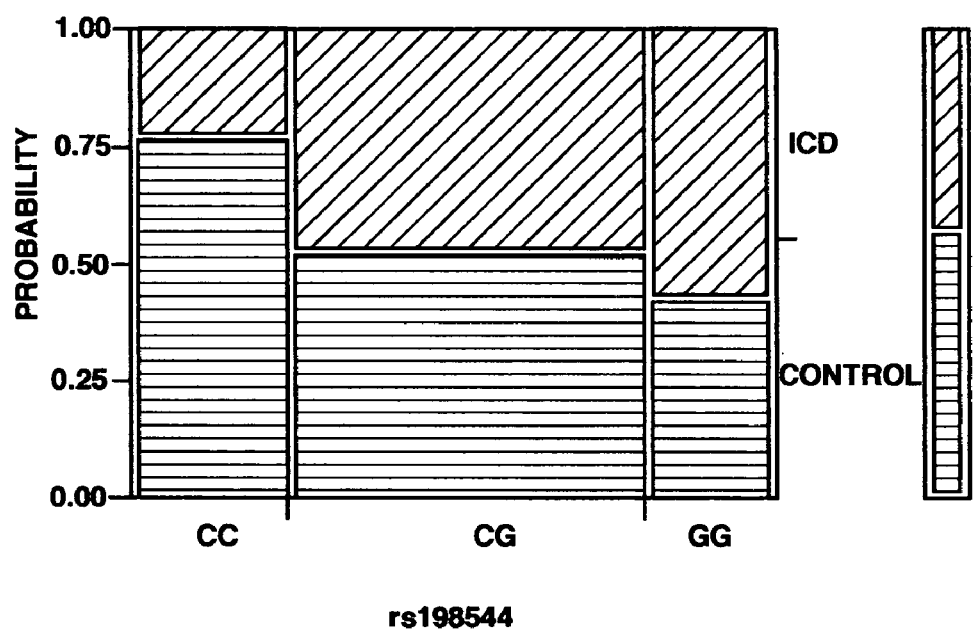
FIG. 12 is a mosaic plot illustrating the probability of experiencing fatal VT/VF as a function of allele specific inheritance of SNP rs198544.

The information in Table 33 was used to calculate probabilities of patient VT/VF. FIG. 12 is a mosaic plot illustrating the resulting risk stratification.

As shown in the plot, the presence of c at the SNP position indicates decreased susceptibility to fatal VT/VF as compared to the presence of g at the SNP position. Patients with genotype c/c have just over a 75% probability of not experiencing fatal VT/VF, while the c/g genotype indicates about a 50% probability of not experiencing fatal VT/VF, and the g/g genotype indicates about a 45% probability of not experiencing fatal VT/VF.

rs1009531 was previously described. Table 34 shows the statistical breakdown of the genotypes for this SNP.

TABLE 34

| Count<br>Total (%)<br>Column (%)<br>Row (%) | CONTROL | ICD | Total |
|---|---|---|---|
| a/a | 2<br>2.3%<br>3.9%<br>33.3% | 4<br>4.6%<br>10.8%<br>66.7% | 6<br>6.8% |
| a/g | 21<br>23.9%<br>41.2%<br>51.2% | 20<br>22.7%<br>54.1%<br>48.8% | 41<br>46.6% |
| g/g | 28<br>31.8%<br>54.9%<br>68.3% | 13<br>14.8%<br>35.1%<br>31.7% | 41<br>46.6% |
| Total | 51<br>58.0% | 37<br>42.1% | 88 |

Figure 13:
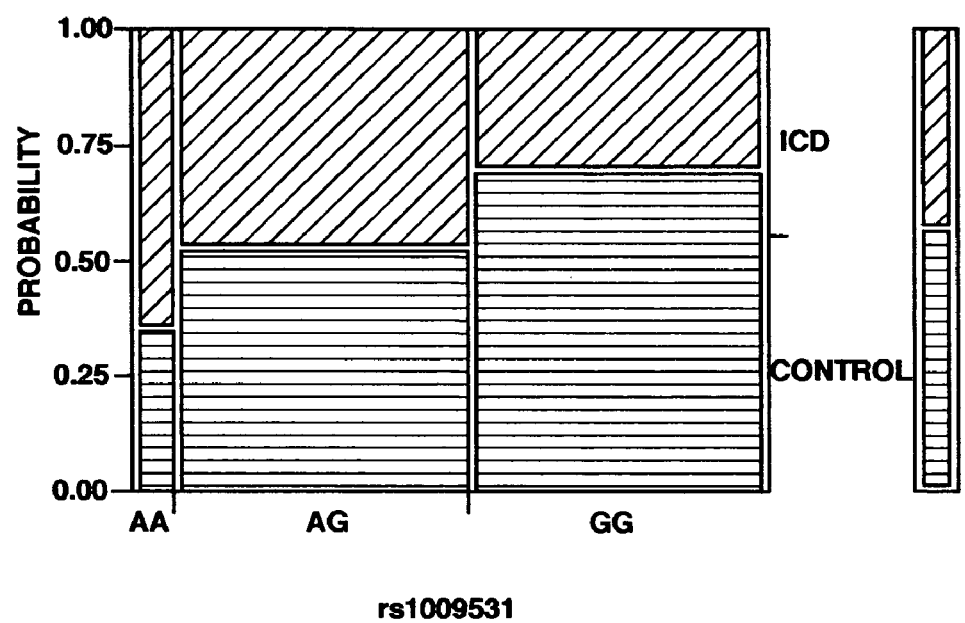
FIG. 13 is a mosaic plot illustrating the probability of experiencing fatal VT/VF as a function of allele specific inheritance of SNP rs1009531.

The information in Table 34 was used to calculate the probabilities of patient VT/VF. FIG. 13 is a mosaic plot illustrating the resulting risk stratification.

As shown in the plot, the presence of a at the SNP position indicates increased susceptibility to fatal VT/VF as compared to the presence of g at the SNP position. Patients with genotype a/a have about a 70% probability of experiencing fatal VT/VF, while the a/g genotype indicates about a 50% probability of experiencing fatal VT/VF, and the g/g genotype indicates about a 35% probability of experiencing fatal VT/VF.

rs2121081 is located at position chr2:155530837, Build 123, within the KCNJ3 gene (Accession No. NT_05403), which codes for the potassium inwardly-rectifying channel, subfamily J, member 3 protein. The protein plays a role in regulating the heartbeat. The SNP and its flanking regions were amplified using primers 5'-agg tga tga aag aaa tga acc ttt-3' (SEQ ID NO. 90) and 5'-tag agc tgg gat gcg gcc-3' (SEQ ID NO. 91). The SNP was sequenced using the oligo 5'-aga tag agt cga tgc cag ctg tcg tct gac acc aca gta ctt act-3' (SEQ ID NO. 92). Table 35 shows the statistical breakdown of the genotypes for this SNP.

TABLE 35

| Count<br>Total (%)<br>Column (%)<br>Row (%) | CONTROL | ICD | Total |
|---|---|---|---|
| c/c | 14<br>15.6%<br>26.9%<br>48.3% | 15<br>16.7%<br>39.5%<br>51.7% | 29<br>32.2% |
| c/g | 24<br>26.7%<br>46.2%<br>54.6% | 20<br>22.2%<br>52.6%<br>45.5% | 44<br>48.9% |
| g/g | 14<br>15.6%<br>26.9%<br>82.4% | 3<br>3.3%<br>7.9%<br>17.7% | 17<br>18.9% |
| Total | 52<br>57.8% | 38<br>42.2% | 90 |

Figure 14:
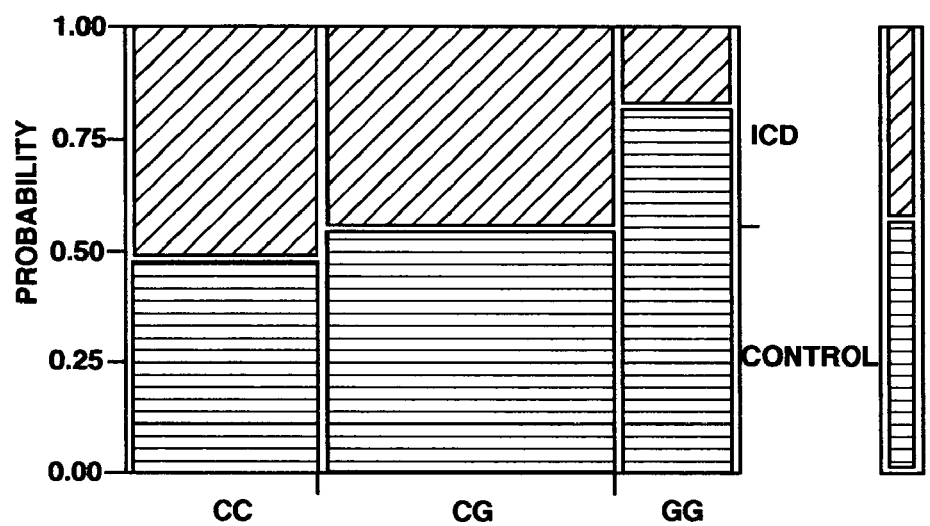
FIG. 14 is a mosaic plot illustrating the probability of experiencing fatal VT/VF as a function of allele specific inheritance of SNP rs2121081.

The information in Table 35 was used to calculate probabilities of patient VT/VF. FIG. 14 is a mosaic plot illustrating the resulting risk stratification.

As shown in the plot, the presence of c at the SNP position indicates increased susceptibility to fatal VT/VF as compared to the presence of g at the SNP position. Patients with genotype g/g have about an 85% probability of not experiencing fatal VT/VF, while the c/g genotype indicates about a 55% probability of not experiencing fatal VT/VF, and the c/c genotype indicates just under a 50% probability of not experiencing fatal VT/VF.

rs1428568 was previously described. Table 36 shows the statistical breakdown of the genotypes for this SNP.

TABLE 36

| Count<br>Total (%)<br>Column (%)<br>Row (%) | CONTROL | ICD | Total |
|---|---|---|---|
| t/t | 9<br>10.5%<br>18.8%<br>42.9% | 12<br>14.0%<br>31.6%<br>57.1% | 21<br>24.4% |
| t/a | 22<br>25.6%<br>45.8%<br>56.4% | 17<br>19.8%<br>44.7%<br>43.6% | 39<br>45.4% |
| a/a | 17<br>19.8%<br>35.4%<br>65.4% | 9<br>10.5%<br>23.7%<br>34.6% | 26<br>30.2% |
| Total | 48<br>55.8% | 38<br>44.2% | 86 |

Figure 15:
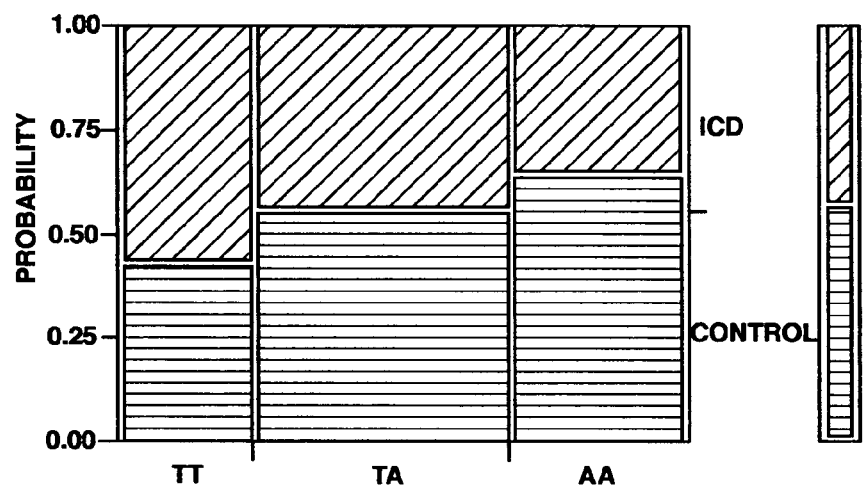
FIG. 15 is a mosaic plot illustrating the probability of experiencing fatal VT/VF as a function of allele specific inheritance of SNP rs1428568.

The information in Table 36 was used to calculate probabilities of patient VT/VF. FIG. 15 is a mosaic plot illustrating the resulting risk stratification.

As shown in the plot, the presence of a at the SNP position indicates decreased susceptibility to fatal VT/VF as compared to the presence of t at the SNP position. Patients with genotype a/a have about a 65% probability of not experiencing fatal VT/VF, while the t/a genotype indicates about a 55% probability of not experiencing fatal VT/VF, and the t/t genotype indicates about a 40% probability of not experiencing fatal VT/VF.

rs918050 was previously described. Table 37 shows the statistical breakdown of the genotypes for this SNP.

TABLE 37

| Count<br>Total (%)<br>Column (%)<br>Row (%) | CONTROL | ICD | Total |
|---|---|---|---|
| g/g | 6<br>7.2%<br>12.5%<br>42.9% | 8<br>9.6%<br>22.9%<br>57.1% | 14<br>16.9% |
| g/a | 16<br>19.3%<br>33.3%<br>55.2% | 13<br>15.7%<br>37.1%<br>44.8% | 29<br>34.9% |
| a/a | 26<br>31.3%<br>54.2%<br>65.0% | 14<br>16.9%<br>40.0%<br>35.0% | 40<br>48.2% |
| Total | 48<br>57.8% | 35<br>42.2% | 83 |

Figure 16:
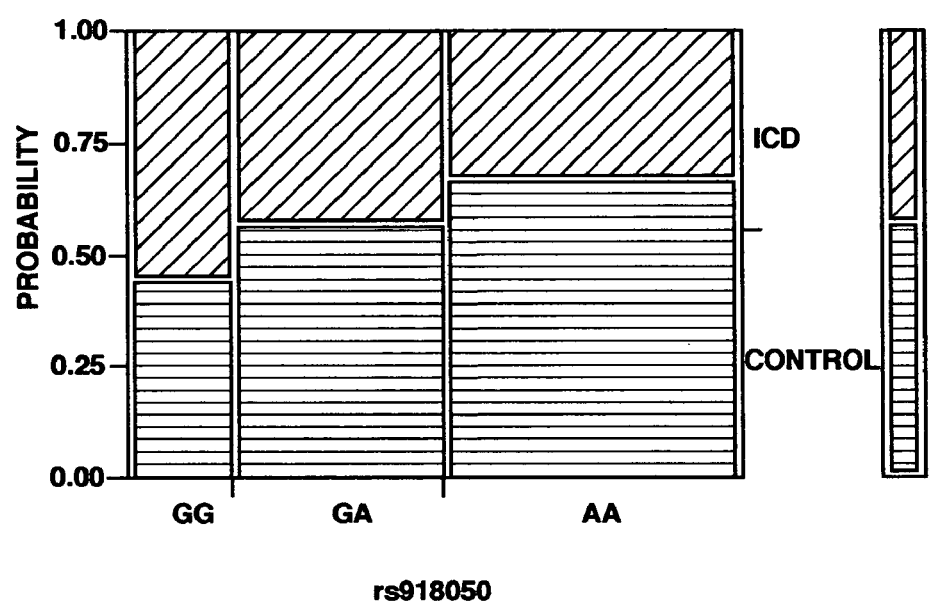
FIG. 16 is a mosaic plot illustrating the probability of experiencing fatal VT/VF as a function of allele specific inheritance of SNP rs918050.

The information in Table 37 was used to calculate probabilities of patient VT/VF. FIG. 16 is a mosaic plot illustrating the resulting risk stratification.

As shown in the plot, the presence of a at the SNP position indicates decreased susceptibility to fatal VT/VF as compared to the presence of g at the SNP position. Patients with genotype a/a have about a 65% probability of not experiencing fatal VT/VF, while the g/a genotype indicates about a 55% probability of not experiencing fatal VT/VF, and the g/g genotype indicates about a 40% probability of not experiencing fatal VT/VF.

rs1483312 is located at position chr5:45550841, Build 123, within the HCN1 gene (Accession No. NT_006576), which codes for the hyperpolarization activated cyclic nucleotide-gated potassium channel 1 protein. The protein contributes spontaneous rhythmic activity in the heart. The SNP and its flanking regions were amplified using primers 5'-tat cct aaa aat cct get tta att tg-3' (SEQ ID NO. 93) and 5'-tac atc tag ttg tat agt tct tat ctc taa att atc-3' (SEQ ID NO. 94). The SNP was sequenced using the oligo 5'-ggc tat gat tcg caa tgc ttg aaa gca tat tac caa taa aaa tta-3' (SEQ ID NO. 95). Table 38 shows the statistical breakdown of the genotypes for this SNP.

TABLE 38

| Count<br>Total (%)<br>Column (%)<br>Row (%) | CONTROL | ICD | Total |
|---|---|---|---|
| t/t | 2<br>2.3%<br>3.9%<br>25.0% | 6<br>6.7%<br>16.2%<br>75.0% | 8<br>9.0% |
| t/a | 16<br>18.0%<br>30.8%<br>50.0% | 16<br>18.0%<br>43.2%<br>50.0% | 32<br>36.0% |

TABLE 38-continued

| Count<br>Total (%)<br>Column (%)<br>Row (%) | CONTROL | ICD | Total |
|---|---|---|---|
| a/a | 34<br>38.2%<br>65.4%<br>69.4% | 15<br>16.9%<br>40.5%<br>30.6% | 49<br>55.1% |
| Total | 52<br>58.4% | 37<br>41.6% | 89 |

Figure 17:
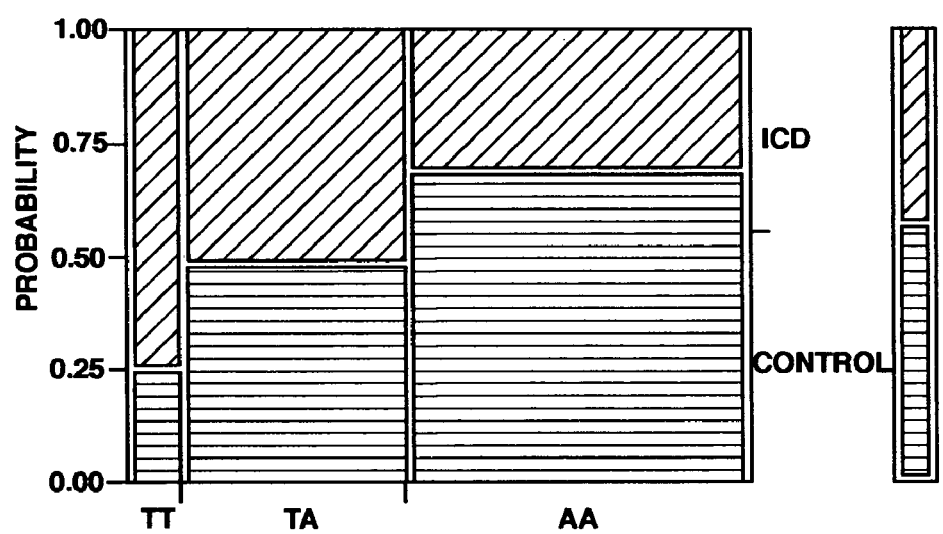
FIG. 17 is a mosaic plot illustrating the probability of experiencing fatal VT/VF as a function of allele specific inheritance of SNP rs1483312.

The information in Table 38 was used to calculate probabilities of patient VT/VF. FIG. 17 is a mosaic plot illustrating the resulting risk stratification.

As shown in the plot, the presence of a at the SNP position indicates decreased susceptibility to fatal VT/VF as compared to the presence of t at the SNP position. Patients with genotype a/a have about a 70% probability of not experiencing fatal VT/VF, while the t/a genotype indicates about a 50% probability of not experiencing fatal VT/VF, and the t/t genotype indicates about a 25% probability of not experiencing fatal VT/VF.

rs1859037 is located at position chr7:90526702, Build 120, within the AKAP9 gene Accession No. NT_007933), which codes for the A-kinase (PRKA) anchor protein (yotiao) 9. The protein binds to the regulatory subunit of protein kinase A and confines the holoenzyme to discrete locations in a cell. The SNP and its flanking regions were amplified using primers 5'-aat taa tga ttg gta tga caa gtt atg a-3' (SEQ ID NO. 96) and 5'-tga aag tta gat ttg tgt taa ctt cta tta g-3' (SEQ ID NO. 97). The SNP was sequenced using the oligo 5'-gac ctg ggt gtc gat acc taa tag gtg cca taa gga aga gtc aga-3' (SEQ ID NO. 98). Table 39 shows the statistical breakdown of the genotypes for this SNP.

TABLE 39

| Count<br>Total (%)<br>Column (%)<br>Row (%) | CONTROL | ICD | Total |
|---|---|---|---|
| g/g | 22<br>24.7%<br>43.1%<br>66.7% | 11<br>12.4%<br>29.0%<br>33.3% | 33<br>37.1% |
| g/a | 23<br>25.8%<br>45.1%<br>53.5% | 20<br>22.5%<br>52.6%<br>46.5% | 43<br>48.3% |
| a/a | 6<br>6.7%<br>11.8%<br>46.2% | 7<br>7.9%<br>18.4%<br>53.9% | 13<br>14.6% |
| Total | 51<br>57.3% | 38<br>42.7% | 89 |

Figure 18:
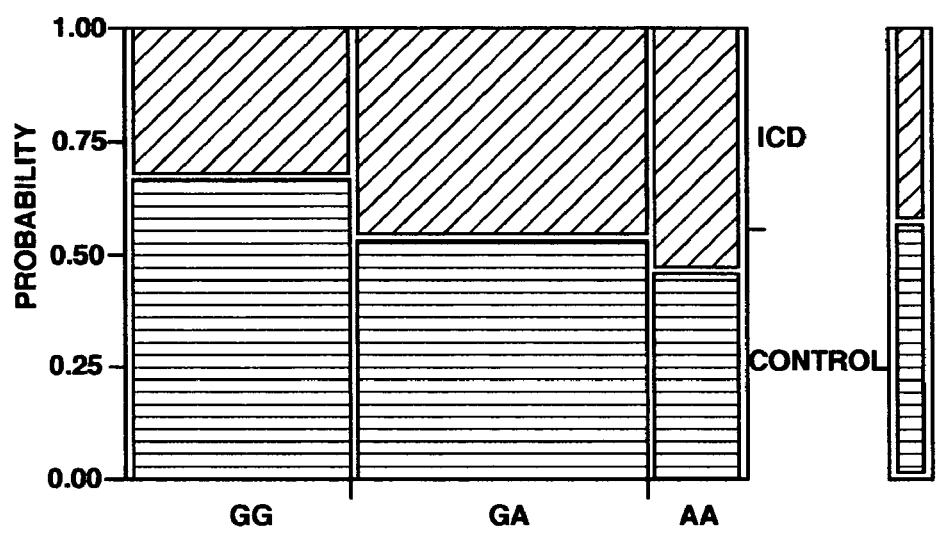
FIG. 18 is a mosaic plot illustrating the probability of experiencing fatal VT/VF as a function of allele specific inheritance of SNP rs1859037.

The information in Table 39 was used to calculate probabilities of patient VT/VF. FIG. 18 is a mosaic plot illustrating the resulting risk stratification.

As shown in the plot, the presence of g at the SNP position indicates decreased susceptibility to fatal VT/VF as compared to the presence of a at the SNP position. Patients with genotype g/g have about a 65% probability of not experiencing fatal VT/VF, while the g/a genotype indicates about a 50% probability of not experiencing fatal VT/VF, and the a/a genotype indicates about a 45% probability of not experiencing fatal VT/VF.

rs6964587 is located at position chr7:90588196, Build 123, within the AKAP9 gene (Accession No. NT_007933), which codes for the A-kinase (PRKA) anchor protein (yotiao) 9. This function of the protein is described above. The SNP and its flanking regions were amplified using primers 5'-gtg caa atg aaa caa gaa tta ata ag-3' (SEQ ID NO. 99) and 5'-aat atg acc tta aag cat tct cca-3' (SEQ ID NO. 100). The SNP was sequenced using the oligo 5'-cgt gcc gct cgt gat aga ata aca cat ggc aca gat gga gga aat-3' (SEQ ID NO. 101). Table 40 shows the statistical breakdown of the genotypes for this SNP.

TABLE 40

| Count<br>Total (%)<br>Column (%)<br>Row (%) | CONTROL | ICD | Total |
|---|---|---|---|
| g/g | 5<br>5.7%<br>10.0%<br>41.7% | 7<br>8.0%<br>18.4%<br>58.3% | 12<br>13.6% |
| g/t | 23<br>26.1%<br>46.0%<br>53.5% | 20<br>22.7%<br>52.6%<br>46.5% | 43<br>48.9% |
| t/t | 22<br>25.0%<br>44.0%<br>66.7% | 11<br>12.5%<br>29.0%<br>33.3% | 33<br>37.5% |
| Total | 50<br>56.8% | 38<br>43.2& | 88 |

Figure 19:
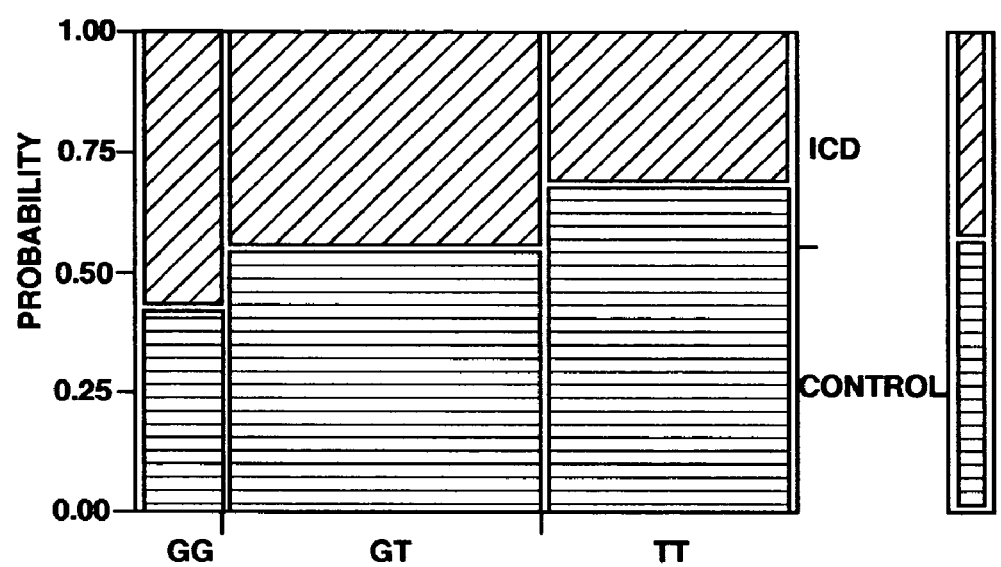
FIG. 19 is a mosaic plot illustrating the probability of experiencing fatal VT/VF as a function of allele specific inheritance of SNP rs6964587.

The information in Table 40 was used to calculate probabilities of patient VT/VF. FIG. 19 is a mosaic plot illustrating the resulting risk stratification.

As shown in the plot, the presence of t at the SNP position indicates decreased susceptibility to fatal VT/VF as compared to the presence of g at the SNP position. Patients with genotype t/t have about a 65% probability of not experiencing fatal VT/VF, while the g/t genotype indicates about a 55% probability of not experiencing fatal VT/VF, and the g/g genotype indicates about a 40% probability of not experiencing fatal VT/VF.

Each of these SNP tests can be used individually as class identifiers, or two or more SNP tests may be combined to improve the predictive power.

Figure 20:
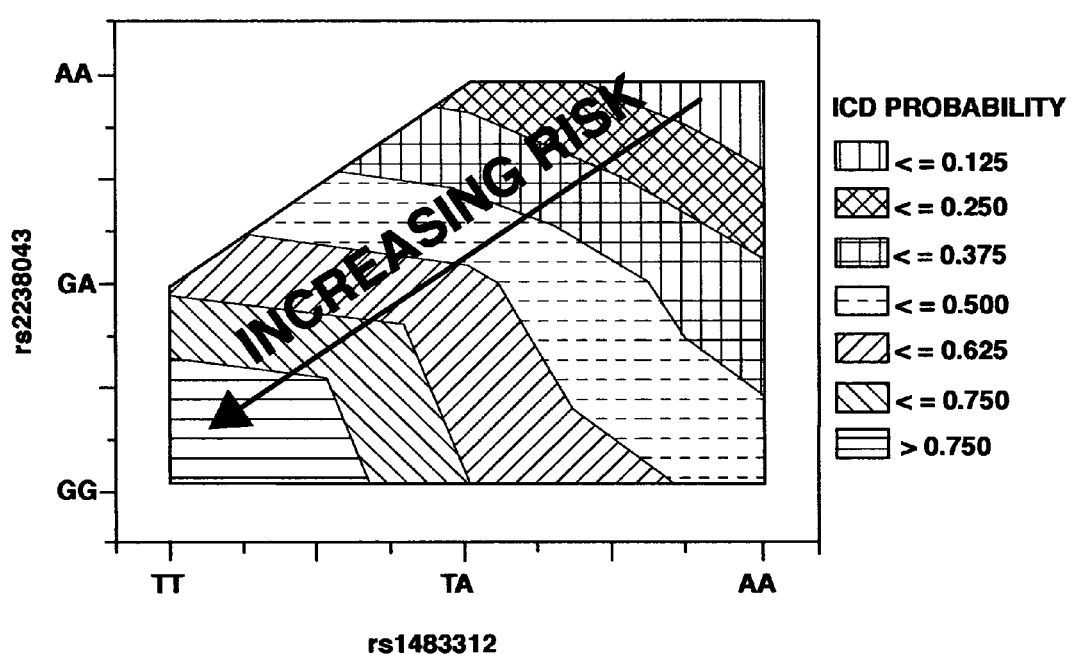
FIG. 20 is a graph illustrating the probability of experiencing fatal VT/VF as a function of allele specific inheritance of SNPs rs1483312 and rs2238043.

FIG. 20 is a contour plot showing the probability of experiencing VT/VF as a function of the allele specific inheritance pattern of SNPs rs2238043 and rs1483312. The horizontal axis is the possible genotypes of rs1483312, and the vertical axis is the possible genotypes of rs2238043. Matrixes were formed where the points of intersection are the points of interest. The box next to the plot identifies the probabilities that correspond to the intersection points.

The genotype combinations further stratify the patient probabilities to classify patients. For example, a patient having a genotype profile of t/t-g/g has a greater than 75% probability of experiencing VT/VF, while a patient having a genotype profile of t/a-g/a has a less than or equal to 62.5% probability. A patient having a genotype profile of a/a-g/a has a less than or equal to 37.5% probability of experiencing VT/VF, while a patient having a genotype profile of a/a/-a/a has a less than or equal to 12.5% probability.

Target Identification

The present invention may also be used to identify targets for therapy as shown by step 40 of Classification process 10

(FIG. 1). Class identifiers identified at step 22 are studied to determine whether they may be targets for therapy.

If a newly discovered class identifier for a given disease is a protein marker, for example, there is a possibility that the protein marker plays a pivotal role in the disease pathway. Depending on whether the protein level is too high or too low in the disease state, protein levels may be increased or decreased to compensate for the atypical levels. This may be accomplished directly or indirectly through gene therapy to upregulate or downregulate protein expression or by injecting more of the protein to increase levels. Other factors, such as enzymes or antibodies, can be injected or induced to effectively decrease the protein levels.

The protein can also be studied to identify pharmaceutical drugs that act on the protein and resolve the disease or condition. In addition, even if it is determined that the protein is not directly involved in the condition's pathway, the protein can be studied to determine other factors that interact with it, which may lead to effective therapeutic targets.

Genomic data may identify a mutation, polymorphism, deletion, or repetition in a specific gene as a class identifier for a given disease or condition. Therapy can be applied at the genotypic level, such as through gene therapy. It may also be delivered at a phenotypic level, such as through the delivery of drugs.

Lipidomic data may identify atypical levels of or alterations in an insoluble blood serum factor. Again, this may be a target for drug therapy or gene therapy. If it is determined that the class identifier is not involved in the condition's pathway, studying the insoluble blood serum factor may lead to other factors that are effective targets.

Analysis of physiological data may discover a class identifier based on the electrical data gathered from the patient, such as a particular heart arrhythmia. An IMD may be utilized as a therapy for the particular condition.

A number of genes were identified and described above which may be involved in disease conditions that cause VT/VF. These may directly or indirectly be targets for therapy. In addition, other SNPs were identified whose genes were not listed, but which could also be used to find targets for therapy or study.

Improve Treatment Therapies

The present invention can also be used to improve treatment therapies. Class identifiers may be discovered that are based on specimens receiving a specific treatment versus not receiving the treatment. These class identifiers can be studied to provide insight into improving the treatment.

For example, recent evidence shows that VT/VF is treatable by administration of clonidine or vagal nerve stimulation, as well as through stimulation by an implantable cardioverter defibrillator (ICD). Thus, class identifiers may be used to identify patients that would benefit from these treatments and/or benefit from IMDs such as a drug pump to deliver intrathecal clonidine, a vagal nerve stimulator, or an ICD.

In this embodiment, information and data from specimens are gathered from samples prior to the specimen receiving a treatment. The specimens are classified based on being a candidate for therapy and class identifiers are identified.

Next, the specimens receive treatment. Follow-up information and data from specimens are gathered following treatment. The follow-up data also includes the classification of the specimen as to whether or not the specimen responded favorably to the treatment. The classification of the specimens is corrected based on the follow-up data.

Class identifiers are identified based on differences between specimens that responded favorably and specimens that did not respond favorably. Those class identifiers are studied further as potential targets for improving the treatment.

Some of the processes described above may be embodied as a computer-readable medium comprising instructions for a programmable processor. The programmable processor may include one or more individual processors, which may act independently or in concert. A "computer-readable medium" includes but is not limited to read-only memory, Flash memory, and a magnetic or optical storage medium. Furthermore, data can be transmitted over the Internet, local area networks, or wireless or land base telephone lines.

The present invention should reduce the number of false positives and false negatives. The invention is also self-improving in two ways. The addition of specimen profiles to the database and correctly classifying specimens or patients if initially incorrectly classified refine the algorithms to improve classification process 10.

Although the present invention has been described with reference to preferred embodiments, workers skilled in the art will recognize that changes may be made in form and detail without departing from the spirit and scope of the invention.

The invention claimed is:

1. A self improving method of classifying a specimen from a patient at possible risk of ventricular tachyarrhythmia/ventricular fibrillation (VT/VF), the method comprising:
   using an algorithm, by a computer, for classifying specimens based on at least one class identifier, wherein said class identifier includes a Single Nucleotide Polymorphism (SNP), the SNP selected from the group consisting of SEQ ID NO.'s 1-83 and 102;
   generating a specimen profile from the specimen by analyzing the genomic information of the specimen and storing, by a computer, the specimen profile in a database;
   classifying, based on the specimen profile, the specimen into a class of being from a patient at possible risk of VT/VF; the classifying being carried out using the algorithm;
   determining if reclassification of the specimen is necessary;
   refining the algorithm based on a refinement of the at least one class identifier, and
   reclassifying the specimen if necessary, by a computer.

2. The self-improving method of classifying a specimen of claim 1 wherein the specimen profile includes data selected from a group consisting of demographic, historical, psychiatric, physiological, pathological, metabolic, genomic, proteomic, and lipidomic information.

3. The self-improving method of classifying a specimen of claim 1 wherein the class identifier is based on a class distinction of previously classified specimens.

4. The self-improving method of classifying a specimen of claim 1 wherein the specimen is a person.

5. The self-improving method of classifying a specimen of claim 1 wherein refining the algorithm comprises: identifying new class identifiers.

6. The self-improving method of classifying a specimen of claim 1 wherein the algorithm is based on a plurality of class identifiers.

7. The self-improving method of classifying a specimen of claim 1, wherein determining if reclassification of the specimen is necessary is based on follow-up data.

8. The self-improving method of classifying a specimen of claim 1, wherein said algorithm is a type selected from the group consisting of linear, non-linear, and logical algorithms.

9. The self-improving method of classifying a specimen of claim 1, wherein the algorithm evaluates if a patient had no prior stent and has an a/a genotype of the Single Nucleotide Polymorphism (SNP) represented by SEQ ID NO. 30, then the patient is placed in a first group for those patients deemed not at risk of ventricular tachyarrhythmia, whereas if the patient had no prior stent and has a g/a or g/g genotype of SEQ ID NO. 30, then the patient is placed in a second group for further partitioning.

10. The self-improving method of classifying a specimen of claim 9, wherein if the patient has the g/a or g/g genotype of SEQ ID NO. 30, and has a c/c or t/c genotype of the Single Nucleotide Polymorphism (SNP) represented by SEQ ID NO. 105, then the patient is placed in a third group for those patients deemed to be at risk of ventricular tachyarrhythmia, whereas if the patient has a t/t genotype of SEQ ID NO. 105, then the patient is placed in a fourth group for further partitioning.

11. The self-improving method of classifying a specimen of claim 10, wherein if the patient has the t/t genotype of SEQ ID NO. 105, and has g/g genotype of the Single Nucleotide Polymorphism (SNP) represented by SEQ ID NO. 81, then the patient is placed in a fifth group for those patients deemed not at risk of ventricular tachyarrhythmia, whereas if the patient has a g/a or a/a genotype of SEQ ID NO. 81, then the patient is placed in a sixth group for further partitioning.

12. The self-improving method of classifying a specimen of claim 11, wherein if the patient has the g/a or a/a genotype of SEQ ID NO. 81, and has a g/g genotype of the Single Nucleotide Polymorphism (SNP) represented by SEQ ID NO. 63, then the patient is placed in a seventh group for those patients deemed at risk of ventricular tachyarrhythmia, whereas if the patient has an a/a or g/a genotype of SEQ ID NO. 63 then the patient is placed in an eighth group for further partitioning.

13. The self-improving method of classifying a specimen of claim 12, wherein if the patient has the a/a or g/a genotype of SEQ ID NO. 63, and has a g/g genotype of the Single Nucleotide Polymorphism (SNP) represented by SEQ ID NO. 102, then the patient is placed in a ninth group of patients deemed at risk of ventricular tachyarrhythmia, whereas if the patient has an a/a or g/a genotype of SEQ ID NO. 102 then the patient is placed in a tenth group of patients deemed not at risk of ventricular tachyarrhythmia.

* * * * *

SEQUENCE LISTING

<160> NUMBER OF SEQ ID NOS: 105

<210> SEQ ID NO 1
<211> LENGTH: 23
<212> TYPE: DNA
<213> ORGANISM: Homo sapiens

<400> SEQUENCE: 1
agtcaggatc aggtattttt cct                                    23

<210> SEQ ID NO 2
<211> LENGTH: 19
<212> TYPE: DNA
<213> ORGANISM: Homo sapiens

<400> SEQUENCE: 2
agaacccagg tgaaccaat                                         19

```
<210> SEQ ID NO 3
<211> LENGTH: 45
<212> TYPE: DNA
<213> ORGANISM: Homo sapiens

<400> SEQUENCE: 3
agatagagtc gatgccagct tcatgggtct ctgacctcac tgtct          45

<210> SEQ ID NO 4
<211> LENGTH: 18
<212> TYPE: DNA
<213> ORGANISM: Homo sapiens

<400> SEQUENCE: 4
cctccggatt ccaggacc                                        18

<210> SEQ ID NO 5
<211> LENGTH: 18
<212> TYPE: DNA
<213> ORGANISM: Homo sapiens

<400> SEQUENCE: 5
ttccgctttc cactgctg                                        18

<210> SEQ ID NO 6
<211> LENGTH: 45
<212> TYPE: DNA
<213> ORGANISM: Homo sapiens

<400> SEQUENCE: 6
ggatggcgtt ccgtcctatt agatgcactg gcctcggcct cagag          45

<210> SEQ ID NO 7
<211> LENGTH: 25
<212> TYPE: DNA
<213> ORGANISM: Homo sapiens

<400> SEQUENCE: 7
attgtgttca tttagagaaa cagct                                25

<210> SEQ ID NO 8
<211> LENGTH: 18
<212> TYPE: DNA
<213> ORGANISM: Homo sapiens

<400> SEQUENCE: 8
cttctgaggc tccccagg                                        18

<210> SEQ ID NO 9
<211> LENGTH: 45
<212> TYPE: DNA
<213> ORGANISM: Homo sapiens

<400> SEQUENCE: 9
agggtctcta cgctgacgat ctgtaacttg gagctccact ctgcc          45

<210> SEQ ID NO 10
<211> LENGTH: 22
<212> TYPE: DNA
<213> ORGANISM: Homo sapiens

<400> SEQUENCE: 10
tcagtaggaa atgaaggctt tt                                   22
```

```
<210> SEQ ID NO 11
<211> LENGTH: 19
<212> TYPE: DNA
<213> ORGANISM: Homo sapiens

<400> SEQUENCE: 11
atttcaggga acgaatgga                                               19

<210> SEQ ID NO 12
<211> LENGTH: 45
<212> TYPE: DNA
<213> ORGANISM: Homo sapiens

<400> SEQUENCE: 12
gcggtaggtt cccgacatat tcttcaagca gcgggagggg gtggc                  45

<210> SEQ ID NO 13
<211> LENGTH: 24
<212> TYPE: DNA
<213> ORGANISM: Homo sapiens

<400> SEQUENCE: 13
acaaactcaa aggaaaacca taca                                         24

<210> SEQ ID NO 14
<211> LENGTH: 20
<212> TYPE: DNA
<213> ORGANISM: Homo sapiens

<400> SEQUENCE: 14
atctcgtcat ggcactgagt                                              20

<210> SEQ ID NO 15
<211> LENGTH: 45
<212> TYPE: DNA
<213> ORGANISM: Homo sapiens

<400> SEQUENCE: 15
gtgattctgt acgtgtcgcc tgggttgttg aatgatactt cagca                  45

<210> SEQ ID NO 16
<211> LENGTH: 21
<212> TYPE: DNA
<213> ORGANISM: Homo sapiens

<400> SEQUENCE: 16
aataggatgc acttgcttga c                                            21

<210> SEQ ID NO 17
<211> LENGTH: 21
<212> TYPE: DNA
<213> ORGANISM: Homo sapiens

<400> SEQUENCE: 17
atgaggaaga gtcccttcac c                                            21

<210> SEQ ID NO 18
<211> LENGTH: 45
<212> TYPE: DNA
<213> ORGANISM: Homo sapiens

<400> SEQUENCE: 18
agggtctcta cgctgacgat tgatgttcat tgatggggac aggca                  45
```

```
<210> SEQ ID NO 19
<211> LENGTH: 23
<212> TYPE: DNA
<213> ORGANISM: Homo sapiens

<400> SEQUENCE: 19
tatctgtcac ttctacaacc gct                                          23

<210> SEQ ID NO 20
<211> LENGTH: 22
<212> TYPE: DNA
<213> ORGANISM: Homo sapiens

<400> SEQUENCE: 20
aattccaagg aggaggaata ca                                           22

<210> SEQ ID NO 21
<211> LENGTH: 45
<212> TYPE: DNA
<213> ORGANISM: Homo sapiens

<400> SEQUENCE: 21
gcggtaggtt cccgacatat atcgggccac tgaacaaaac ggcaa                  45

<210> SEQ ID NO 22
<211> LENGTH: 18
<212> TYPE: DNA
<213> ORGANISM: Homo sapiens

<400> SEQUENCE: 22
atgcacagca tgtggctc                                                18

<210> SEQ ID NO 23
<211> LENGTH: 18
<212> TYPE: DNA
<213> ORGANISM: Homo sapiens

<400> SEQUENCE: 23
tgagcacctg cccaccac                                                18

<210> SEQ ID NO 24
<211> LENGTH: 45
<212> TYPE: DNA
<213> ORGANISM: Homo sapiens

<400> SEQUENCE: 24
agggtctcta cgctgacgat tgcagaacca ctcgtggagt gaact                  45

<210> SEQ ID NO 25
<211> LENGTH: 24
<212> TYPE: DNA
<213> ORGANISM: Homo sapiens

<400> SEQUENCE: 25
agtaaagcat tatggaggca taaa                                         24

<210> SEQ ID NO 26
<211> LENGTH: 28
<212> TYPE: DNA
<213> ORGANISM: Homo sapiens

<400> SEQUENCE: 26
gcatctaagt tctcctaaat ttttatt                                      28
```

```
<210> SEQ ID NO 27
<211> LENGTH: 45
<212> TYPE: DNA
<213> ORGANISM: Homo sapiens

<400> SEQUENCE: 27
ggctatgatt cgcaatgctt gtttggatta tgacatcatt ctata            45

<210> SEQ ID NO 28
<211> LENGTH: 20
<212> TYPE: DNA
<213> ORGANISM: Homo sapiens

<400> SEQUENCE: 28
tttttctttc agaagcccct                                        20

<210> SEQ ID NO 29
<211> LENGTH: 20
<212> TYPE: DNA
<213> ORGANISM: Homo sapiens

<400> SEQUENCE: 29
acatgacatg gtgacaagca                                        20

<210> SEQ ID NO 30
<211> LENGTH: 45
<212> TYPE: DNA
<213> ORGANISM: Homo sapiens

<400> SEQUENCE: 30
cgtgccgctc gtgatagaat tctttgtcaa ttgactttt ctccc             45

<210> SEQ ID NO 31
<211> LENGTH: 24
<212> TYPE: DNA
<213> ORGANISM: Homo sapiens

<400> SEQUENCE: 31
aagaaaaaat acaaagacag tggc                                   24

<210> SEQ ID NO 32
<211> LENGTH: 21
<212> TYPE: DNA
<213> ORGANISM: Homo sapiens

<400> SEQUENCE: 32
tgtcaaaacc tttggttcaa a                                      21

<210> SEQ ID NO 33
<211> LENGTH: 45
<212> TYPE: DNA
<213> ORGANISM: Homo sapiens

<400> SEQUENCE: 33
agggtctcta cgctgacgat ttgttaagcc tccttcccgt tattc             45

<210> SEQ ID NO 34
<211> LENGTH: 26
<212> TYPE: DNA
<213> ORGANISM: Homo sapiens

<400> SEQUENCE: 34 cattttaca gacaagaaaa tttagg                                   26
```

```
<210> SEQ ID NO 35
<211> LENGTH: 20
<212> TYPE: DNA
<213> ORGANISM: Homo sapiens

<400> SEQUENCE: 35
ataggttttt ctctccagcc                                              20

<210> SEQ ID NO 36
<211> LENGTH: 45
<212> TYPE: DNA
<213> ORGANISM: Homo sapiens

<400> SEQUENCE: 36
acgcacgtcc acggtgattt cttggctgca gaacctctgg ctaag                  45

<210> SEQ ID NO 37
<211> LENGTH: 25
<212> TYPE: DNA
<213> ORGANISM: Homo sapiens

<400> SEQUENCE: 37
cataaatctt aactttagc gatcg                                         25

<210> SEQ ID NO 38
<211> LENGTH: 29
<212> TYPE: DNA
<213> ORGANISM: Homo sapiens

<400> SEQUENCE: 38
aggatcgttt tctagataca aatgtataa                                    29

<210> SEQ ID NO 39
<211> LENGTH: 45
<212> TYPE: DNA
<213> ORGANISM: Homo sapiens

<400> SEQUENCE: 39
agcgatctgc gagaccgtat gatatggtct agatcaacaa taatt                  45

<210> SEQ ID NO 40
<211> LENGTH: 29
<212> TYPE: DNA
<213> ORGANISM: Homo sapiens

<400> SEQUENCE: 40
aaaactataa gtattttctt gtgaaggtg                                    29

<210> SEQ ID NO 41
<211> LENGTH: 19
<212> TYPE: DNA
<213> ORGANISM: Homo sapiens

<400> SEQUENCE: 41
aacatttgcc aatgcaatg                                               19

<210> SEQ ID NO 42
<211> LENGTH: 45
<212> TYPE: DNA
<213> ORGANISM: Homo sapiens

<400> SEQUENCE: 42
ggatggcgtt ccgtcctatt agcagcattt aaataaatgc cctct                  45
```

```
<210> SEQ ID NO 43
<211> LENGTH: 23
<212> TYPE: DNA
<213> ORGANISM: Homo sapiens

<400> SEQUENCE: 43
aaaatgttca gcttgtaatt cca                                      23

<210> SEQ ID NO 44
<211> LENGTH: 25
<212> TYPE: DNA
<213> ORGANISM: Homo sapiens

<400> SEQUENCE: 44
tagaagctag agaggaaagt gacaa                                    25

<210> SEQ ID NO 45
<211> LENGTH: 45
<212> TYPE: DNA
<213> ORGANISM: Homo sapiens

<400> SEQUENCE: 45
agggtctcta cgctgacgat cccccaaag ctagtgttta gctct               45

<210> SEQ ID NO 46
<211> LENGTH: 18
<212> TYPE: DNA
<213> ORGANISM: Homo sapiens

<400> SEQUENCE: 46
aagagccatg tgggccat                                            18

<210> SEQ ID NO 47
<211> LENGTH: 23
<212> TYPE: DNA
<213> ORGANISM: Homo sapiens

<400> SEQUENCE: 47
aatattttca agagtatggg gca                                      23

<210> SEQ ID NO 48
<211> LENGTH: 45
<212> TYPE: DNA
<213> ORGANISM: Homo sapiens

<400> SEQUENCE: 48
agagcgagtg acgcatacta tttcagctca gtttattttt atggt              45

<210> SEQ ID NO 49
<211> LENGTH: 22
<212> TYPE: DNA
<213> ORGANISM: Homo sapiens

<400> SEQUENCE: 49
ataattggga gctggagtag ct                                       22

<210> SEQ ID NO 50
<211> LENGTH: 23
<212> TYPE: DNA
<213> ORGANISM: Homo sapiens

<400> SEQUENCE: 50
tcagaggaca cagtatctaa ggc                                      23
```

<210> SEQ ID NO 51
<211> LENGTH: 45
<212> TYPE: DNA
<213> ORGANISM: Homo sapiens

<400> SEQUENCE: 51
cgtgccgctc gtgatagaat atcttagtaa taatcccaag caaac    45

<210> SEQ ID NO 52
<211> LENGTH: 19
<212> TYPE: DNA
<213> ORGANISM: Homo sapiens

<400> SEQUENCE: 52
ttgtgctggt gtacctcga    19

<210> SEQ ID NO 53
<211> LENGTH: 19
<212> TYPE: DNA
<213> ORGANISM: Homo sapiens

<400> SEQUENCE: 53
agaaggagta aaggcagcc    19

<210> SEQ ID NO 54
<211> LENGTH: 45
<212> TYPE: DNA
<213> ORGANISM: Homo sapiens

<400> SEQUENCE: 54
cgtgccgctc gtgatagaat ggcagatgat ttgttgagca gaatg    45

<210> SEQ ID NO 55
<211> LENGTH: 26
<212> TYPE: DNA
<213> ORGANISM: Homo sapiens

<400> SEQUENCE: 55
agtcaagtcc agtccacagt aatata    26

<210> SEQ ID NO 56
<211> LENGTH: 29
<212> TYPE: DNA
<213> ORGANISM: Homo sapiens

<400> SEQUENCE: 56
aaaatactta aggatatact ctaaaggca    29

<210> SEQ ID NO 57
<211> LENGTH: 45
<212> TYPE: DNA
<213> ORGANISM: Homo sapiens

<400> SEQUENCE: 57
agggtctcta cgctgacgat atgtgtgttt gtgcttttta gatta    45

<210> SEQ ID NO 58
<211> LENGTH: 27
<212> TYPE: DNA
<213> ORGANISM: Homo sapiens

<400> SEQUENCE: 58
atttcaactt aagtattgaa tccaaag    27

<210> SEQ ID NO 59
<211> LENGTH: 28
<212> TYPE: DNA
<213> ORGANISM: Homo sapiens

<400> SEQUENCE: 59 gttttttct cttatctttc ttttgttc                                28

<210> SEQ ID NO 60
<211> LENGTH: 45
<212> TYPE: DNA
<213> ORGANISM: Homo sapiens

<400> SEQUENCE: 60
agcgatctgc gagaccgtat tttttctatg gttcttatgg ctata            45

<210> SEQ ID NO 61
<211> LENGTH: 22
<212> TYPE: DNA
<213> ORGANISM: Homo sapiens

<400> SEQUENCE: 61
ataaagaaag gagggcaagt gt                                     22

<210> SEQ ID NO 62
<211> LENGTH: 18
<212> TYPE: DNA
<213> ORGANISM: Homo sapiens

<400> SEQUENCE: 62
tcccacctgc ctctgtct                                          18

<210> SEQ ID NO 63
<211> LENGTH: 45
<212> TYPE: DNA
<213> ORGANISM: Homo sapiens

<400> SEQUENCE: 63
cgactgtagg tgcgtaactc aaacagctaa atgcaacaat agcag             45

<210> SEQ ID NO 64
<211> LENGTH: 19
<212> TYPE: DNA
<213> ORGANISM: Homo sapiens

<400> SEQUENCE: 64
aattggttgt cttctgggg                                         19

<210> SEQ ID NO 65
<211> LENGTH: 20
<212> TYPE: DNA
<213> ORGANISM: Homo sapiens

<400> SEQUENCE: 65
attttttggc aagttggaca                                        20

<210> SEQ ID NO 66
<211> LENGTH: 45
<212> TYPE: DNA
<213> ORGANISM: Homo sapiens

<400> SEQUENCE: 66
agcgatctgc gagaccgtat gactggaagg caagacccgc aaagc             45

<210> SEQ ID NO 67
<211> LENGTH: 18
<212> TYPE: DNA
<213> ORGANISM: Homo sapiens

<400> SEQUENCE: 67
ctgtgcagac gcctaagg                                                 18

<210> SEQ ID NO 68
<211> LENGTH: 18
<212> TYPE: DNA
<213> ORGANISM: Homo sapiens

<400> SEQUENCE: 68
tgggctatat tgaagccg                                                 18

<210> SEQ ID NO 69
<211> LENGTH: 45
<212> TYPE: DNA
<213> ORGANISM: Homo sapiens

<400> SEQUENCE: 69
agcgatctgc gagaccgtat gtgaaccgcg ctggagcggc gtagg                   45

<210> SEQ ID NO 70
<211> LENGTH: 28
<212> TYPE: DNA
<213> ORGANISM: Homo sapiens

<400> SEQUENCE: 70
gataaccaag agttaaccat aattacag                                      28

<210> SEQ ID NO 71
<211> LENGTH: 20
<212> TYPE: DNA
<213> ORGANISM: Homo sapiens

<400> SEQUENCE: 71
taagtatgcg tgtccaggaa                                               20

<210> SEQ ID NO 72
<211> LENGTH: 45
<212> TYPE: DNA
<213> ORGANISM: Homo sapiens

<400> SEQUENCE: 72
acgcacgtcc acggtgattt aagtaaaaat aaactaatga tactc                   45

<210> SEQ ID NO 73
<211> LENGTH: 20
<212> TYPE: DNA
<213> ORGANISM: Homo sapiens

<400> SEQUENCE: 73
tactgtgggc aacatttcag                                               20

<210> SEQ ID NO 74
<211> LENGTH: 18
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n is a, c, g, or t

```
<400> SEQUENCE: 74
atnctgcacc ctcttcag                                               18

<210> SEQ ID NO 75
<211> LENGTH: 45
<212> TYPE: DNA
<213> ORGANISM: Homo sapiens

<400> SEQUENCE: 75
ggctatgatt cgcaatgctt ttgggggatt tcccccaaag ccttc                  45

<210> SEQ ID NO 76
<211> LENGTH: 28
<212> TYPE: DNA
<213> ORGANISM: Homo sapiens

<400> SEQUENCE: 76
tgttgtgtat agcttattat gaaactga                                    28

<210> SEQ ID NO 77
<211> LENGTH: 22
<212> TYPE: DNA
<213> ORGANISM: Homo sapiens

<400> SEQUENCE: 77
ttaggcaaaa atgctaccaa tc                                          22

<210> SEQ ID NO 78
<211> LENGTH: 45
<212> TYPE: DNA
<213> ORGANISM: Homo sapiens

<400> SEQUENCE: 78
gcggtaggtt cccgacatat tataaaattt gcagtttgtt tactc                  45

<210> SEQ ID NO 79
<211> LENGTH: 22
<212> TYPE: DNA
<213> ORGANISM: Homo sapiens

<400> SEQUENCE: 79
agtgggctca acttttactg tt                                          22

<210> SEQ ID NO 80
<211> LENGTH: 19
<212> TYPE: DNA
<213> ORGANISM: Homo sapiens

<400> SEQUENCE: 80
gaaagattcc tgtcagggc                                              19

<210> SEQ ID NO 81
<211> LENGTH: 45
<212> TYPE: DNA
<213> ORGANISM: Homo sapiens

<400> SEQUENCE: 81
ggatggcgtt ccgtcctatt aatctttaat aagagaggca gttac                  45

<210> SEQ ID NO 82
<211> LENGTH: 19
<212> TYPE: DNA
<213> ORGANISM: Homo sapiens
```

```
<400> SEQUENCE: 82
agcaggtgag tgtcctttg                                              19

<210> SEQ ID NO 83
<211> LENGTH: 19
<212> TYPE: DNA
<213> ORGANISM: Homo sapiens

<400> SEQUENCE: 83
tggatcccaa aattccttg                                              19

<210> SEQ ID NO 84
<211> LENGTH: 18
<212> TYPE: DNA
<213> ORGANISM: Homo sapiens

<400> SEQUENCE: 84
tgcacatgaa caaagccc                                               18

<210> SEQ ID NO 85
<211> LENGTH: 25
<212> TYPE: DNA
<213> ORGANISM: Homo sapiens

<400> SEQUENCE: 85
aaagttagga aagaagaagc agaat                                       25

<210> SEQ ID NO 86
<211> LENGTH: 45
<212> TYPE: DNA
<213> ORGANISM: Homo sapiens

<400> SEQUENCE: 86
agagcgagtg acgcatacta aggcaggcag caggtgtgag cagat                 45

<210> SEQ ID NO 87
<211> LENGTH: 27
<212> TYPE: DNA
<213> ORGANISM: Homo sapiens

<400> SEQUENCE: 87
atactagaca gagagcaaga cttcaag                                     27

<210> SEQ ID NO 88
<211> LENGTH: 18
<212> TYPE: DNA
<213> ORGANISM: Homo sapiens

<400> SEQUENCE: 88
tccccattca aagtgcct                                               18

<210> SEQ ID NO 89
<211> LENGTH: 45
<212> TYPE: DNA
<213> ORGANISM: Homo sapiens

<400> SEQUENCE: 89
agatagagtc gatgccagct gaagtgagat acctaaggag tgtca                 45

<210> SEQ ID NO 90
<211> LENGTH: 24
<212> TYPE: DNA
<213> ORGANISM: Homo sapiens
```

```
<400> SEQUENCE: 90
aagtgatgaa agaaatgaac cttt                                    24

<210> SEQ ID NO 91
<211> LENGTH: 18
<212> TYPE: DNA
<213> ORGANISM: Homo sapiens

<400> SEQUENCE: 91
tagagctggg atgcggcc                                           18

<210> SEQ ID NO 92
<211> LENGTH: 45
<212> TYPE: DNA
<213> ORGANISM: Homo sapiens

<400> SEQUENCE: 92
agatagagtc gatgccagct gtcgtctgac accacagtac ttact             45

<210> SEQ ID NO 93
<211> LENGTH: 26
<212> TYPE: DNA
<213> ORGANISM: Homo sapiens

<400> SEQUENCE: 93
tatcctaaaa atcctgcttt aatttg                                  26

<210> SEQ ID NO 94
<211> LENGTH: 36
<212> TYPE: DNA
<213> ORGANISM: Homo sapiens

<400> SEQUENCE: 94
tacatctagt tgtatagttc ttatctctaa attatc                       36

<210> SEQ ID NO 95
<211> LENGTH: 45
<212> TYPE: DNA
<213> ORGANISM: Homo sapiens

<400> SEQUENCE: 95
ggctatgatt cgcaatgctt gaaagcatat taccaataaa aatta             45

<210> SEQ ID NO 96
<211> LENGTH: 28
<212> TYPE: DNA
<213> ORGANISM: Homo sapiens

<400> SEQUENCE: 96
aattaatgat tggtatgaca agttatga                                28

<210> SEQ ID NO 97
<211> LENGTH: 31
<212> TYPE: DNA
<213> ORGANISM: Homo sapiens

<400> SEQUENCE: 97
tgaaagttag atttgtgtta acttctatta g                            31

<210> SEQ ID NO 98
<211> LENGTH: 45
<212> TYPE: DNA
<213> ORGANISM: Homo sapiens
```

```
<400> SEQUENCE: 98
gacctgggtg tcgataccta ataggtgcca taaggaagag tcaga          45

<210> SEQ ID NO 99
<211> LENGTH: 26
<212> TYPE: DNA
<213> ORGANISM: Homo sapiens

<400> SEQUENCE: 99
gtgcaaatga aacaagaatt aataag                               26

<210> SEQ ID NO 100
<211> LENGTH: 24
<212> TYPE: DNA
<213> ORGANISM: Homo sapiens

<400> SEQUENCE: 100
aatatgacct taaagcattc tcca                                 24

<210> SEQ ID NO 101
<211> LENGTH: 45
<212> TYPE: DNA
<213> ORGANISM: Homo sapiens

<400> SEQUENCE: 101
cgtgccgctc gtgatagaat aacacatggc acagatggag gaaat          45

<210> SEQ ID NO 102
<211> LENGTH: 45
<212> TYPE: DNA
<213> ORGANISM: Homo sapiens

<400> SEQUENCE: 102
acgcacgtcc acggtgattt gccacccagt cagcaggtat ttatt          45

<210> SEQ ID NO 103
<211> LENGTH: 29
<212> TYPE: DNA
<213> ORGANISM: Homo sapiens

<400> SEQUENCE: 103
ttagtttact tttgttgata ttatgtggg                            29

<210> SEQ ID NO 104
<211> LENGTH: 26
<212> TYPE: DNA
<213> ORGANISM: Homo sapiens

<400> SEQUENCE: 104
tttgatatag tggcaaaaaa tttagg                               26

<210> SEQ ID NO 105
<211> LENGTH: 45
<212> TYPE: DNA
<213> ORGANISM: Homo sapiens

<400> SEQUENCE: 105
gtgattctgt acgtgtcgcc ttctattctt aataatcagt gaaag          45
```